US008809285B2

(12) United States Patent
Guo et al.

(10) Patent No.: US 8,809,285 B2
(45) Date of Patent: Aug. 19, 2014

(54) MONOPHOSPHORYLATED LIPID A DERIVATIVES

(75) Inventors: Zhongwu Guo, Northville, MI (US); Qianli Wang, Chicago, IL (US); Shouchu Tang, Detroit, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 13/387,934

(22) PCT Filed: Jul. 30, 2010

(86) PCT No.: PCT/US2010/043902
§ 371 (c)(1),
(2), (4) Date: Apr. 10, 2012

(87) PCT Pub. No.: WO2011/014771
PCT Pub. Date: Feb. 3, 2011

(65) Prior Publication Data
US 2012/0190633 A1    Jul. 26, 2012

Related U.S. Application Data

(60) Provisional application No. 61/230,378, filed on Jul. 31, 2009.

(51) Int. Cl.
| A61K 31/30 | (2006.01) |
| A61K 31/7028 | (2006.01) |
| A61K 31/7056 | (2006.01) |
| C07H 17/02 | (2006.01) |
| C07H 15/00 | (2006.01) |

(52) U.S. Cl.
USPC .............................. 514/25; 536/17.4; 536/4.1

(58) Field of Classification Search
USPC ..................................... 536/17.4, 4.1; 514/25
See application file for complete search history.

(56) References Cited

U.S. PATENT DOCUMENTS

| 5,223,409 | A | 6/1993 | Ladner et al. |
| 5,240,833 | A | 8/1993 | Nudelman et al. |
| 5,916,771 | A | 6/1999 | Hori et al. |
| 5,939,598 | A | 8/1999 | Kucherlapati et al. |
| 5,985,615 | A | 11/1999 | Jakobovits et al. |
| 5,994,619 | A | 11/1999 | Stice et al. |
| 5,998,209 | A | 12/1999 | Jokobovits et al. |
| 6,075,181 | A | 6/2000 | Kucherlapati et al. |
| 6,091,001 | A | 7/2000 | Jakobovits et al. |
| 6,114,598 | A | 9/2000 | Kucherlapati et al. |
| 6,130,364 | A | 10/2000 | Jakobovits et al. |
| 6,150,584 | A | 11/2000 | Kucherlapati et al. |
| 6,162,963 | A | 12/2000 | Kucherlapati et al. |
| 2005/0113297 | A1 | 5/2005 | Francois et al. |
| 2005/0147624 | A1 | 7/2005 | Jennings et al. |
| 2008/0131466 | A1 | 6/2008 | Reed et al. |
| 2009/0041836 | A1 | 2/2009 | Boons et al. |

FOREIGN PATENT DOCUMENTS

| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |

OTHER PUBLICATIONS

Chefalo et al. (Biochemistry, Mar. 21, 2006, vol. 45(11), pp. 3733-3739).*
Pan et al. (Carbohydrate Research 339 (2004) 2091-2100).*
Babcook et al., "A novel strategy for generating monoclonal antibodies from single, isolated lymphocytes producing antibodies of defined specificities," *Proc. Natl. Acad. Sci. USA*, vol. 93:7843-48, (Jul. 1996).
Baldridge et al., "Monophosphoryl Lipid A (MPL) Formulations for the Next Generation of Vaccines," *Methods*, 19, 103-107, (1999).
Barbas et al., "Assembly of combinatorial antibody libraries on phage surfaces: The gene III site," *Proc. Natl. Acad. Sci. USA*, vol. 88:7978-7982 (Sep. 1991).
Bay et al., "Induction of a Melanoma-Specific Antibody Response by a Monovalent, but not a Divalent, Synthetic GM2 Neoglycopeptide," *ChemMedChem* (2009), 4, 582-587.
Bird et al., "Single-Chain Antigen-Binding Proteins," *Science* 242: 423-426 (Oct. 1988).
Buskas et al., "Towards a Fully Synthetic Carbohydrate-Based Anticancer Vaccine: Synthesis and Immunological Evaluation of a Lipidated Glycopeptide Containing the Tumor-Associated Tn Antigen," *Angew Chem Int Ed Engl* (2005), 44, 5985-5988.
Casella et al., "Putting endotoxin to work for us: Monophosphoryl lipid A as a safe and effective vaccine adjuvant", *Cell. Mol. Life Sci.* (2008), 65, 3231-3240.
Chefalo et al., "Efficient Metabolic Engineering of GM3 on Tumor Cells by N-Phenylacetyl-D-mannosamine," Biochemistry, vol. 45(11), 3733-3739, (Mar. 21, 2006).
Chefalo et al., "Preparation and Immunological Studies of Protein Conjugates of N-Acylneuraminic Acids", Glycoconjugate J., (2004); 20(6), 407-414.
Christ et al., "Total Synthesis of the Proposed Structure of Rhodobacter sphaeroides Lipid A Resulting in the Synthesis of New Potent Lipopolysaccharide Antagonists," *J. Am. Chem. Soc.* (1994), 116, 3637-3638.

(Continued)

*Primary Examiner* — Shaojia Anna Jiang
*Assistant Examiner* — Michael C Henry
(74) *Attorney, Agent, or Firm* — Brinks Gilson & Lione

(57) ABSTRACT

The present invention provides for monophosphorylated lipid A derivatives and carbohydrate derivatives that are useful as agents in the treatment of diseases and conditions, including cancers. Also provided are pharmaceutical compositions comprising one or more compounds of Formula I-IV. In addition, methods for the treatment of cancers are provided.

9 Claims, 6 Drawing Sheets

(56) References Cited

OTHER PUBLICATIONS

Clackson et al., "Making antibody fragments using phage display libraries," *Nature* 352:624-628 (Aug. 1991).
Danishefsky et al., "From the Laboratory to the Clinic: A Retrospective on Fully Synthetic Carbohydrate-Based Anticancer Vaccines," *Angew. Chem. Int. Ed.* (2000), 39, 836-863).
Darveau, R. P., "Lipid A diversity and the innate host response to bacterial infection," *Curr. Opin. Microbiol.* (1998), 1:36-42.
Demchenko et al., "Synthesis and Biological Evaluation of Rhizobium sin-1 Lipid A Derivatives," *J. Am. Chem. Soc.* (2003), 125, 6103-6112.
Dobrovolskaia et al., "Toll receptors, CD14, and macrophage activation and deactivation by LPS," *Microbes Infect.* (2002), 4, 903-914.
Dullenkopf et al., "Synthesis of a Structurally Defined Antigen-Immunostimulant Combination for Use in Cancer Vaccines," *Chem Eur. J.* (1999), 5, No. 8, 2432.
Erridge et al., "Structure and function of lipopolysaccharides," *Microbes Infect.* (2002), 4, 837-851.
Fujimoto et al., "Synthesis and bioactivity of fluorescence- and biotin-labeled lipid A analogues for investigation of recognition mechanism in innate immunity," *Tetrahedron Letters* (2006), 47, 539-543.
Fukase et al., "Synthesis of Rubrivivax gelatinosus Lipid A and Analogues for Investigation of the Structural Basis for Immunostimulating and Inhibitory Activities," *Bull. Chem. Soc. Jpn.*, (2008), 81, No. 7, 796-819.
Gram et al, "In vitro selection and affinity maturation of antibodies from a naïve combinatorial immunoglobulin library," *Proc. Natl. Acad. Sci. USA* 89:3576-3580 (1992).
Green et al., "Antigen-specific human monoclonal antibodies from mice engineered with human Ig heavy and light chain YACs," *Nature Genetics* 7:13-21 (1994).
Greenspan et al., "Intermolecular cooperativity: a clue to why mice have IgG3?," *Immunol Today* 13, No. 5, 164-8 (1992).
Griffiths et al., "Human anti-self antibodies with high specificity from phage display libraries," *EMBO J.* 12, No. 2, 725-734 (1993).
Guo, Zhongwu et al., "Biochemical Engineering of Surface α2-8 Polysialic Acid for Immunotargeting Tumor Cells*", *The Journal of Biological Chemistry*, vol. 275, No. 42, pp. 32832-32836, (Oct. 20, 2000).
Guo, Zhongwu et al., "Recent Development in Carbohydrate-Based Cancer Vaccines," *Current Opinion in Chemical Biology*, 13(5-6), pp. 608-617, (Sep. 18, 2009).
Hansen et al, "Studies Directed to the Synthesis of Oligochitosans-Preparation of Building Blocks and Their Evaluation in Glycosylation Studies," *Eur. J. Org. Chem.*, (2007), 3392-3401.
Hedlund et al., "Evidence for a human-specific mechanism for diet and antibody-mediated inflammation in carcinoma progression," *Proc. Natl. Acad. Sci. USA*, 105, No. 48, 18936-18941 (2008).
Holliger P. et al., "Diabodies: Small bivalent and bispecific antibody fragments," *Proc. Natl. Acad. Sci. USA* 90: 6444-6448 (1993).
Huse et al., "Generation of a Large Combinatorial Library of the Immunolglobulin Repertoire in Phage Lambda," *Science* 246:1275-1281 (1989).
Huston et al., "Protein engineering of antibody binding sites: Recovery of specific activity in an anti-digoxin single-chain Fv analogue produced in *Escherichia coli*," *Proc. Natl. Acad. Sci. USA* 85:5879-5883 (1988).
Ingale et al., "Robust immune responses elicited by a fully synthetic three-component vaccine," *Nat. Chem Biol.* (2007), 10, 663-667.
Jiang et al., "Monophosphoryl lipid A analogues with varying 3-O-substitution: synthesis and potent adjuvant activity," *Carbohydr. Res.*, (2007), 342, 784-796.
Johnson et al., "3-*O*-Desacyl Monophosphoryl Lipid A Derivatives: Synthesis and Immunostimulant Activities," *J. Med. Chem.* (1999), 42, 4640-4649.
Kohler & Milstein, "Continuous cultures of fused cells secreting antibody of predefined specificity," *Nature* 256: 495-497 (1975).

Kolb et al., "Click Chemistry: Diverse Chemical Function from a Few Good Reactions," *Angew. Chem. Int. Ed.* (2001), 40, 2004-2021.
Kozbor et al., "The production of monoclonal antibodies from human lymphocytes," *Immunology Today* 4:72 (1983).
Krug et al., "Vaccination of Small Cell Lung Cancer Patients with Polysialic Acid or N-Propionylated Polysialic Acid Conjugated to Keyhole Limpet Hemocyanin," *Clin. Cancer Res.*, (2004); 10-916-923.
Kudryashov et al., "Toward optimized carbohydrate-based anticancer vaccines: Epitope clustering, carrier structure, and adjuvant all influence antibody responses to Lewis$^y$ conjugates in mice," *Proc Natl Acad Sci USA* (2001), 98, 3264-3269.
Kulshin et al., "Structural Characterization of the Lipid A Component of Pathogenic *Neisseria meningitides*," *Journal of Bacteriology* (1992), pp. 1793-1800.
Liu et al., "Biochemical Engineering Surface α2,8 Polysialic Acid for Immunotargeting Tumor Cells," *J. Biol. Chem.*, (2000); 75-32832-32836.
Luchansky, Sarah et al., "Expanding the Diversity of Unnatural Cell-Surface Sialic Acids," *ChemBioChem*, vol. 5, No. 3, pp. 371-374, (2004).
McCafferty et al., "Phage antibodies: filamentous phage displaying antibody variable domains," *Nature* 348:552-554 (1990).
Mochizuki et al., "Lipid A-Type Pyrancarboxylic Acid Derivatives, their Synthesis and their Biological Activities," *Tetrahedron* (2000), 56, 7691-7703.
Niu et al., "Efficient Formation and Cleavage of Benzylidene Acetals by Sodium Hydrogen Sulfate Supported on Silica Gel," *Synlett* (2007), 2116-2120.
Pan et al., "Accessibility of N-acyl-D-mannosamines to N-acetyl-D-neuraminic acid aldolase," *Carbohydrate Res.* 339: 2091-2100 (2004).
Pan et al., "Synthesis and Immunological Properties of N-Modified GM3 Antigens as Therapeutic Cancer Vaccines," *J. Med. Chem.*, (2005), 48, 875-883.
Pan, Yanbin et al., "Synthesis and Immunological Properties of N-Modified GM3 Antigens as Therapeutic Cancer Vaccines," *Journal of Medicinal Chemistry*, vol. 48, No. 3, pp. 875-883, (Jan. 13, 2005).
Perlmutter et al., "Subclass Restriction of Murine Anti-Carbohydrate Antibodies," *J. Immunol* 121, No. 2, 556-72 (1978).
Persing et al., "Taking toll: lipid A mimetics as adjuvants and immunomodulators," *Trends Microbiol.* (2002), 10 (Suppl.), S32).
Qureshi et al., "Structure of lipid A and cell activation," *Journal of Endotoxin Res.* (1999), vol. 5, No. 3, p. 147.
Qureshi et al., "Monophosphoryl Lipid A Obtained from Lipopolysaccharides of *Salmonella minnesota* R595," *J. Biol. Chem.* (1985), v.260, No. 9, 5271-5278.
Rembold et al., "Synthesis of Kdo-α-glycosides of lipid A derivatives," *Carbohydr. Res.*, (1993), 246, 137-159.
Renaudet et al., "Towards a Self-Adjuvanting Multivalent B and T cell Epitope Containing Synthetic Glycolipopeptide Cancer Vaccine," *ChemMedChem* (2008), 3, 737-741.
Rietschel et al., "Bacterial endotoxin: molecular relationships of structure to activity and function," *FASEB J.* (1994), 8, 217).
Roy et al., "Cu(II)-Self-assembling bipyridyl-glycoclusters and dendrimers bearing the Tn-antigen cancer marker: syntheses and lectin binding properties," *Tetrahedron* (2003), 59, 3881-3893.
Santhanam et al., "Preparation of a Lipid A Derivative That Contains a 27-Hydroxyoctacosanoic Acid Moiety," *Org. Letters* (2004), vol. 6, No. 19, 3333-3336.
Santhanam et al., "Synthesis and Biological Evaluation of a Lipid A Derivative That Contains an Aminogluconate Moiety," *Chem. Eur. J.* (2004), 10, 4798-4807.
Tang, Shouchu et al., "Synthesis of a Monophosphoryl Derivative of *Escherichia coli* Lipid A and Its Efficient Coupling to a Tumor-Associated Carbohydrate Antigen," *Chemistry Eur. J.*, vol. 16, No. 4, pp. 1319-1325, (Jan. 25, 2010).
Toyokuni et al., "Synthetic Vaccines: Synthesis of a Dimeric Tn Antigen-Lipopeptide Conjugate That Elicits Immune Responses against Tn-Expressing Glycoproteins," *J. Am Chem Soc* (1994), 116, 395-396.

(56) References Cited

OTHER PUBLICATIONS

Ulmer et al., "Biological Activity of Synthetic Phosphonooxyethyl Analogs of Lipid A and Lipid A Partial Structures," *Infection and Immunity* (1992), 60, 3309-3314.

Van Amersfoort et al., "Receptors, Mediators, and Mechanisms Involved in Bacterial Sepsis and Septic Shock," *Clin. Microbiol. Rev.* (2003), v.16, No. 3, 379-414.

Wang et al., "Synthetic and Immunological Studies of 5'-N-phenylacetyl sTn to Develop Carbohydrate-Based Cancer Vaccines and to Explore the Impacts of Linkage between Carbohydrate Antigens and Carrier Proteins," *Bioconjugate Chem.*, 19, pp. 2060-2067 (2008).

Wang, Qianli et al. "Synthesis of a Monophosphoryl Lipid A Derivative and Its Conjugation to a Modified Form of Tumor-Associated Carbohydrate Antigen GM3," *Chemical Communications*, (37), pp. 5536-5537, (Oct. 7, 2009).

Wang, Qianli et al., "Efficient glycoengineering of GM3 on melanoma cell and monoclonal antibody-mediated selective killing of the glycoengineered cancer cell", *Bioorganic and Medical Chemistry*, vol. 15, No. 24, pp. 7561-7567, (Dec. 15, 2007).

Ward et al., "Binding activities of a repertoire of single immunoglobulin variable domains secreted from *Escherichia coli*," *Nature* v.341:544-546 (1989).

Watanabe et al., "Synthesis of lipid A type carboxymethyl derivatives with ether chains instead of ester chains and their LPS-antagonistic activities," *Carbohydr. Res.* (2003), 338, 47-54.

Wu, Jian et al., "Improving the Antigenicity of sTn Antigen by Modification of Its Sialic Acid Residue for Development of Glycoconjugate Cancer Vaccines", *Bioconjugate Chemistry*, vol. 17, No. 6, pp. 1537-1544, (2006).

Xue et al., "Neoglycoprotein Cancer Vaccines: Synthesis of an Azido Derivative of GM3 and Its Efficient Coupling to Proteins through a New Linker," *Tetrahedron Lett.*, (2002), 43;1599-1602.

Yin et al., "Synthesis of Lipid A Derivatives and Their Interactions with Polymyxin B and Polymyxin B Nonapeptide," *J. Am. Chem. Soc.*, (2003), 125, 2426-2435.

Yoshizaki et al., "First Total Synthesis of the Re-Type Lipopolysaccharide," *Angew. Chem. Int. Ed.* (2001), 40, 1475.

Zamyatina et al., "Synthesis and purity assessment of tetra- and pentaacyl lipid A of Chlamydia containing®-3-hydroxyicosanoic acid," *Tetrahedron* (2004), 60, 12113-12137.

Zhang et al., "The influence of the long chain fatty acid on the antagonistic activities of *Rhizobium sin*-1 lipid A," *Bioorg. Med. Chem.* (2007), 15, 4800-4812.

Zhang et al., "Modulation of Innate Immune Responses with Synthetic Lipid A Derivatives," *J. Am. Chem. Soc.*, (2007), 129, 5200-5216.

Baldridge et al., "Monophosphoryl Lipid A and Synthetic Lipid A Mimetics As TLR4-Based Adjuvants and Immunomodulators," *Vaccine Adjuvants*; (2006), pp. 235-255.

Berge et al., "Pharmaceutical Salts," *Journal of Pharmaceutical Sciences*; (Jan. 1977), vol. 66., No. 1, pp. 1-19.

Cole et al., "The EBV-Hybridoma Technique and its Application to Human Lung Cancer," *Monoclonal Antibodies and Cancer Therapy*, (1985), pp. 77-96.

Fuchs et al., "Targeting Recombinant Antibodies to the Surface of *Escherichia coli*: Fusion to a Peptidoglycan Associated Lipoprotein," *BioTechnology* (1991), pp. 1370-1372.

Garrard et al., "Fab Assembly and Enrichment in a Monovalent Phage Display System," *Nature Biotechnology*, (1991), vol. 9, No. 7-12; pp. 1373-1377.

Hawkins et al., "Selection of Phage Antibodies by Binding Affinity Mimicking Affinity Maturation," *J. Mol. Biol.*, (1992), 226, pp. 889-896.

Hay et al., "Bacteriophage cloning and *Escherichia coli* expression of a human IgM Fab," *Hum. Antibod. Hybridomas*, (1992), vol. 3, pp. 81-85.

Hoogenboom et al, "Multi-subunit proteins on the surface of filamentous phage: methodologies for displaying antibody (Fab) heavy and light chains," *Nucleic Acids Research*, (1991), vol. 19, No. 15, pp. 4133-4137.

Jennings et al., "Synthetic Glycoconjugates as Human Vaccines," *Neoglycoconjugates: Preparation and Applications,* (1994); pp. 325-371.

Marks et al., "By-Passing Immunization: Building High Affinity Human Antibodies by Chain Shuffling," *Bio/technology*, (1992), vol. 10, No. 7, pp. 779-783.

Morrison et al., "Structure-Function Relationships of Bacterial Endotoxins," *Infectious Disease Clinics of North America*, (Jun. 1999), vol. 13, No. 2, pp. 313-340.

Poljak, R.J., "Production and structure of diabodies," *Structure* (Dec. 1994), 2, pp. 1121-1123.

Ribi et al., "Biological Activities of Monophosphoryl Lipid A," *Microbiology*, (1986), pp. 9-13.

* cited by examiner

MONOPHOSPHORYLATED LIPID A DERIVATIVES

CROSS REFERENCE TO RELATED APPLICATIONS

This application is related to and claims the benefit of priority to PCT/US2010/043902, filed on Jul. 30, 2010 which application claims the benefit of U.S. Provisional Patent Application No. 61/230,378 filed Jul. 31, 2009, the content of which is hereby incorporated by reference in its entirety.

FEDERALLY SPONSORED RESEARCH AND DEVELOPMENT

This invention was made with government support under grant number R01 CA095142 awarded by the National Institutes of Health (NIH). The U.S. government has certain rights to the invention.

BACKGROUND

All cells are covered by a thick layer of carbohydrates, known as the glycocalyx, which consists of many different carbohydrate epitopes—some are cell-type specific. Cancer cells express certain unique or excessive carbohydrate structures, termed tumor-associated carbohydrate antigens (TACAs). They are important molecular targets for the development of therapeutic cancer vaccines or cancer immunotherapies, because TACAs are typically rich and exposed on the cancer cell surface and they are ideally situated for the immune system recognition and reactions. Furthermore, TACAs are widespread in malignant tissues and closely correlated with various stages of tumor progression. The goal of cancer immunotherapy is to educate the patient's immune system, either by using antibodies or by vaccination, to recognize and target the antigens uniquely expressed on cancer cells for cancer elimination.

However, a major issue associated with TACAs is that carbohydrate antigens are generally poorly immunogenic. Another issue for TACAs is that they are tolerated by the patient's immune system, because they are perceived as "self" or "normal" antigens and are not recognizable by the human immune system. Therefore, it is very difficult to use natural TACAs for the development of functional cancer vaccines.

Lipopolysaccharides (LPS), which constitute the major components on the cell surface of Gram-negative bacteria (Erridge et al., *Microbes Infect.* (2002), 4, 837), have been proved to be particularly endotoxic and cause septicemia. (Van Amersfoort et al., *Clin. Microbiol. Rev.* (2003), 16, 379). It has been further demonstrated that the LPS anchor part, namely, lipid A, is primarily responsible for the endotoxicity of LPS. Lipid A binds to Toll-like receptor 4 (TLR4) to activate a cascade of immunological responses, including the production of a number of cytokines and chemokines such as tumor necrosis factor-α (TNF-α), interleukin-1β (IL-1β), IL-6, and interferon-β (IFN-β). (Dobrovolskaia et al., *Microbes Infect.* (2002), 4, 903). Thus, lipid A has become a valuable molecular template in the discovery of new immunostimulants, (Persing et al., *Trends Microbiol.* (2002), 10 (Suppl.), S32); Baldridge et al., in *Vaccine Adjuvants* (Eds.: C. J. Hackett, D. A. J. Harn), Humana Press Inc., Totowa, N.J., (2006), pp. 235), for example as a vaccine adjuvant, and in the design and development of novel conjugate vaccines. (Baldridge et al., *Methods* (1999), 19, 103).

In order to understand and eventually mitigate the endotoxicity of lipid A for the development of useful immunostimulant, numerous lipid A derivatives have been designed, synthesized, and biologically assayed. (Qureshi et al., *Endotoxin Res.* (1999), 5, 147); Morrison et al., *Infect. Dis. Clin. N. Am.* (1999), 13, 313); R. P. Darveau, *Curr. Opin. Microbiol.* (1998), 1, 36); Rietschel et al., *FASEB J.* (1994), 8, 217). Some examples of Lipid A molecules are denoted in Table 1 below.

TABLE 1

Various Lipid A and Monophosphoryl lipid A (MPLA) molecules

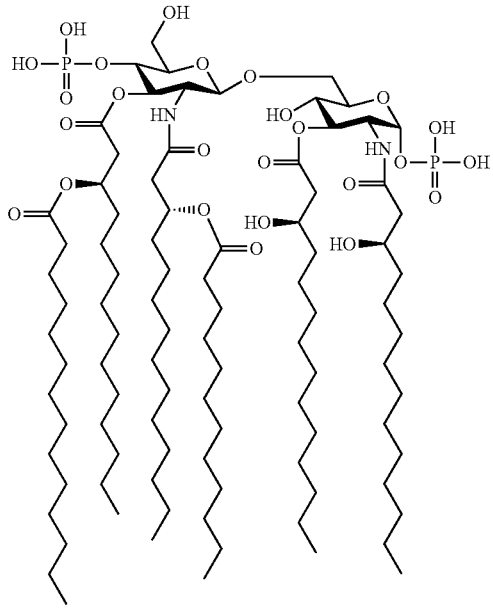

*E. coli* lipid A

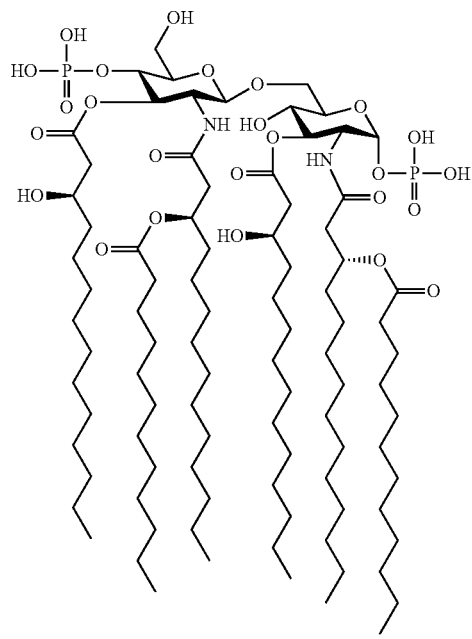

*N. meningitidis* lipid A

TABLE 1-continued

Various Lipid A and Monophosphoryl lipid A (MPLA) molecules

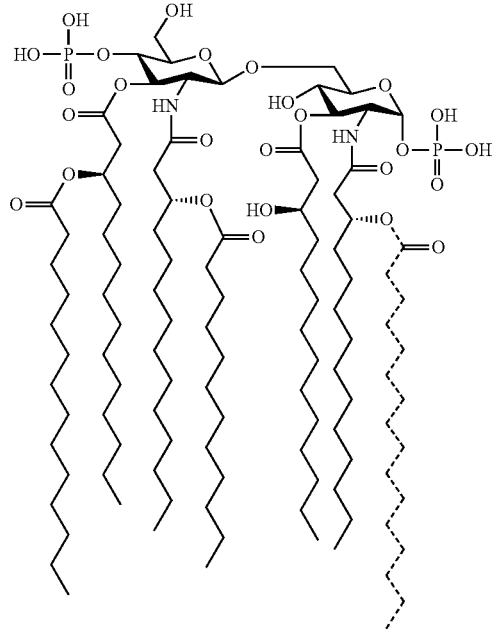

*S. minnesota* lipid A

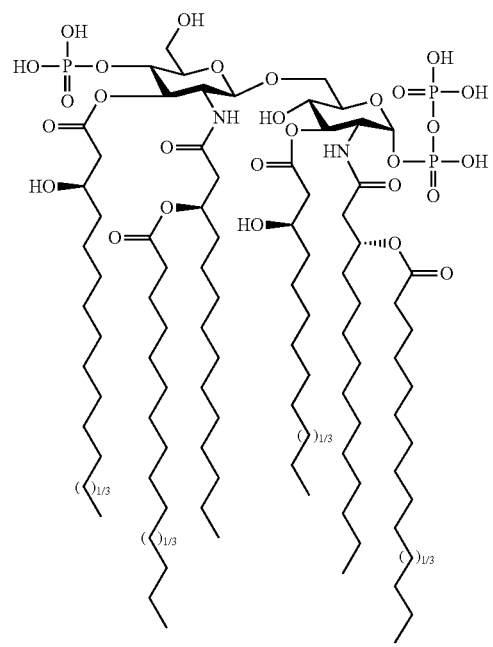

*K. pneumoniae* lipid A

TABLE 1-continued

Various Lipid A and Monophosphoryl lipid A (MPLA) molecules

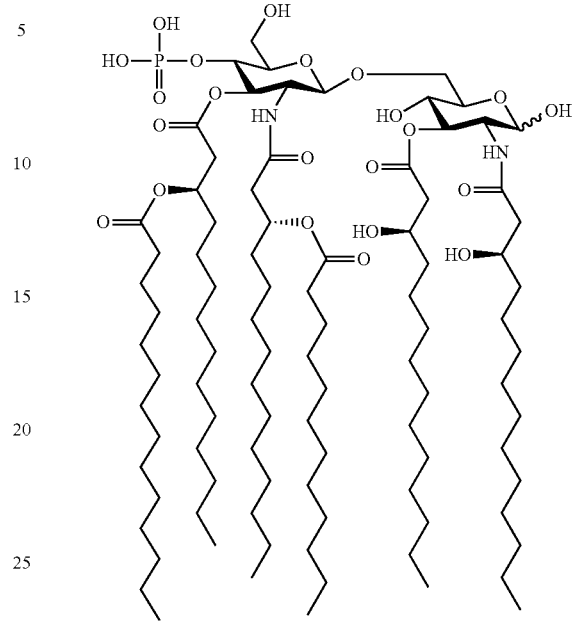

monophosphoryl *E. Coli* lipid A

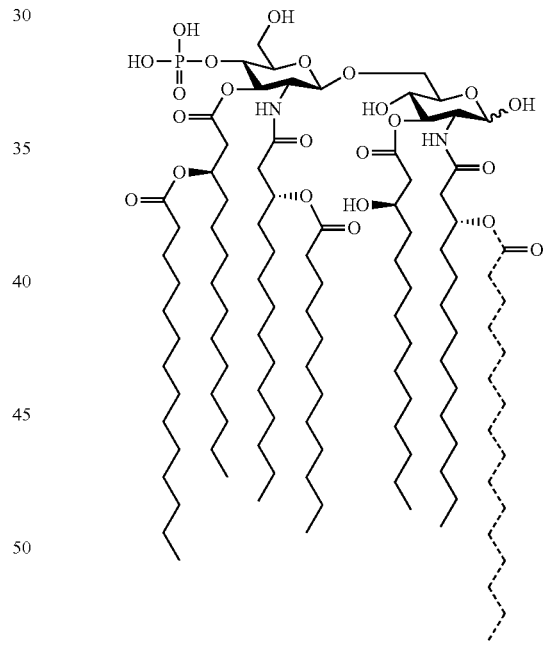

monophosphoryl *S. minnesota* lipid A

It appears that the diphosphorylated hexa-acyl form of lipid A, such as *Escherichia coli* lipid A (Table 1), is optimally recognized by TLR4 to exhibit the full spectrum of endotoxicity (Erridge et al. (2002)). Most importantly, it was observed that the endotoxic activity of lipid A could be significantly reduced after the removal of its anomeric phosphate group, (Erridge et al., *Microbes Infect*. (2002), 4, 837), while its immunostimulatory property remained unaffected. For example, although *Salmonella minnesota* lipid A is a potent endotoxin, its 4'-O-monophosphorylated form is essentially nontoxic. (Qureshi et al., *J. Biol. Chem*. (1985), 260, 5271);

Ribi et al., *Microbiol.* (1986), 9). MPLA has been proved to be clinically safe as vaccine adjuvant (Casella et al., *Cell. Mol. Life Sci.* (2008), 65, 3231) and even has been explored as potential vaccines against bacteria and cancer. (Baldridge et al. (1999)). Meanwhile, the special carbohydrates expressed by bacterial and cancer cells are important targets for the design and development of bacterial and cancer vaccines. (Jennings et al., *Neoglycoconjugates: Preparation and Applications* (Eds.: Y. C. Lee, R. T. Lee), Academic Press, San Diego, (1994), pp. 325; Danishefsky et al., *Angew. Chem. Int. Ed.* (2000), 39, 837). However, a major problem for carbohydrate antigens, especially the tumor-associated carbohydrate antigens (TACAs), is that they are typically poorly immunogenic. (Jennings et al. (1994). To overcome this problem, much recent effort has been focusing on synthetic multicomponent glycoconjugate vaccines, which consist of a carbohydrate antigen, an immunostimulant, and/or other functional epitopes. (Toyokuni et al., *J Am Chem Soc* (1994), 116, 395); Dullenkopf et al., *Chem Eur J* (1999), 5, 2432); Kudryashov et al., *Proc Natl Acad Sci USA* (2001), 98, 3264; Buskas et al., *Angew Chem Int Ed Engl* (2005), 44, 5985); Renaudet et al., *Chem Med Chem* (2008), 3, 737); Ingale et al., *Chem biochem* (2009), 10, 455); Bay et al., *Chem Med Chem* (2009), 4, 582). Therefore, there is a need in the art for methods and compounds relating to TACAs for cancer vaccines and immunotherapies.

SUMMARY

In one aspect, the present invention provides for compounds of formula I: (monophosphorylated lipid A)-L-X (I); wherein L is a linker of the formula —(CH$_2$)$_2$—NHC(O)—(CH$_2$)$_a$—C(O)NH—(CH$_2$)$_b$—,

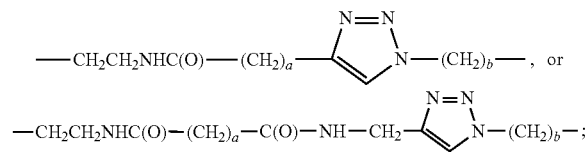

wherein a and b are integers selected from 2 to 6; and
X is

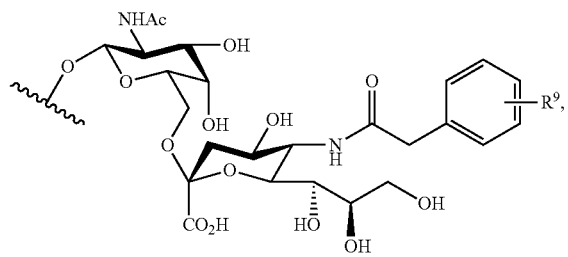

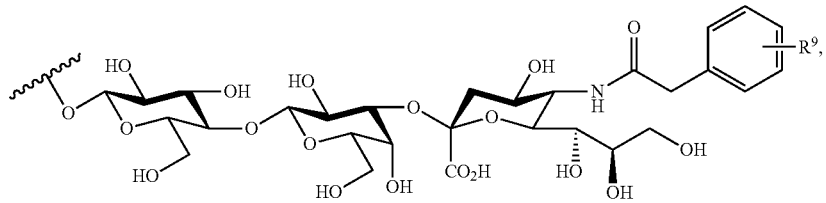

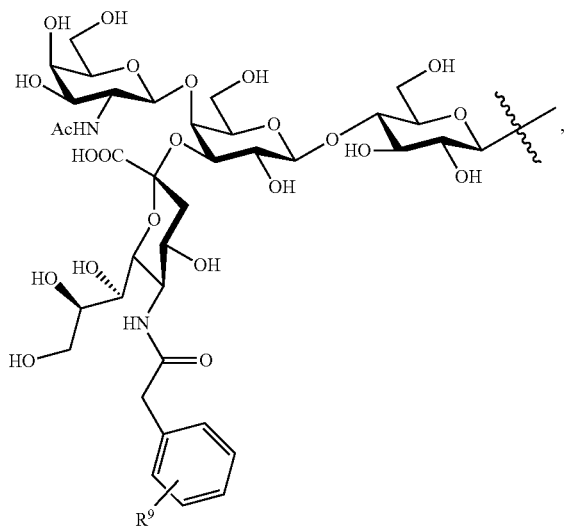

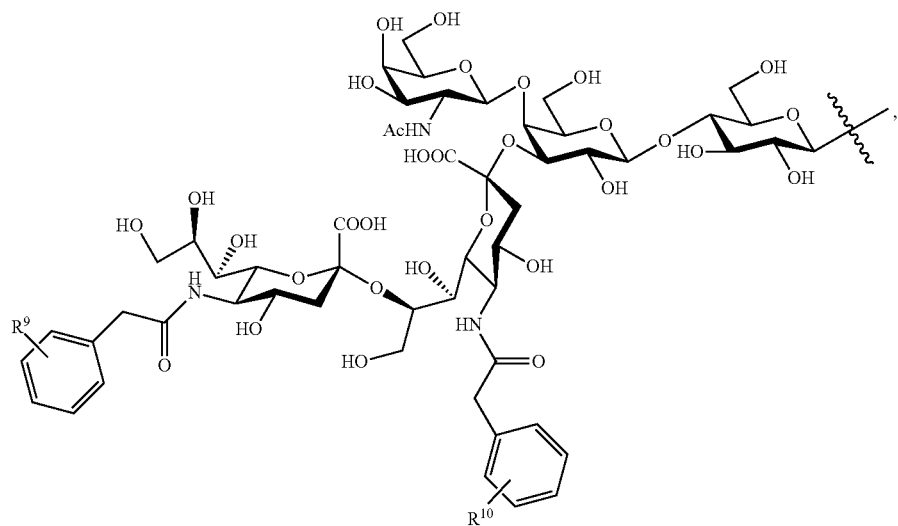
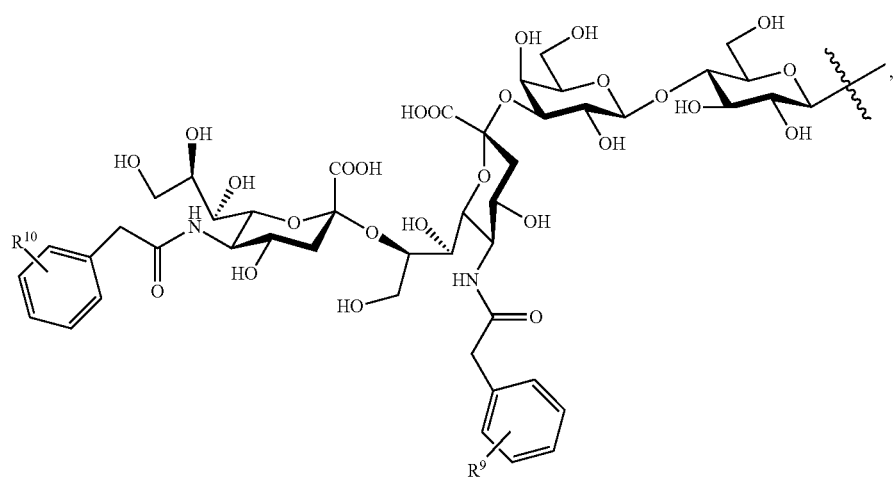
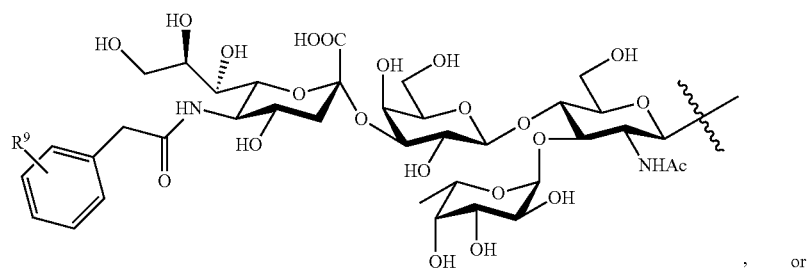
, or

-continued

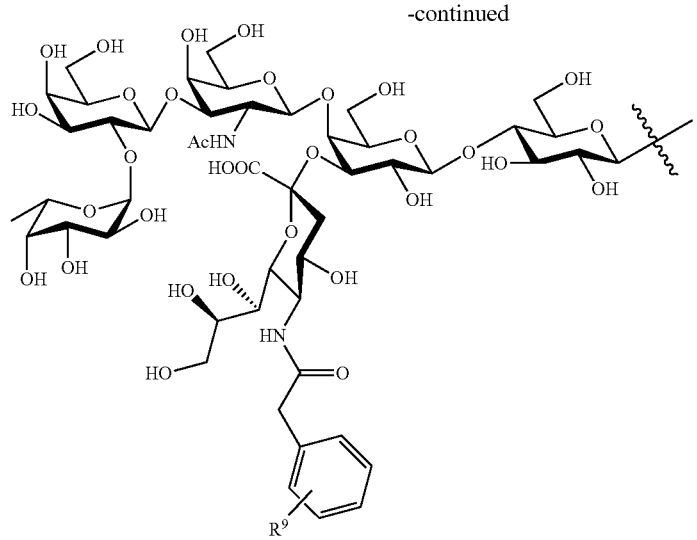

wherein $R^9$ and $R^{10}$ are independently selected from the group consisting of: $C_1$-$C_6$ alkyl, —$OC_1$-$C_4$ alkyl, —C(O) $C_1$-$C_4$ alkyl, or halo; or a pharmaceutically acceptable salt thereof.

In certain embodiments of Formula I, the monophosphorylated lipid A is represented by the following formula:

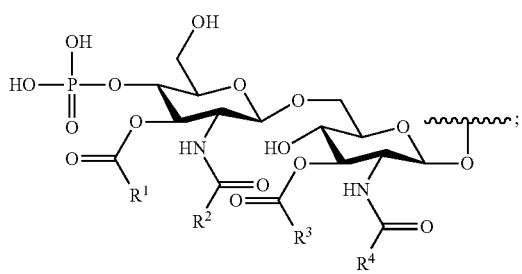

$R^1$ is —$CH_2$—CH($OR^5$)($CH_2$)$_m$$CH_3$, $R^5$ is H or —C(O)—($CH_2$)$_n$$CH_3$, m is an integer selected from 10 to 12, and n is 12; $R^2$ is —$CH_2$—CH($OR^6$)($CH_2$)$_p$$CH_3$, $R^6$ is —C(O)—($CH_2$)$_q$$CH_3$, wherein p is 10, and q is an integer selected from 10 to 12; $R^3$ is —$CH_2$—CH($OR^7$)($CH_2$)$_r$$CH_3$, $R^7$ is H, and r is an integer selected from 8 to 10; $R^4$ is —$CH_2$—CH($OR^8$)($CH_2$)$_s$$CH_3$, $R^8$ is H or —C(O)—($CH_2$)$_t$$CH_3$, s is 10 or 11, and t is an integer selected from 11 to 13; or a pharmaceutically acceptable salt thereof.

In certain embodiments of Formula I, the monophosphorylated lipid A is represented by the following formula:

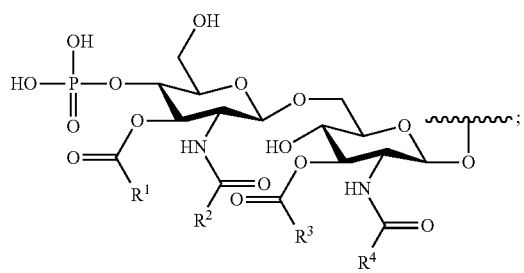

wherein $R^1$ is —($CH_2$)$_m$$CH_3$, wherein m is an integer selected from 10 to 12; $R^2$ is —$CH_2$—CH($OR^6$)($CH_2$)$_p$$CH_3$, $R^6$ is —C(O)—($CH_2$)$_q$$CH_3$, wherein p is 10, and q is an integer selected from 10 to 12; $R^3$ is —$CH_2$—CH($OR^7$)($CH_2$)$_r$$CH_3$, $R^7$ is H, and r is an integer selected from 8 to 10; $R^4$ is —$CH_2$—CH($OR^8$)($CH_2$)$_s$$CH_3$, $R^8$ is H or —C(O)—($CH_2$)$_t$$CH_3$, s is 10 or 11, and t is an integer selected from 11 to 13; or a pharmaceutically acceptable salt thereof.

In certain embodiments of Formula I, $R^9$ is H. In certain embodiments of Formula I, $R^9$ and $R^{10}$ are H.

In certain embodiments of Formula I, a and b are each 2.

Examples of compounds of formula I include, but are not limited to:

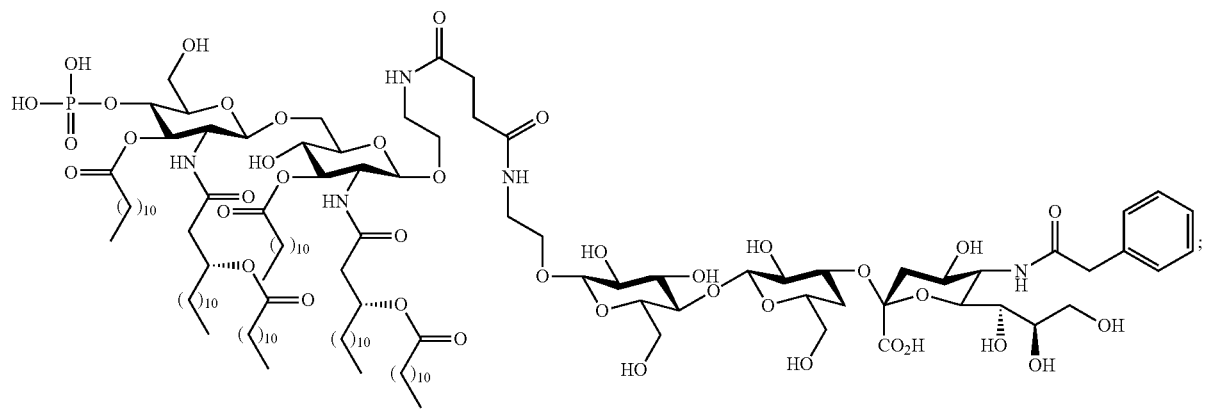

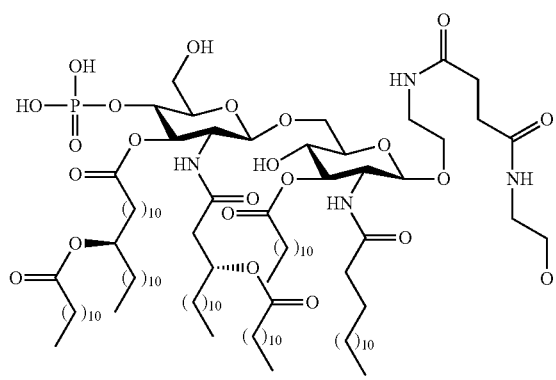
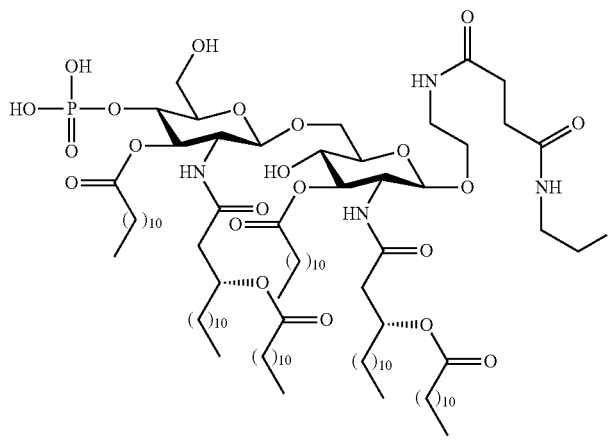
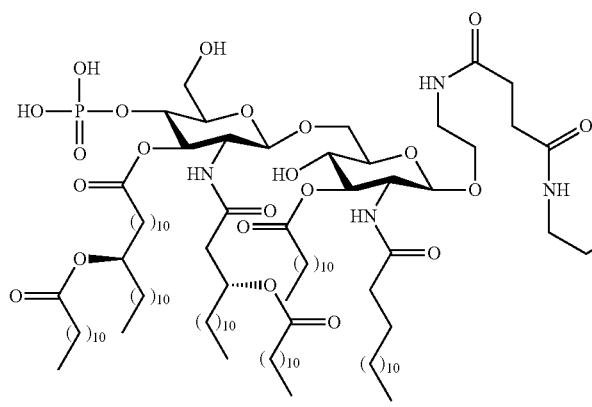
or a pharmaceutically acceptable salt thereof.
In certain embodiments of Formula I, L is a linker of the formula
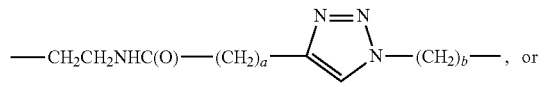
wherein a and b are integers selected from 2 to 6;
a compound of Formula II.
Examples of compounds of formula II include, but are not limited to:

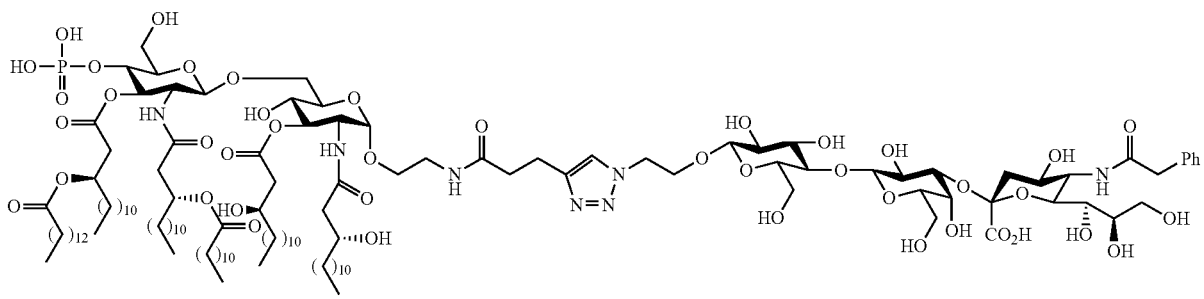

or a pharmaceutically acceptable salt thereof.

In certain embodiments of Formula I, L is a linker of the formula

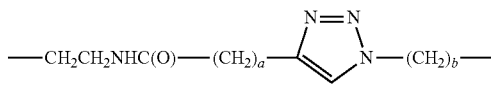

a compound of Formula II.

In certain embodiments of Formula I, L is a linker of the formula —(CH$_2$)$_2$—NHC(O)—(CH$_2$)$_a$—C(O)NH—(CH$_2$)$_b$— a compound of Formula III.

In certain embodiments of Formula I, L is a linker of the formula

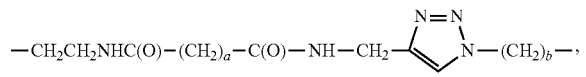

wherein a and b are integers selected from 2 to 6. An example of an embodiment of Formula I is wherein $R^{11}$ is one or two substituents independently selected from the group consisting of: $C_1$-$C_6$ alkyl, —O$C_1$-$C_4$ alkyl, —C(O)$C_1$-$C_4$ alkyl, or halo; or a pharmaceutically acceptable salt thereof.

In another aspect, the invention provides for pharmaceutical compositions that comprise a therapeutically effective amount of a compound of any one of Formulas I-IV and a pharmaceutically acceptable carrier.

In another aspect, the present invention provides for methods of modifying cancer cells for immunotherapy comprising administering a therapeutically effective amount of a compound of Formula IV to a cancer cell.

In another aspect, the present invention provides for methods of treating cancer comprising administering to a patient in need thereof a therapeutically effective amount of a compound of claim 1 and a therapeutically effective amount of a compound of formula IV:

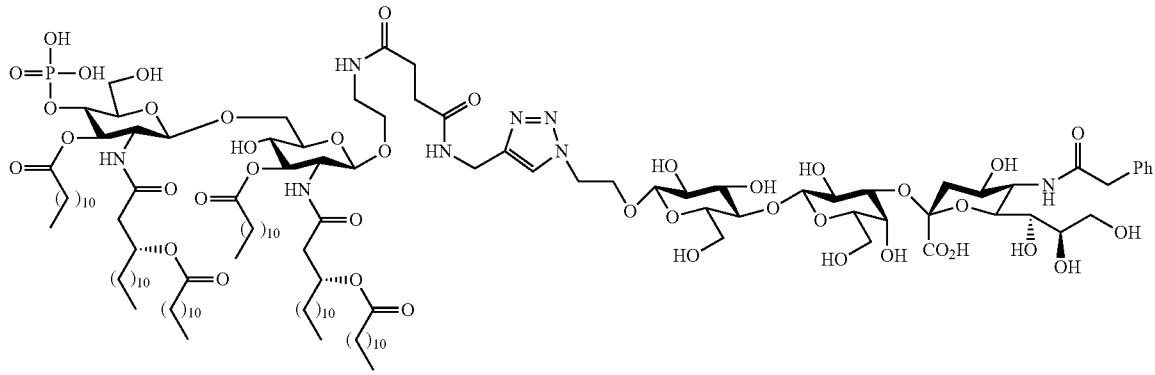

or a pharmaceutically acceptable salt thereof.

In another aspect, the invention provides for compounds of formula IV:

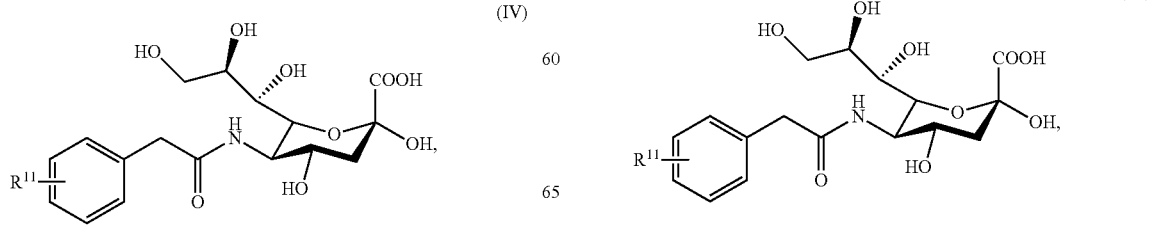

wherein $R^{11}$ is H or is one or two substituents independently selected from the group consisting of: $C_1$-$C_6$ alkyl, —O$C_1$-$C_4$ alkyl, —C(O)$C_1$-$C_4$ alkyl, or halo; or a pharmaceutically acceptable salt thereof. In certain embodiments, $R^{11}$ is H. In other embodiments, the compound of formula I is selected from the group consisting of:
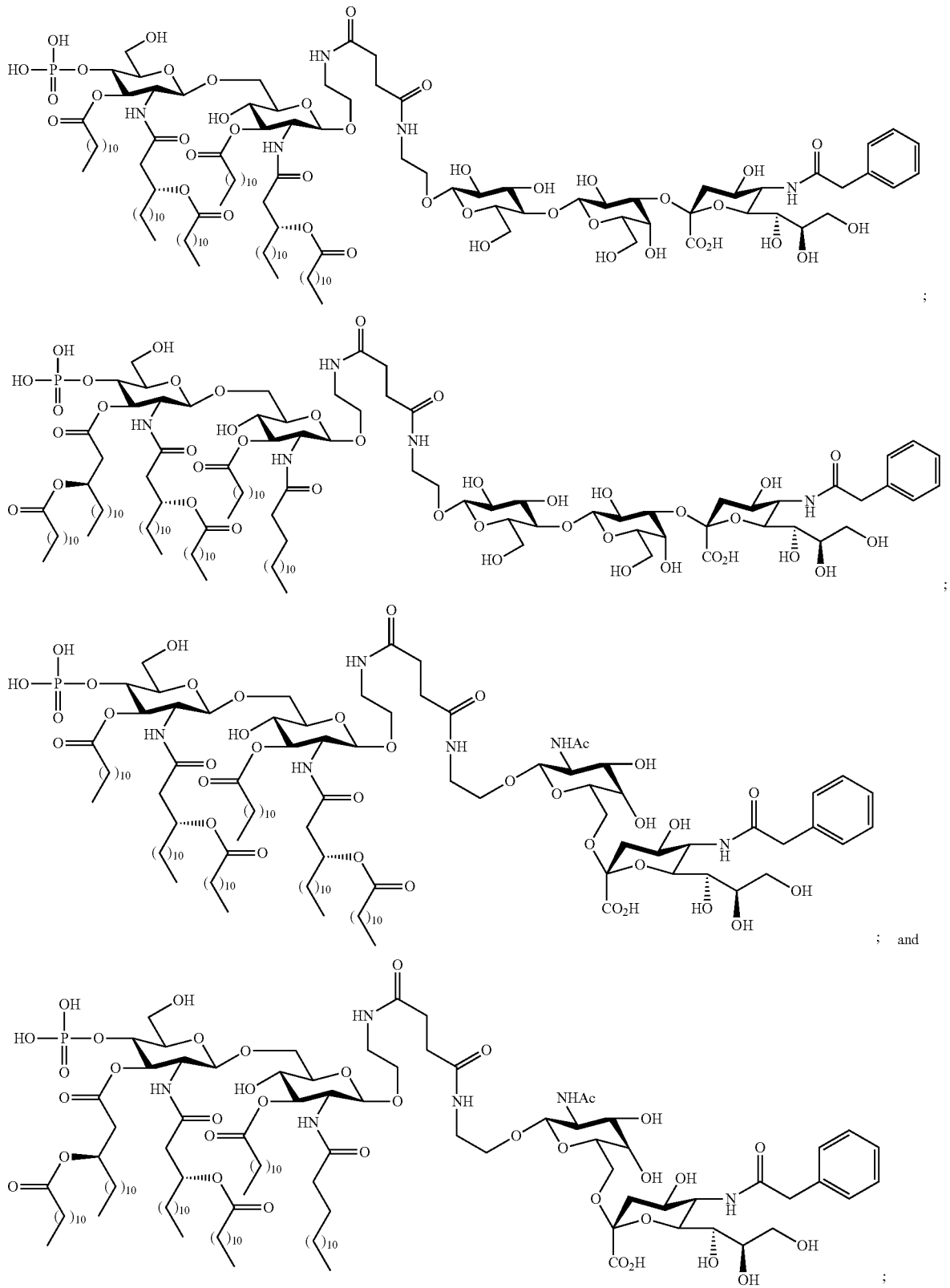

or a pharmaceutically acceptable salt thereof. In other embodiments, the compound of formula I is selected from the group consisting

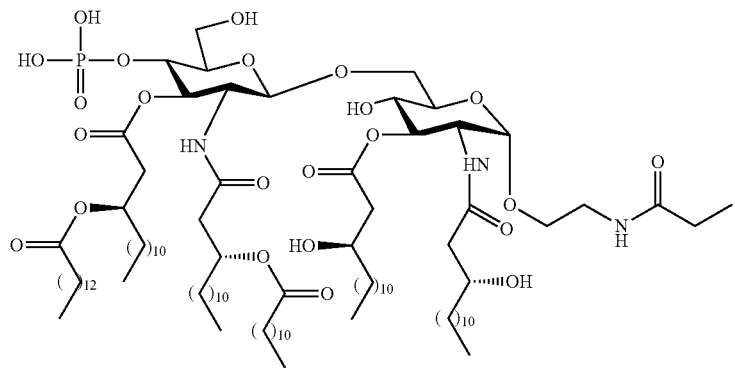

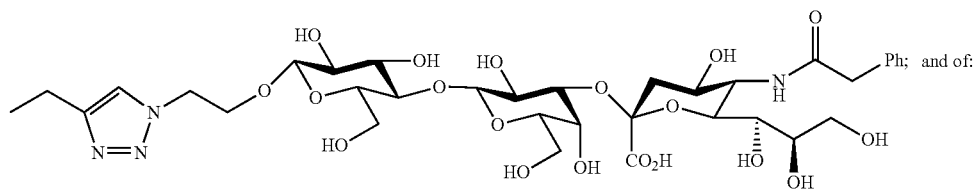

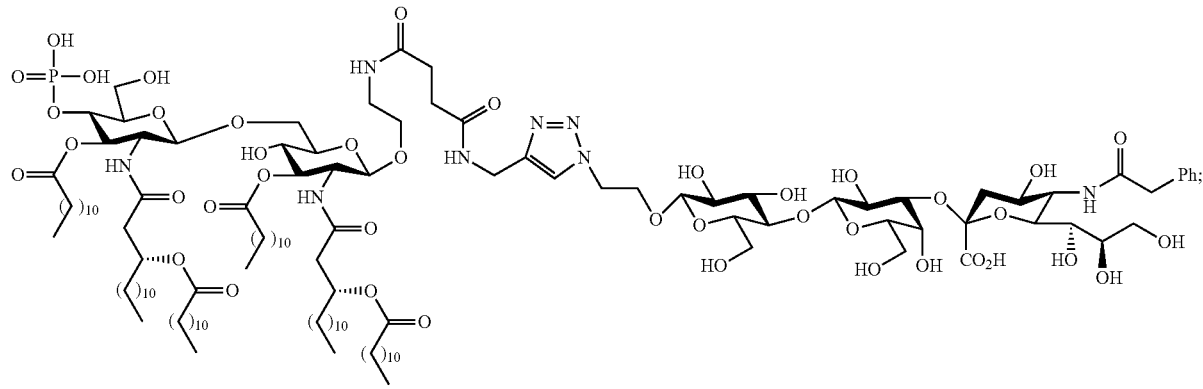

or a pharmaceutically acceptable salt thereof.

In particular embodiments, the patient is a human.

In other embodiments, the cancer is melanoma. In still other embodiments, the cancer is melanoma and the compound of formula I is selected from the group consisting of:

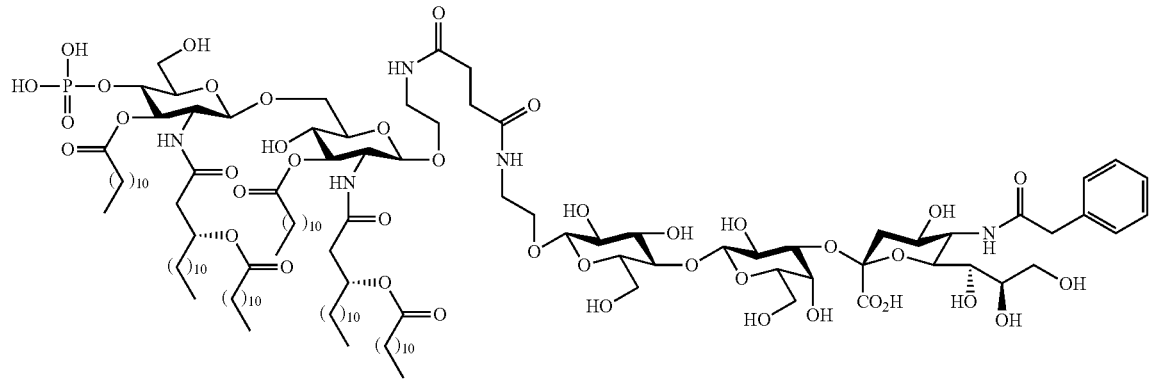

; and

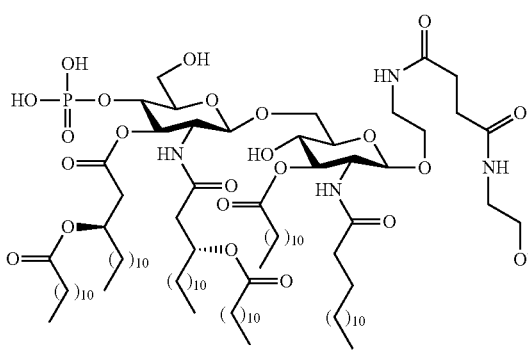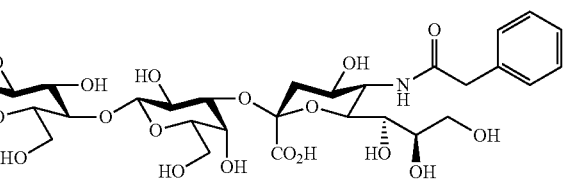

or a pharmaceutically acceptable salt thereof.

In still other embodiments, the cancer is breast, prostate, or colon cancer. In still other embodiments, the cancer is selected from the group consisting of:

breast, prostate, colon cancer, melanoma glioblastoma, endometrial carcinoma, hepatocellular cancer, lung cancer, renal cell carcinoma, thyroid carcinoma, cell lymphoma, lymphoproliferative disorders, small cell lung cancer, squamous cell lung carcinoma, glioma, ovarian cancer, cervical cancer, and leukemia.

In another aspect, the present invention relates to methods of treating cancer comprising administering to a patient in need thereof a therapeutically effective amount of an antibody to GM3NPhAc, sTnNPhAc, GD3NPhAc, GM2NPhAc, GD2NPhAc, sLe$^x$NPhAc, or fucosyl GM1NPhAc; and a therapeutically effective amount of compound of formula IV. In certain embodiments, the antibody is a monoclonal antibody. In particular embodiments, the patient is a human.

DEFINITIONS

As used herein, the following terms have the meanings ascribed to them unless specified otherwise.

"Lipid A" is a hydrophobic domain of a lipopolysaccharides (LPS) of the outer membranes of Gram-negative bacteria. The structure of a Lipid A molecule comprises a β-1,6-linked di-glucosamine with 1,4'-di-O-phosphorylation and 2,2'-N- and 3,3'-O-acylation (See Examples of Lipid A molecules in Table 1 herein).

A "monophosphorylated lipid A" ("MPLA") is a 4'-O-monophosphorylated Lipid A molecule, such as those MPLA molecules identified as such in Table 1 herein.

The term "alkyl group" or "alkyl" includes straight and branched carbon chain radicals. For example, a "$C_{1-6}$ alkyl" is an alkyl group having from 1 to 6 carbon atoms. Examples of $C_1$-$C_6$ straight-chain alkyl groups include, but are not limited to, methyl, ethyl, n-propyl, n-butyl, n-pentyl, and n-hexyl. Examples of branched-chain alkyl groups include, but are not limited to, isopropyl, tert-butyl, isobutyl, etc. Examples of alkylene groups include, but are not limited to, —$CH_2$—, —$CH_2$—$CH_2$—, —$CH_2$—$CH(CH_3)$—$CH_2$—, and —$(CH_2)_{1-3}$. Alkylene groups can be substituted with groups as set forth below for alkyl.

The term alkyl includes both "unsubstituted alkyls" and "substituted alkyls," the latter of which refers to alkyl moieties having substituents replacing a hydrogen on one or more carbons of the hydrocarbon backbone (e.g., 1 to 5 substituents, 1 to 3 substituents, etc.). Such substituents are independently selected from the group consisting of: halo (I, Br, Cl, F), —OH, —COOH, trifluoromethyl, —$NH_2$, —$OCF_3$, and O—$C_1$-$C_3$ alkyl.

Typical substituted alkyl groups thus are 2,3-dichloropentyl, 3-hydroxy-5-carboxyhexyl, 2-aminopropyl, pentachlorobutyl, trifluoromethyl, methoxyethyl, 3-hydroxypentyl, 4-chlorobutyl, 1,2-dimethyl-propyl, and pentafluoroethyl.

"Halo" includes fluoro, chloro, bromo, and iodo.

Some of the compounds in the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

The term "antibody" refers to a monomeric (e.g., single chain antibodies) or multimeric polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term "antibody" also includes antigen-binding polypeptides such as Fab, Fab', F(ab')$_2$, Fd, Fv, dAb, and complementarity determining region (CDR) fragments, single-chain antibodies (scFv), chimeric antibodies, and diabodies. The term antibody includes polyclonal antibodies and monoclonal antibodies unless otherwise indicated.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The amino terminus of each chain defines a variable region of about 100 to 110 or more amino acids primarily responsible for antigen recognition. The terms variable light chain ($V_L$) and variable heavy chain ($V_H$) refer to these light and heavy chains respectively.

As used herein, an Fd fragment means an antibody fragment that consists of the $V_H$ and $C_H1$ domains; an Fv fragment consists of the $V_L$ and $V_H$ domains of a single arm of an antibody; and a dAb fragment (Ward et al., *Nature* 341:544-546 (1989)) consists of a $V_H$ domain.

In some embodiments, the antibody is a single-chain antibody (scFv) in which a $V_L$ and $V_H$ domains are paired to form a monovalent molecule via a synthetic linker that enables them to be made as a single protein chain. (Bird et al., *Science* 242:423-426 (1988) and Huston et al., *Proc. Natl. Acad. Sci. USA* 85:5879-5883 (1988).) In some embodiments, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. (See e.g., Holliger P. et al., *Proc. Natl. Acad. Sci. USA* 90: 6444-6448 (1993), and Poljak R. J. et al., *Structure* 2:1121-1123 (1994)).

An antibody to a TACA (e.g., GM3NPhAc, sTnNPhAc, GD3NPhAc, GM2NPhAc, GD2NPhAc, sLe$^x$NPhAc, or fucosyl GM1NPhAc) is an antibody that specifically binds a TACA.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide antigen, refers to a binding reaction that is determinative of the presence of a specified protein. Typically, an antibody specifically binds an antigen when it has a $K_d$ of at least about 1 µM or lower, more usually at least about 0.1 µM or lower, and preferably at least about 10 nM or lower for that antigen.

A variety of immunoassay formats (e.g., Western blots, ELISAs, etc.) may be used to select antibodies specifically immunoreactive with a particular protein. For example, solid-phase ELISA immunoassays are routinely used to select antibodies specifically immunoreactive with a protein (see, e.g., Harlow and Lane, *Antibodies: A Laboratory Manual*, New York: Cold Spring Harbor Press, (1990) for a description of immunoassay formats and conditions that can be used to determine specific immunoreactivity).

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
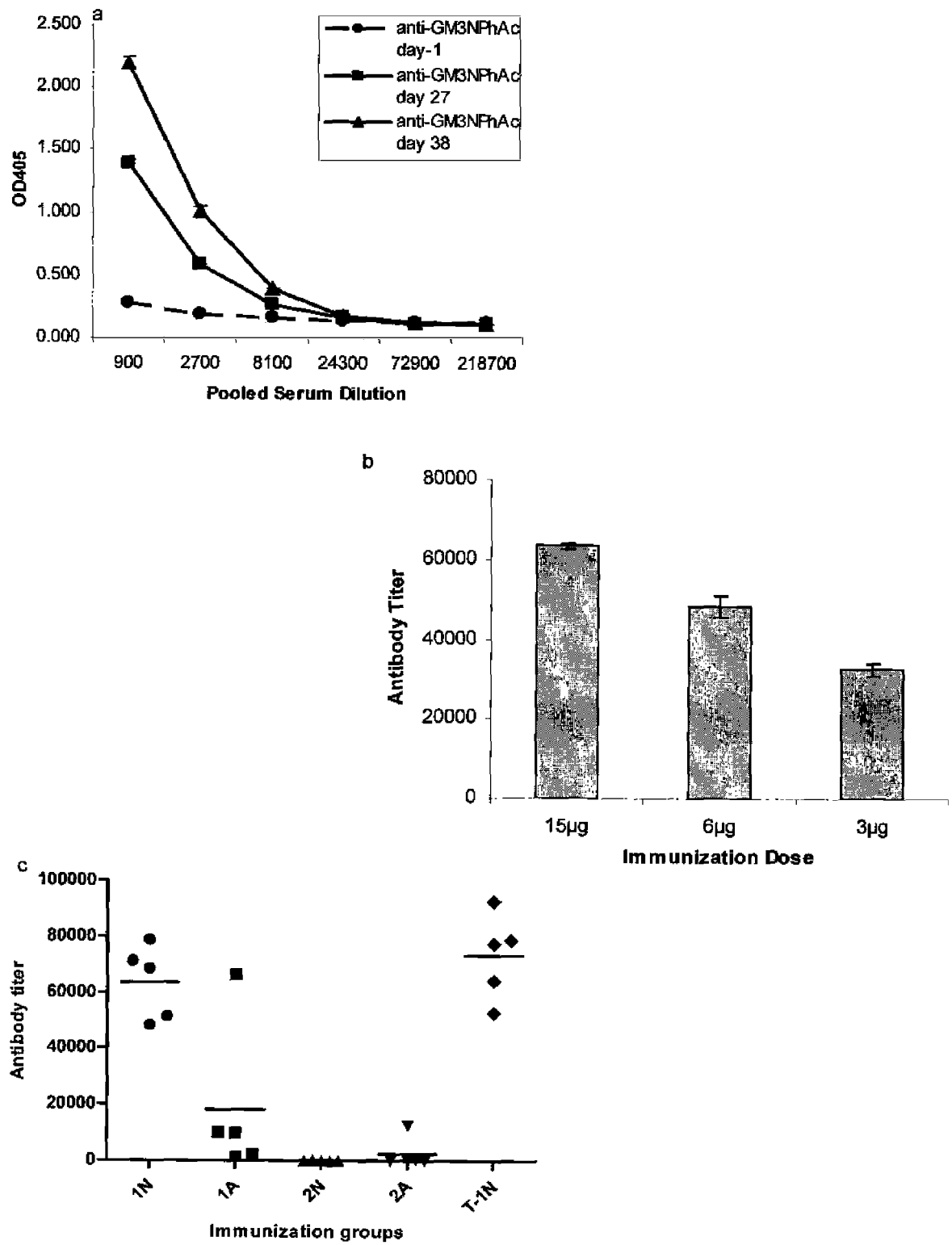
FIG. 1 relates to the ELISA analysis of GM3NPhAc-specific immune responses in mice. For ELISA assays, GM3NPhAc-HSA was used as the capture antigen. Goat anti-mouse kappa antibodies were used to detect antibodies bond to the capture antigen. Titers are determined by linear regression analysis and defined as the highest dilution yielding an optical density of 0.2. (a) GM3NPhAc-specific total antibody contents in day −1, 27 and 38 mice sera. Mice were immunized with 1N containing 15 µg of GM3NPhAc. Each line represents the antibody level in serum pooled from a group of five mice. (b) Comparison of GM3NPhAc-specific total antibody titers in day 38 mice sera. Mice were immunized with 1N containing 15, 6 or 3 µg of GM3NPhAc. (c) Comparison of immunological results of conjugates 1, 2 and T-1. 1N: conjugate 1 alone; 1A: conjugate 1+an external adjuvant; 2N: conjugate 2 alone; 2A: conjugate 2+an external adjuvant; T-1N: conjugate T-1 alone. Each dot represents the GM3NPhAc-specific immune response of individual mouse and the black lines represent the average antibody level of a group of five mice.

The following description is merely exemplary in nature and is in no way intended to limit the present disclosure or its application or uses.

I. Introduction

In one aspect the present invention relates to cancer vaccines using compounds of and pharmaceutical compositions comprising one or more compounds of Formulas I-IV.

In certain embodiments, the vaccine based on conjugate of a unnatural analog of a TACA (e.g., GM3NPhAc, sTnNPhAc, GD3NPhAc, GM2NPhAc, GD2NPhAc, sLe$^x$NPhAc, or fucosyl GM1NPhAc) to a MPLA (e.g., a compound of Formula I) which is administered in a therapeutically effective amount to one or more cancer patients to immunize them against the compound of formula I. Once an immune response for the TACA conjugate is established, the patients would typically be administered a therapeutically effective amount of modified sugar (e.g., a compound of formula IV) as a biosynthetic precursor of this unnatural TACA analog to induce its expression in place of the natural TACA on the cancer cell surface. Subsequently, the pre-provoked immune system will recognize and eradicate the tumor cells which express the unnatural TACA analog.

The cancer immunotherapy can also be achieved by a passive immunization protocol. First, patients are treated with an unnatural TACA precursor (e.g., a compound of formula IV) to induce the expression of the unnatural TACA analog on cancer cells. Meanwhile, a healthy individual is immunized with the synthetic vaccine made of the unnatural TACA analog for the preparation of specific antibodies, which will be then co-adminstered with the synthetic sugar precursor for treatment of cancer patients.

II. Preparation of Compounds

Compounds of the present invention (e.g., compounds of Formulas I-IV) can be prepared by applying synthetic methodology known in the art and synthetic methods outlines in the schemes below.

The synthesis of compounds of formula I may be carried out as exemplified by the schemes set out below for the synthesis of 1 in Schemes 1-2.

Scheme 1 Synthesis of 3

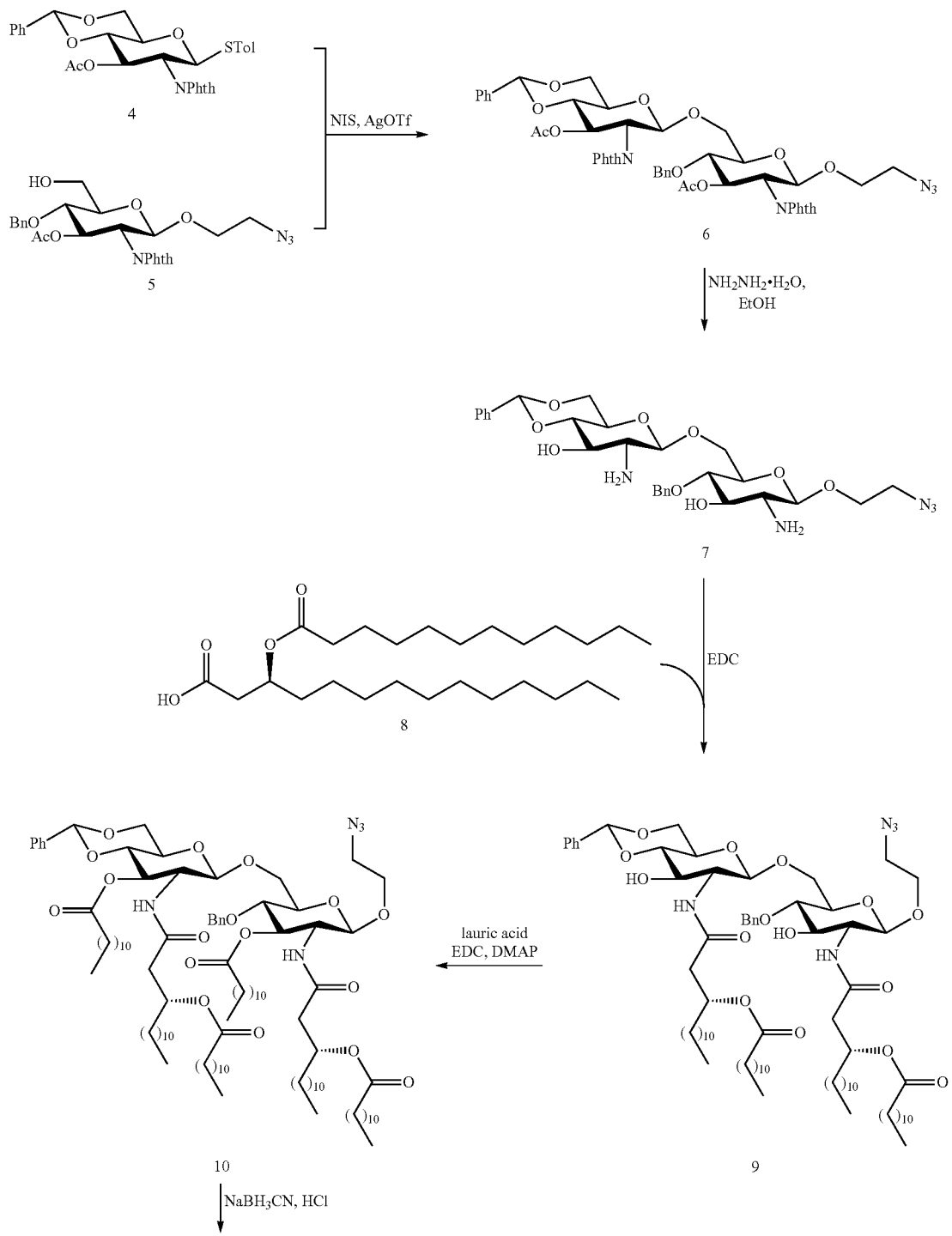

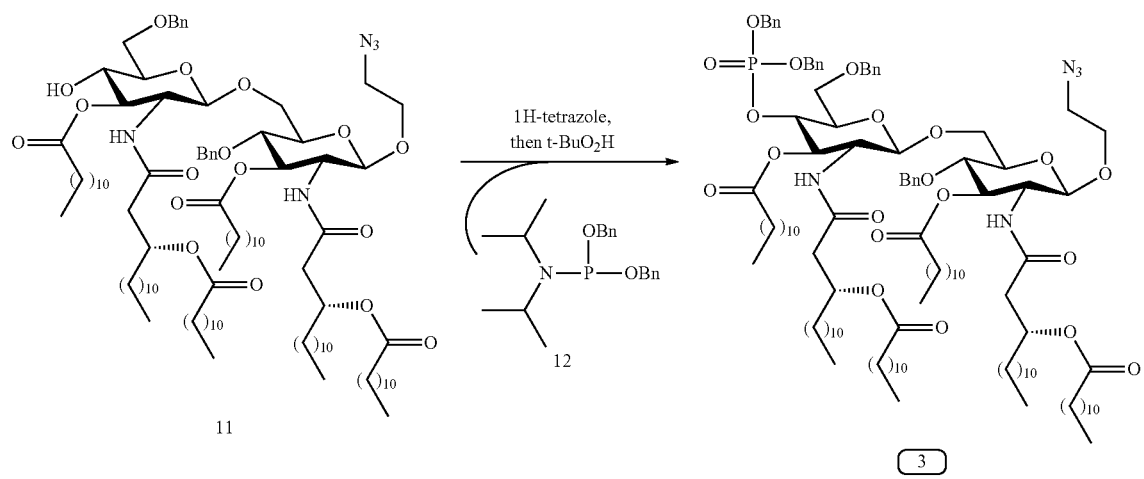

The synthesis of 3 is outlined in Scheme 1. Monosaccharide blocks 4 and 5 may be synthesized from commercially available glucosamine following a series of established transformations. The glycosylation reaction between 4 and 5 can be achieved with N-iodosuccinimide (NIS) and silver trifluoromethanesulfonate (AgOTf) as promoters at room temperature for about 2 days, to afford the desired β-anomer 6 ($J_{1',2'}$=8.8 Hz). Then, the phthalyl and acetyl groups in 6 may be simultaneously removed upon treatment with hydrazine in refluxing ethanol to give 7. Selective acylation of the free amino groups of 7 by (R)-3-dodecanoyl-tetradecanoic acid 8 using 1-ethyl-3-(3-dimethylaminopropyl)carbodiimide (EDC) as the condensation reagent may be accomplished to furnish 9. Acylation of both C-3 and C-3' hydroxyl groups of 9 by lauric acid may require a high temperature (45° C.) to produce 10. Thereafter, regioselective opening of the benzylidene acetal ring of 10 can be accomplished using sodium cyanoborohydride ($NaCNBH_3$) and HCl in dry diethyl ether to produce 11, which has a free hydroxyl group on C-4', and the regiochemistry can be confirmed via an acetylation experiment. Finally, 11 may be phosphorylated in a two-step-one-pot manner to afford the synthetic target 3.

Scheme 2 Synthesis of 1

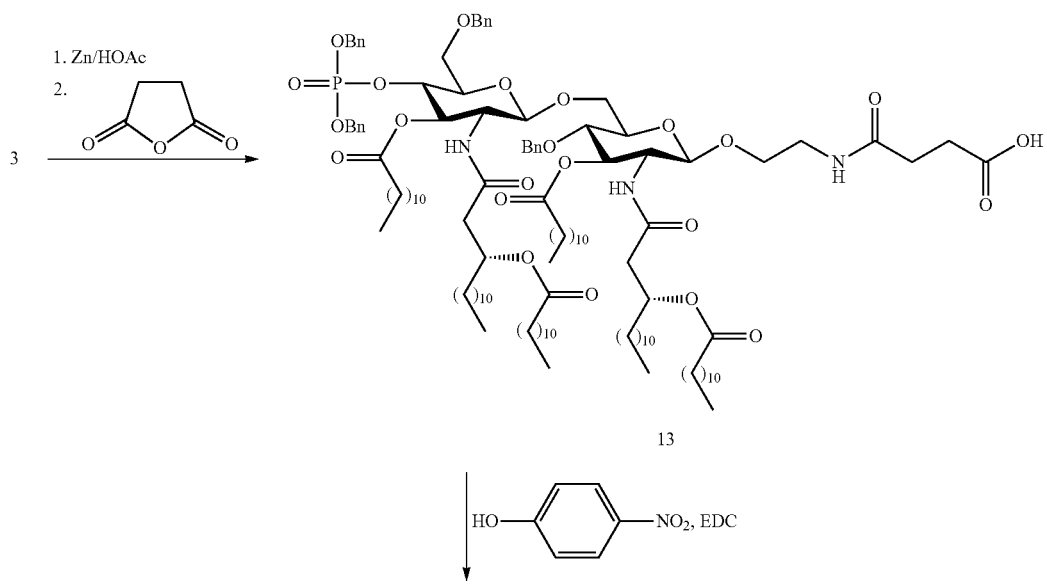

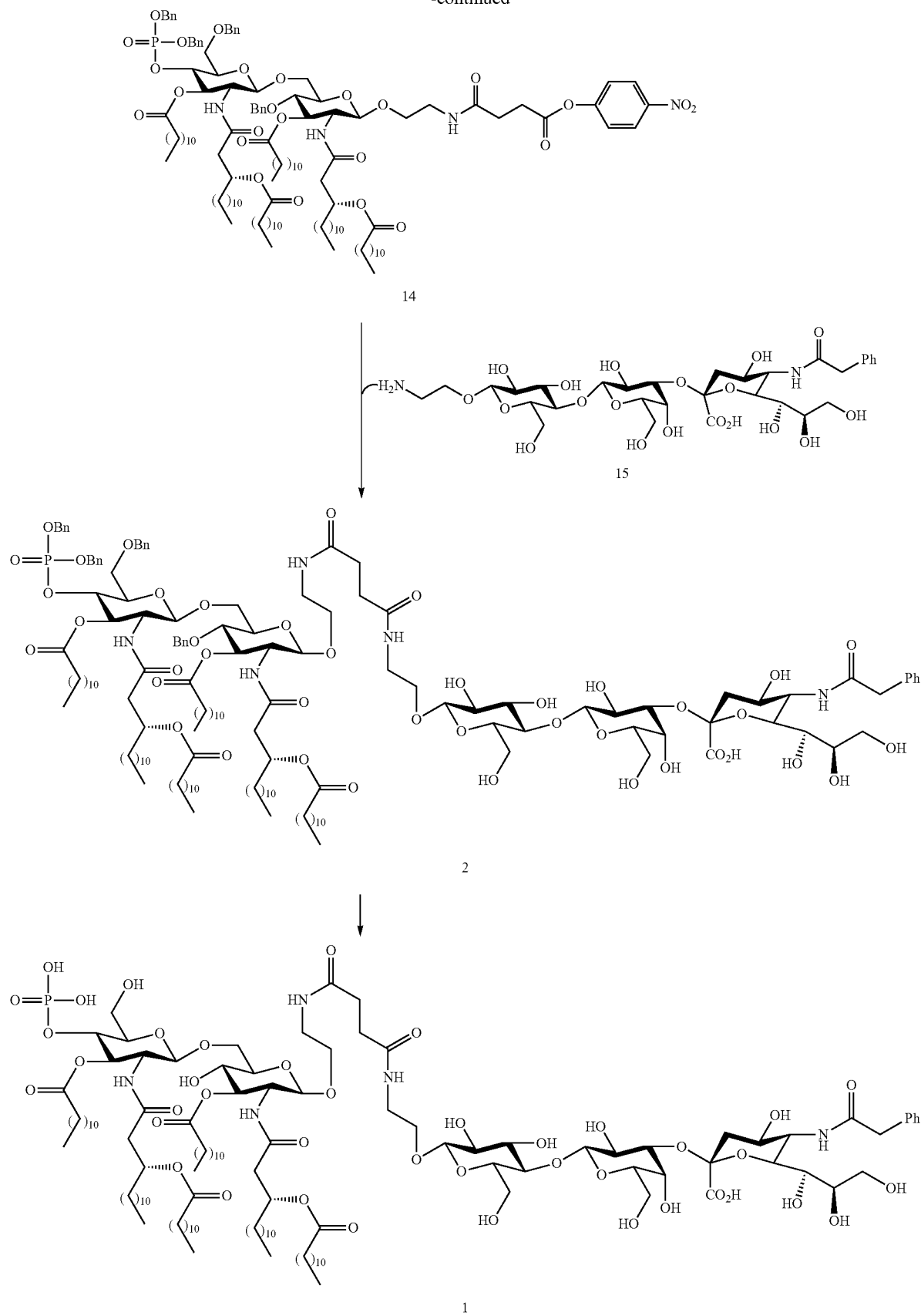
-continued

Compound 1 may be provided as set out in Scheme 2. The azido group of 3 may be reduced with Zn under acidic conditions, and the resultant free amine may be acylated with succinic anhydride to form 13. The compound 13 can be then transformed into the active ester 14 to facilitate the coupling to 15. The reaction between 14 and 15 afforded the desired 2 in a good yield. 2 may be readily deprotected via Pd-catalyzed hydrogenolysis to provide 1.

The synthesis of compounds of formula II may be carried out as exemplified by the schemes set out below for the synthesis of S-1 in Schemes S1-S5.

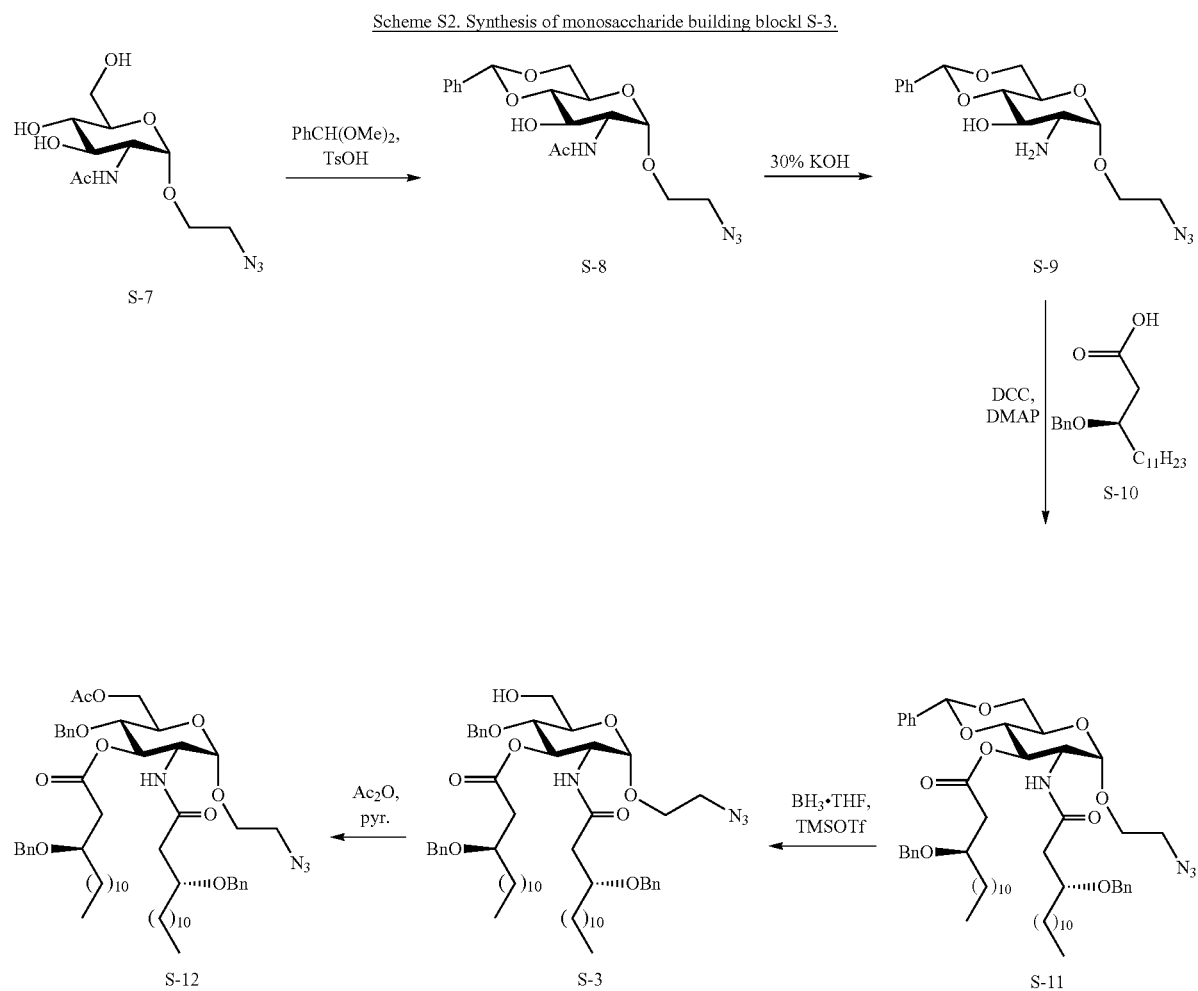

The synthesis of the monosaccharide building block S-2 may be prepared using Scheme S1. The compound 4 may be prepared from glucosamine using a series of established transformations, (Y. Zhang et al., *Bioorg. Med. Chem.* (2007), 15, 4800); Niu et al., *Synlett* (2007), 2116). The phthaloyl group and the acetyl group protecting the 2-N- and 3-O- positions of 4, respectively, may be removed by treatment with ethylene diamine, followed by regioselective protection of the free amino group by Troc to achieve S-5. The lipidation of S-5 by means of (R)-3-tetradecanoyloxy-tetradecanoic acid S-6 may be accomplished with N,N'-dicyclohexylcarbodiimide (DCC) as the condensation reagent to afford building block S-2.

Scheme S2. Synthesis of monosaccharide building block S-3.

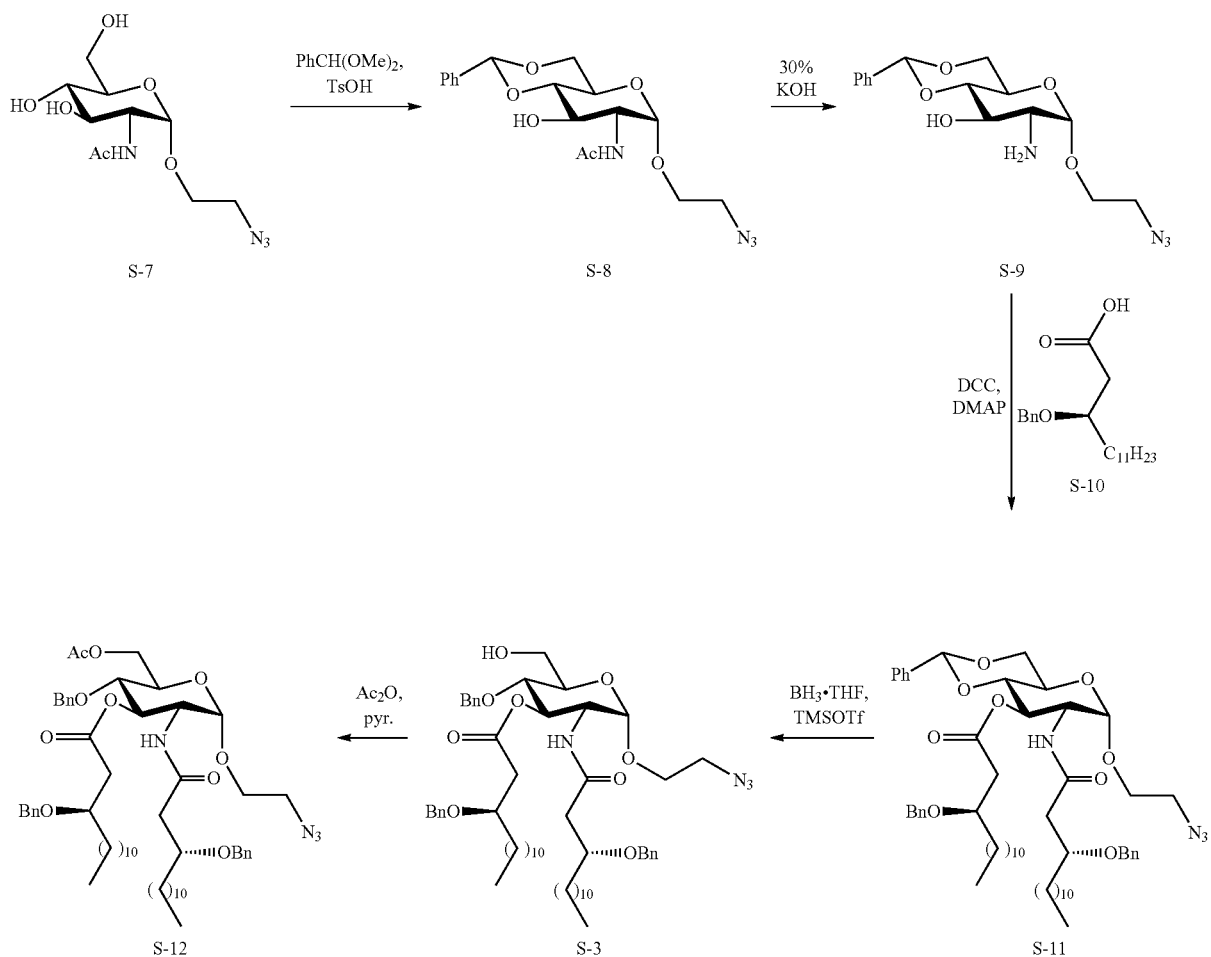

The synthesis of S-3 (Scheme S2) may begin with the preparation of S-7 by a reported procedure (Roy et al., *Tetrahedron* (2003), 59, 3881). The 4,6-O-positions of S-7 may then be selectively protected with a benzylidene group, followed by deacetylation of the amino group under basic conditions to provide S-9. The amino and hydroxyl groups of S-9 may be simultaneously acylated by (R)-3-benzyloxy-tetradecanoic acid S-10 to yield S-11, again, with DCC as a condensation reagent. The benzylidene acetal ring may be thereafter opened regioselectively with borane as the reducing reagent and trimethylsilyl triflate (TMSOTf) as the catalyst to afford building block S-3. The regiochemistry of S-3 may be confirmed by acetylation of S-3 to provide 5-12, which would have downfield-shifted NMR signals of H-6a,6b.

Scheme S3. Synthesis of the target MPLA derivative S-18.

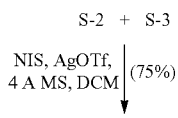

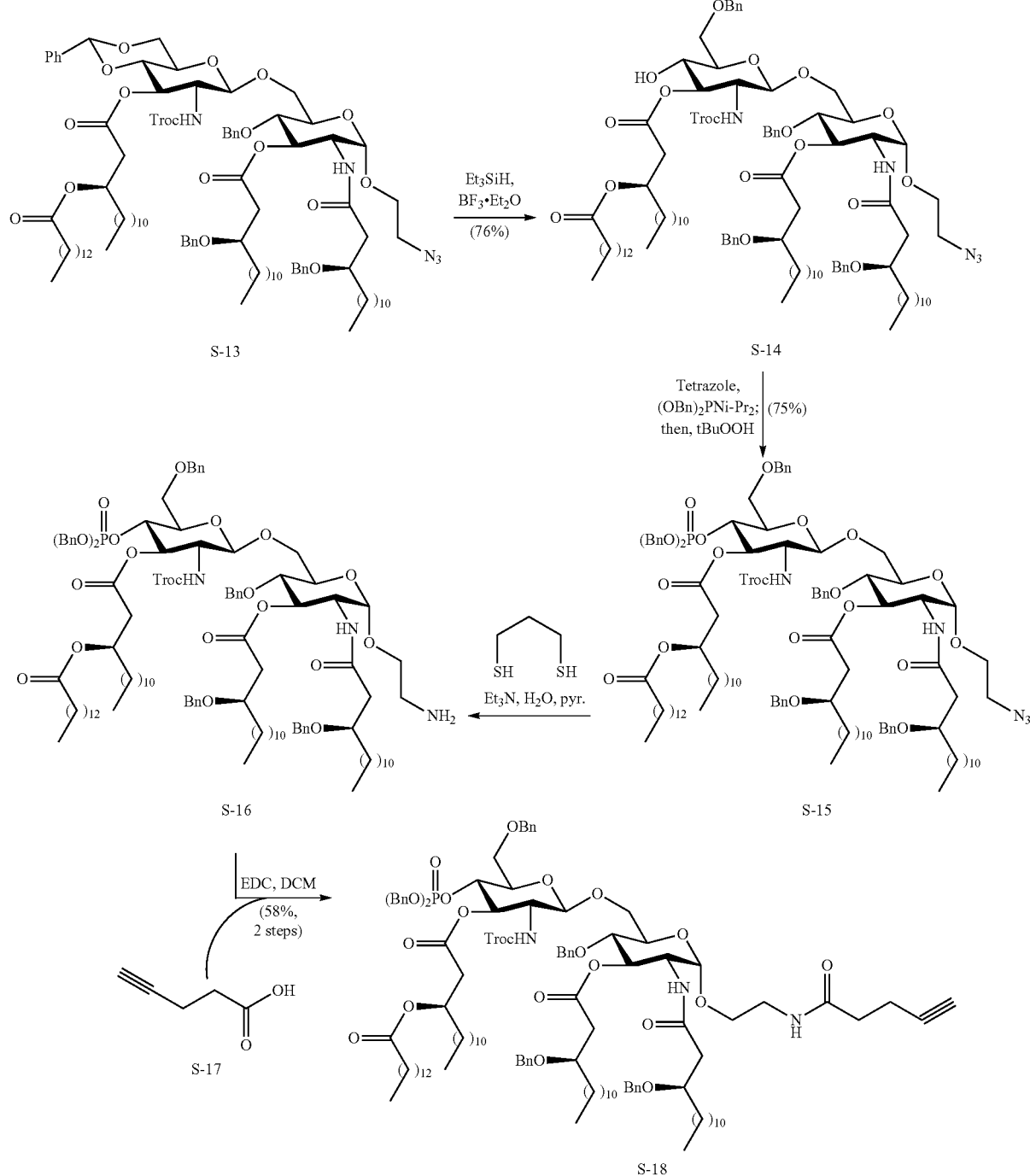

For the assembly of S-18 (Scheme S3), S-3 can be glycosylated by S-2 using N-iodosuccinimide (NIS) and silver triflate (AgOTf) as the promoters. This reaction is typically stereoselective to afford the desired β-anomer only of S-13. For the regioselective opening of the benzylidene acetal ring of S-13, sodium cyanoborohydride (NaCNBH$_3$/HCl (g)) was not productive. The regioselective ring opening may, however, be accomplished using triethylsilane (Et$_3$SiH) and boron trifluoride etherate (BF$_3$ OEt$_2$) to expose the C-4' hydroxyl group providing S-14. The regiochemistry of the product S-14 may be confirmed by an acetylation experiment, which results downfield shift of the NMR signal of its H-4'. Next, S-14 can be phosphorylated by a two-step-one-pot protocol with dibenzyl phosphoramidite and t-BuO$_2$H as the phosphorylating and oxidizing reagents, respectively, to furnish S-15. The alkyne functionality can be introduced at this stage. Thus, the azido group of S-15 may be reduced by propane-1,3-dithiol, and the free amine S-16 was acylated with 4-pentynoic acid S-17 using 1-ethyl-3-(3-dimethylaminopropyl)-carbodiimide (EDC) hydrochloride as the condensation reagent. The use of phosphine or Lindlar catalyst/H$_2$ to reduce S-15 was slow and inefficient.

Scheme S4 Synthesis of the S-21.
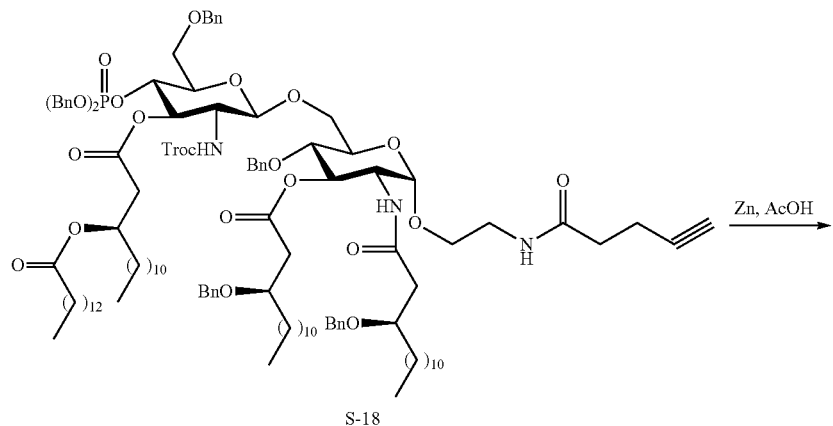
S-18
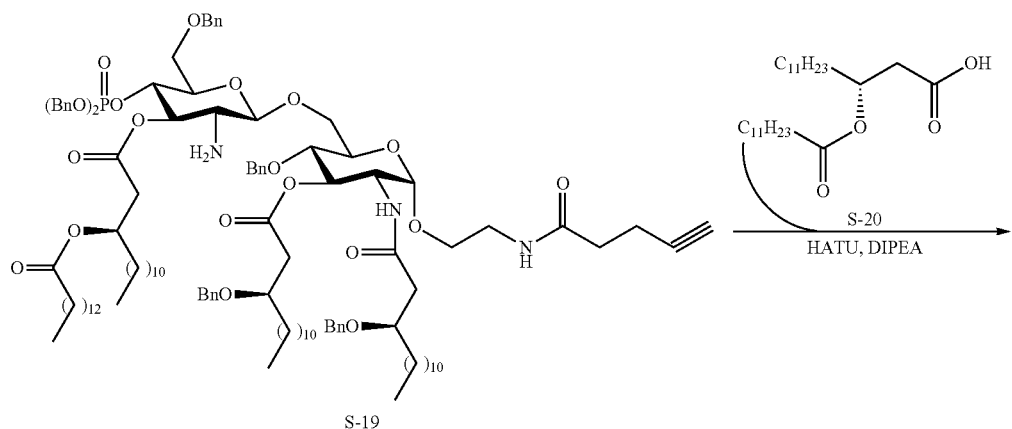
S-19
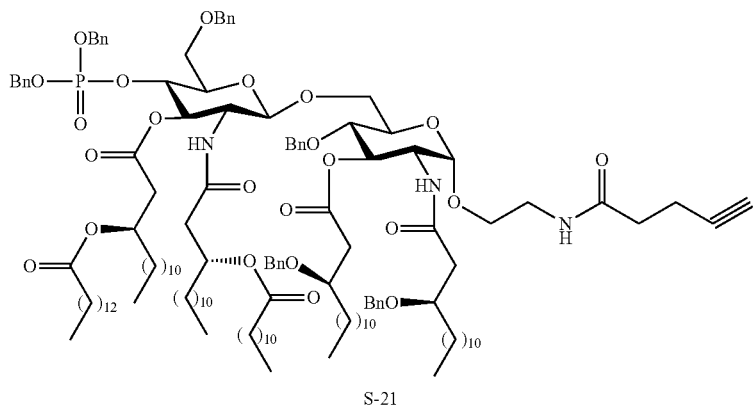
S-21
The compound S-21 may be provided using Scheme S4. The Troc group of S-18 may be removed by treatment with Zn in AcOH, followed by N-acylation of S-19 by (R)-3-dodecanoyloxy-tetradecanoic acid S-20 with 2-(7-aza-1H-benzotriazole-1-yl)-1,1,3,3-tetramethyluronium hexafluorophos-phate (HATU)/N,N-diisopropylethylamine (DIPEA) as condensation reagents to afford the S-21.

Scheme S5. Coupling S-21 and GM3NPhAc by click chemistry to afford S-1.

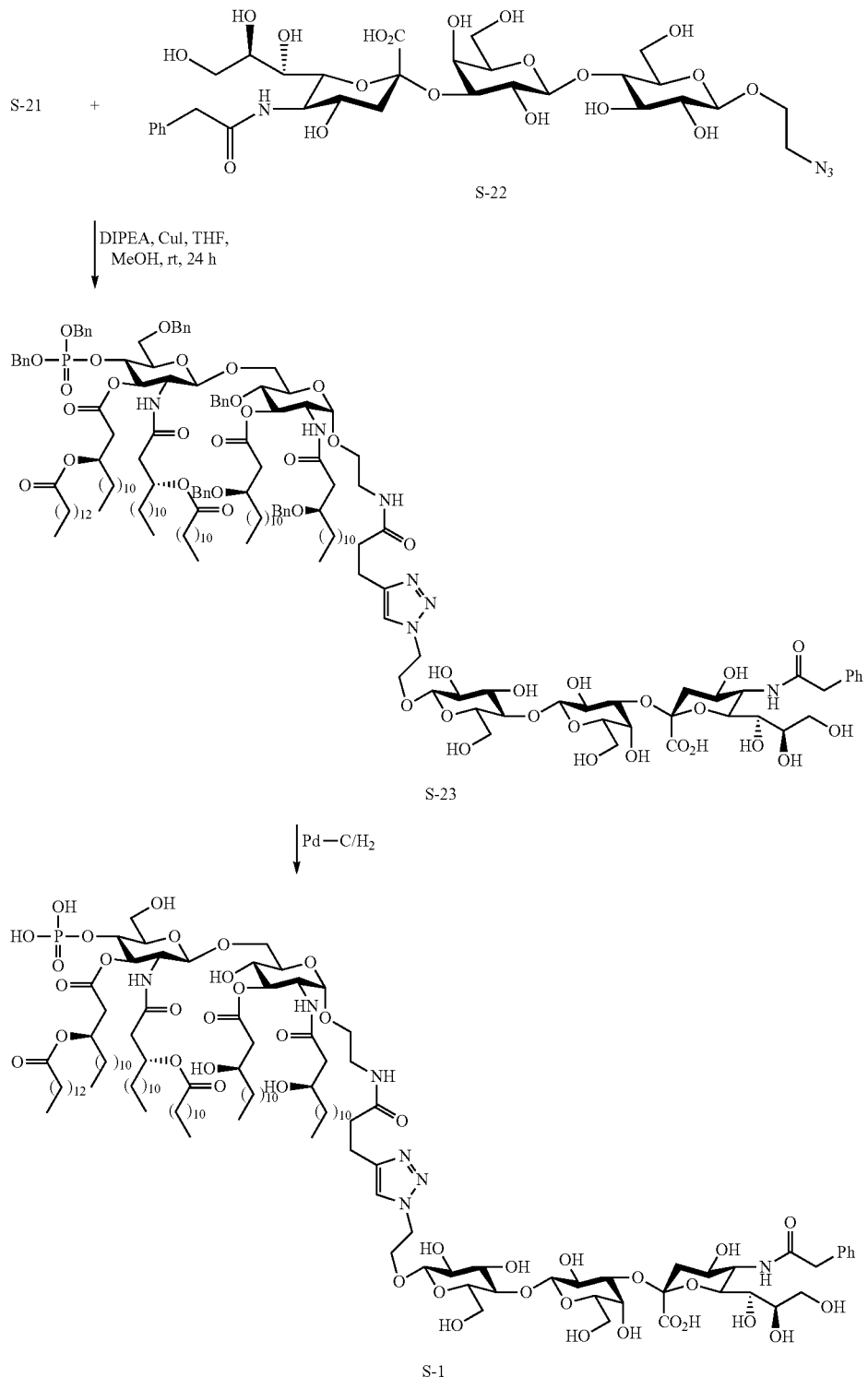

The compound S-1 may be synthesized using Scheme S5. The reaction between S-21 and S-22 may be accomplished using a click reaction (Kolb et al., *Angew. Chem. Int. Ed.* 2001, 40, 2004) (Scheme S5). The compounds S-21 and S-22 may be reacted in the presence of CuI/DIPEA in a MeOH/THF mixture to yield the MPLA-GM3NPhAc conjugate S-23. The deprotection of S-23 to provide S-1 may be accomplished using Pd-catalyzed hydrogenolysis.

The synthesis of compounds of formula III may be carried out as exemplified by the schemes set out below for the synthesis of T-1 in Scheme T1.

Scheme T1. Synthetic route to T-1
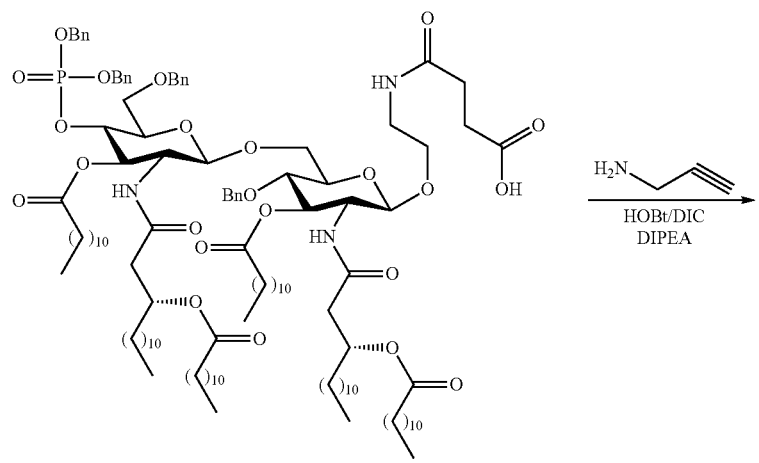
13
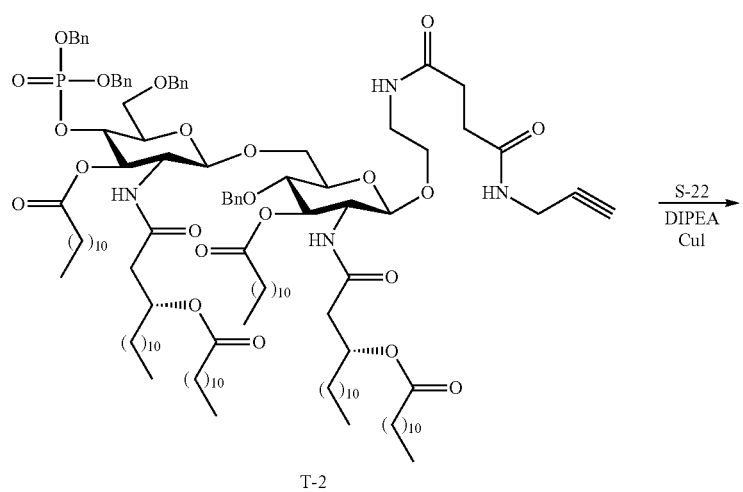
T-2
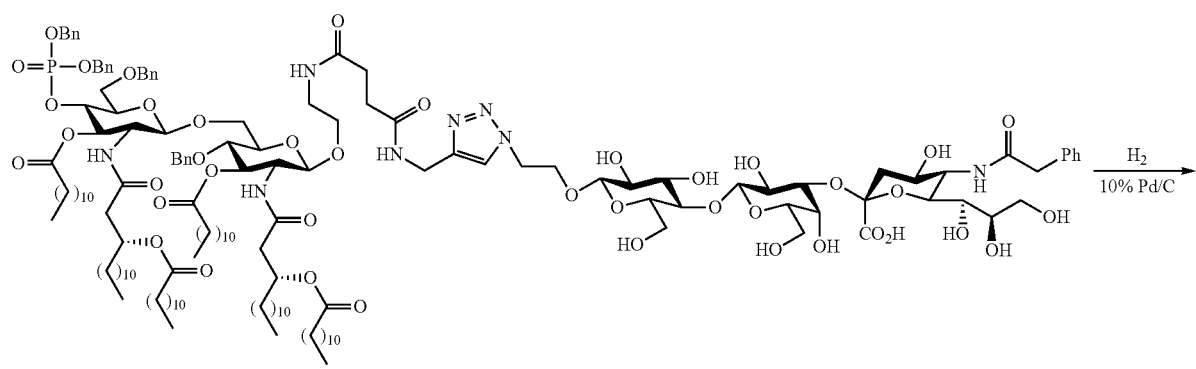
T-3

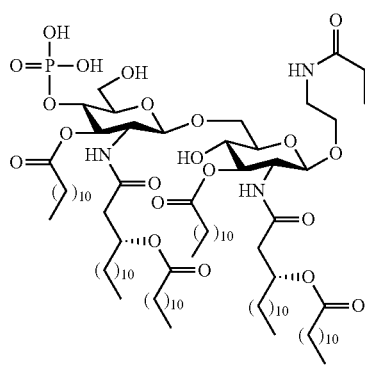
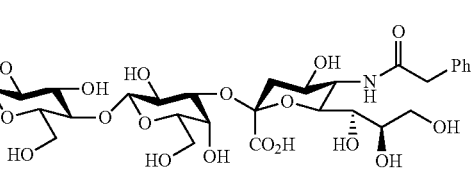

T-1

The compound T-1 may be synthesized using Scheme T1. Introduction of a alkyne functionality to 13 may be completed by reaction of 13 with propargylamine using N-Hydroxybenzotriazole (HOBt) and diisopropylcarbodiimide (DIC) as condensation reagent. The compound T-2 may be reacted with S-22 in the presence of CuI/DIPEA in a MeOH/THF mixture to yield T-3. The deprotection of T-3 to provide T-1 may be accomplished using Pd-catalyzed hydrogenolysis.

The synthesis of compounds of formula IV may be carried out by the scheme U1 set out below.

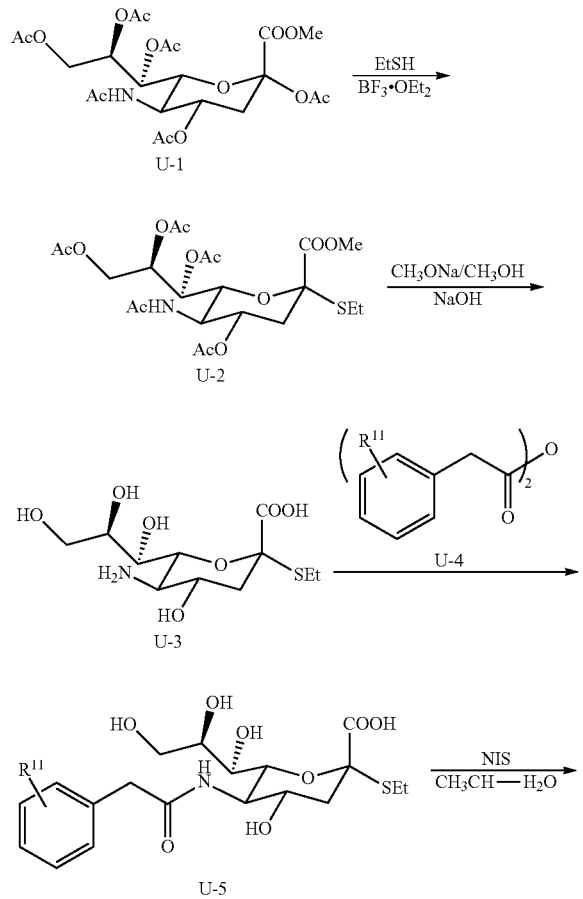

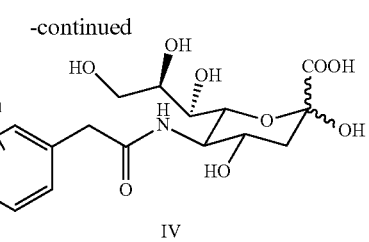

IV

The N-acylsialic acid U-1 (Pan et al. (2004) Carbohydrate Res. 339: 2091-2100) may be reacted with ethanethiol in the presence of boron trifluoride etherate ($BF_3$ $OEt_2$) to provide the thioether U-2. The compound U-2 can then be deprotected with sodium methoxide/methanol (NaOMe/MeOH) and sodium hydroxide (NaOH) to provide U-3. The compound U-3 is then reacted with the derivatized phenylacetic anhydride U-4 to provide U-5. For U-4, $R_{11}$ represents H or is one or two substituents selected from the group consisting of: $C_1$-$C_6$ alkyl, —$OC_1$-$C_4$ alkyl, $C(O)C_1$-$C_4$ alkyl, or halo. U-5 may be transformed into IV using N-iodosuccinimide(NIS)/$H_2O$.

In another aspect, the present invention relates to anti-TACA antibodies and their administration with one or more compounds of formula IV to treat cancers. Anti-TACA antibodies may be provided as described herein. For preparation of anti-TACA monoclonal or polyclonal antibodies, techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985)). In addition, phage display technology can be used to identify single chain antibodies and heteromeric Fab fragments that specifically bind to selected antigens (see, e.g., McCafferty et al, Nature 348:552-554 (1990); Marks et al., Biotechnology 10:779-783 (1992)). Typically TACAs are employed to generate TACA antibodies, respectively. Polyclonal antibodies typically can be generated by immunization of an animal with the antigen of choice. The immunization of the animals can be by any method known in the art (see, e.g., Harlow and Lane, *Antibodies: A Laboratory Manual*, New York: Cold Spring Harbor Press, 1990). Methods for immunizing non-human animals such as mice, rabbits, rats, sheep, goats, pigs, cattle and horses are well known in the art (see, e.g., Harlow and Lane, supra, and U.S. Pat. No. 5,994,619).

In certain embodiments, a TACA antigen is administered with an adjuvant to stimulate the immune response. Exemplary adjuvants include complete or incomplete Freund's adjuvant, RIBI (muramyl dipeptides) or ISCOM (immunostimulating complexes). Preferably, if a polypeptide is being administered, the immunization schedule will involve two or more administrations of the polypeptide, spread out over several weeks.

After immunization of an animal with a TACA antigen, polyclonal antibodies and/or antibody-producing cells can be obtained from the animal. In some embodiments, anti-TACA antibody-containing serum is obtained from the animal by bleeding or sacrificing the animal. The serum may be used as it is obtained from the animal, an immunoglobulin fraction may be obtained from the serum, or the anti-TACA antibodies may be purified from the serum.

The animal's immune response to an immunogen preparation can be monitored by taking test bleeds and determining the titer of reactivity to the protein of choice. When appropriately high titers of antibody to the immunogen are obtained, blood can be collected from the animal and antisera are prepared. The level of TACA antibodies in serum can be assayed using a TACA immunoassay. The polyclonal antibodies can be purified from the serum of an immunized animal using standard antibody and protein purification techniques.

Monoclonal antibodies can also be prepared against TACAs. In certain embodiments, hybridoma techniques can be used to generate monoclonal antibodies. For example, antibody-producing immortalized cell lines can be prepared from cells isolated from the immunized animal. After immunization, the animal is sacrificed and lymph node and/or splenic B cells are immortalized. Methods of immortalizing cells include, but are not limited to, transfecting them with oncogenes, infecting them with an oncogenic virus, cultivating them under conditions that select for immortalized cells, subjecting them to carcinogenic or mutating compounds, fusing them with an immortalized cell, e.g., a myeloma cell, and inactivating a tumor suppressor gene (see, e.g., Harlow and Lane, supra). If fusion with myeloma cells is used, the myeloma cells preferably do not secrete immunoglobulin polypeptides (a non-secretory cell line).

Immortalized cells can be screened using TACAs, or portions thereof, or a cell expressing TACAs. In certain embodiments, the initial screening can be performed using an enzyme-linked immunoassay (ELISA) or a radioimmunoassay.

In some embodiments, human antibodies are produced by immunizing a non-human animal comprising in its genome some or all of human immunoglobulin heavy chain and light chain loci with a TACA antigen. In certain embodiments, the non-human animal can be a XENOMOUSE™ animal (Abgenix Inc., Fremont, Calif.). Another non-human animal that may be used is a HuMAb-Mouse®, a transgenic mouse produced by Medarex (Medarex, Inc., Princeton, N.J.).

XENOMOUSE™ mice are engineered mouse strains that comprise large fragments of human immunoglobulin heavy chain and light chain loci and are deficient in mouse antibody production (see, e.g., Green et al., *Nature Genetics* 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584). The splenic B cells from a XENOMOUSE™ can be fused to a non-secretory mouse myeloma (e.g, the myeloma cell line P3-X63-AG8-653) and monoclonal antibodies may be identified from the resulting pool of hybridomas. The TACA antibodies secreted by a hybridoma may be purified from a hybridoma culture and used in the methods of the present invention. The nucleic acids encoding the heavy and light chains of the TACA antibody may be isolated from a hybridoma and expressed in a host cell, e.g., NSO cells, CHO cells etc., to provide a source material from which purified TACA antibodies may be obtained.

In another embodiment, a transgenic animal is immunized with TACA, primary cells, e.g., spleen or peripheral blood cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable region sequences, e.g., degenerate primers that recognize most or all of the FR1 regions of human heavy and light chain variable region genes and anti-sense primers that anneal to constant or joining region sequences. The cDNAs of the heavy and light chain variable regions are then cloned and expressed in any suitable host cell, e.g., a myeloma cell, as chimeric antibodies with respective immunoglobulin constant regions, such as the heavy chain and K or A constant domains (see Babcook, J. S. et al., *Proc. Natl. Acad. Sci. USA* 93:7843-48, 1996, herein incorporated by reference). Anti TACA antibodies may then be identified and isolated as described herein.

In another aspect, the invention provides a method for making humanized anti-TACA antibodies. In some embodiments, rats or mice are immunized with a TACA antigen as described below under conditions that permit antibody production. Antibody-producing cells are isolated from the animals, fused with myelomas to produce hybridomas, and nucleic acids encoding the heavy and light chains of an anti-TACA antibody of interest are isolated. These nucleic acids are subsequently engineered using techniques known to those of skill in the art and as described further below to reduce the amount of non-human sequence, i.e., to humanize the antibody to reduce the immune response in humans In another embodiment, phage display techniques can be used to provide libraries containing a repertoire of antibodies with varying affinities for TACA. By way of example, one method for preparing the library of antibodies for use in phage display techniques comprises the steps of immunizing a non-human animal comprising human immunoglobulin loci with an TACA to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. The resulting phage are tested for immunoreactivity to an TACA antigen. Recombinant TACA antibodies of the invention may be obtained in this way.

Techniques for the identification of high affinity human antibodies from such libraries are described for example in U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nuc. Acid Res.* 19:4133-4137 (1991); and Barbas et al., *Proc. Natl. Acad. Sci. USA* 88:7978-7982 (1991).

There are commercially available kits for generating phage display libraries (e.g., the Pharmacia Recombinant Phage Antibody System, catalog no. 27-9400-01; and the Stratagene SurZAP™ phage display kit, catalog no. 240612) as well as commercially available systems for producing fully human phage expressed antibodies such as Cambridge Antibody Technology PLC (Cambridge, United Kingdom) and MorphoSys AG (e.g., HuCAL® GOLD technology, Martinsried, Germany).

Following screening and isolation of an anti-TACA antibody from a recombinant immunoglobulin display library, nucleic acids encoding the selected antibody can be recovered from the display package (e.g., from the phage genome) and subcloned into other expression vectors by standard recombinant DNA techniques. For example, the DNA encoding a phage expressed antibody can be cloned into a recombinant expression vector and introduced into a mammalian host cells or prokaryotic cells as appropriate for that antibody.

III. Pharmaceutically Acceptable Salts and Solvates

The compounds of formulas I-IV can exist in unsolvated forms as well as solvated forms, including hydrated forms. In general, the solvated forms, including hydrated forms, are equivalent to unsolvated forms and are intended to be encompassed within the scope of the present invention.

The compounds of the present invention (e.g., compounds of Formulas I-IV) are capable of further forming both pharmaceutically acceptable salts, including but not limited to acid addition and/or base salts. Pharmaceutically acceptable salts of the compounds of formula (I) include the acid addition and base salts (including disalts) thereof. Examples of suitable salts can be found for example in Stahl and Wermuth, *Handbook of Pharmaceutical Salts: Properties, Selection, and Use*, Wiley-VCH, Weinheim, Germany (2002); and Berge et al., "Pharmaceutical Salts," *J. of Pharmaceutical Science,* 1977; 66:1-19.

Pharmaceutically acceptable acid addition salts of the compounds of Formulas I-IV include non-toxic salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include the acetate, aspartate, benzoate, besylate (benzenesulfonate), bicarbonate/carbonate, bisulfate, caprylate, camsylate (camphor sulfonate), chlorobenzoate, citrate, edisylate (1,2-ethane disulfonate), dihydrogenphosphate, dinitrobenzoate, esylate (ethane sulfonate), fumarate, gluceptate, gluconate, glucuronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, mesylate (methanesulfonate), metaphosphate, methylbenzoate, methylsulfate, 2-napsylate (2-naphthalene sulfonate), nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, tosylate (toluene sulfonate), and xinafoate salts, and the like of compounds of Formulas I-IV. Also contemplated are the salts of amino acids such as arginate, gluconate, galacturonate, and the like.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are aluminum, calcium, magnesium, potassium, sodium, and the like. Examples of suitable amines include arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine), and tromethamine.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

IV. Pharmaceutical Compositions

Pharmaceutical Compositions of Compounds of Formulas I-IV

This invention also provides for pharmaceutical compositions comprising a therapeutically effective amount of a compound of Formulas I-IV, or a pharmaceutically acceptable salt thereof together with a pharmaceutically acceptable carrier, diluent, or excipient therefor. The phrase "pharmaceutical composition" refers to a composition suitable for administration in medical or veterinary use. The phrase "therapeutically effective amount" means an amount of a compound, or a pharmaceutically acceptable salt thereof, sufficient to inhibit, halt, or allow an improvement in the disorder or condition being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with a cancer as measured quantitatively or qualitatively.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane nitrogen, and the like.

Formulations suitable for parenteral administration, such as, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a subject, in the context of the present invention should be sufficient to affect a beneficial therapeutic response in the subject over time. The term "subject" refers to a member of the class Mammalia. Examples of mammals include, without limitation, humans, primates, chimpanzees, rodents, mice, rats, rabbits, horses, livestock, dogs, cats, sheep, and cows.

The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject. Many different administration methods are known to those of skill in the art.

For administration, compounds of the present invention can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

Pharmaceutical Compositions of Anti-TACA Antibodies

The invention also relates to pharmaceutical compositions comprising an anti-TACA antibody (e.g., an antibody to a compound of formula I) for the treatment of subjects in need of treatment for cancer. Treatment may involve administration of one or more anti-TACA monoclonal antibodies, alone or with a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, isotonic agents, for example, sugars, polyalcohols such as mannitol, sorbitol, or sodium chloride can be present in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The anti-TACA antibody compositions may be in a variety of forms, for example, liquid, semi-solid and solid dosage forms, such as liquid solutions (e.g., injectable and infusible solutions), dispersions or suspensions, tablets, pills, powders, liposomes and suppositories. The particular form depends on the intended mode of administration and therapeutic application. Typical compositions are in the form of injectable or infusible solutions, such as compositions similar to those used for passive immunization of humans.

Therapeutic compositions typically are sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-TACA antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation include vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the antibody composition may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., *Sustained and Controlled Release Drug Delivery Systems* (J. R. Robinson, ed., Marcel Dekker, Inc., New York, 1978)).

V. Methods for Treating Cancers

The compounds of the present invention and pharmaceutical compositions comprising a compound of the present invention can be administered to a subject suffering from a cancer. Cancers can be treated prophylactically, acutely, and chronically using compounds of the present invention, depending on the nature of the disorder or condition. Typically, the host or subject in each of these methods is human, although other mammals can also benefit from the administration of a compound of the present invention.

In one aspect, the present invention relates to the co-administration of a compound of formula I-III with compound of formula IV to treat a cancer. In particular embodiments, the compound of formula I-III is first administered to a patient to provoke an immune response, then a compound of formula IV is administered. The compound of formula I-III and the compound of formula IV may be administered at the same time or administered up to one day, one week, one to three months, one to 6 months, one year apart. In therapeutic applications, the compounds formulas I-IV can be prepared and administered in a wide variety of oral and parenteral dosage forms. The term "administering" refers to the method of contacting a compound with a subject. Thus, the compounds of the present invention can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of the present invention can be administered transdermally, topically, and via implantation. In certain embodiments, the compounds of the present invention are delivered orally. The compounds can also be delivered rectally, bucally, intravaginally, ocularly, andially, or by insufflation.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner.

Compounds of formulas I-IV can be co-administered with compounds that are useful for the treatment of cancer (e.g., cytotoxic drugs such as TAXOL®, taxotere, GLEEVEC® (Imatinib Mesylate), adriamycin, daunomycin, cisplatin, etoposide, a vinca alkaloid, vinblastine, vincristine, methotrexate, or adriamycin, daunomycin, cis-platinum, etoposide, and alkaloids, such as vincristine, farnesyl transferase inhibitors, endostatin and angiostatin, VEGF inhibitors, and antimetabolites such as methotrexate. The compounds of the present invention may also be used in combination with a taxane derivative, a platinum coordination complex, a nucleoside analog, an anthracycline, a topoisomerase inhibitor, or an aromatase inhibitor). Radiation treatments can also be co-administered with a compound of the present invention for the treatment of cancers.

In another aspect, a therapeutically effective amount of an anti-TACA antibody may be administered to a cancer patient in conjunction with a therapeutically effective amount of a compound of formula IV. A "therapeutically effective amount" refers to an amount, at dosages and for periods of time necessary, sufficient to inhibit, halt, or allow an improvement in the disorder or condition being treated when administered alone or in conjunction with another pharmaceutical agent or treatment in a particular subject or subject population. The term "patient" refers to a member of the class Mammalia. Examples of mammals include, without limitation, humans, primates, chimpanzees, rodents, mice, rats, rabbits, horses, dogs, cats, sheep, and cows. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that the determination of proper dosage forms, dosage amounts, and routes of administration is within the level of ordinary skill in the pharmaceutical and medical arts. A therapeutically effective amount of the antibody or compound of formula IV may vary according to factors such as the disease state, age, sex, and weight of the individual, and the ability of the antibody to elicit a desired response in the individual. A therapeutically effective amount is also one in which any toxic or detrimental effects of an agent are outweighed by the therapeutically beneficial effects.

The antibody or compound of formula IV may be administered once or multiple times. For example, the antibody or compound of formula IV may be administered from three times daily to once every six months or longer. The administering may be on a schedule such as three times daily, twice daily, once daily, once every two days, once every three days, once weekly, once every two weeks, once every month, once every two months, once every three months and once every six months.

Co-administration of an antibody with an additional therapeutic agent (combination therapy) encompasses administering a pharmaceutical composition comprising the anti-TACA antibody and the additional therapeutic agent and administering two or more separate pharmaceutical compositions, one comprising the anti-TACA antibody and the other(s) comprising the additional therapeutic agent(s). Further, co-administration or combination therapy refers to antibody and/or compound of formula IV, and additional therapeutic agents being administered at the same time as one another, as wells as instances in which an antibody and additional therapeutic agents are administered at different times. For instance, an antibody and compound of formula IV may be administered once every three days, while the additional therapeutic agent is administered once daily. Alternatively, an antibody and compound of formula IV may be administered prior to or subsequent to treatment of the disorder with the additional therapeutic agent. An antibody and compound of formula IV and one or more additional therapeutic agents (the combination therapy) may be administered once, twice or at least the period of time until the condition is treated, palliated or cured.

For example, anti-TACA antibodies may be co-administered with compounds that are useful for the treatment of cancer (e.g., cytotoxic drugs such as TAXOL®, taxotere, GLEEVEC® (Imatinib Mesylate), adriamycin, daunomycin, cisplatin, etoposide, a vinca alkaloid, vinblastine, vincristine, methotrexate, or adriamycin, daunomycin, cis-platinum, etoposide, and alkaloids, such as vincristine, farnesyl transferase inhibitors, endostatin and angiostatin, VEGF inhibitors, and antimetabolites such as methotrexate. The antibody and compound of formula IV may also be used in combination with a taxane derivative, a platinum coordination complex, a nucleoside analog, an anthracycline, a topoisomerase inhibitor, or an aromatase inhibitor). Radiation treatments can also be co-administered with a compound of the present invention for the treatment of cancers.

The antibodies of the present invention can be administered by a variety of methods known in the art including, via an oral, mucosal, buccal, intranasal, inhalable, intravenous, subcutaneous, intramuscular, parenteral, or topical route. In certain embodiments, the mode of administration is parenteral (e.g., intravenous, subcutaneous, intraperitoneal, intramuscular). In certain embodiments, the antibody is administered by intravenous infusion or injection. In particular embodiment, the antibody is administered by intrarticular, intramuscular or subcutaneous injection. As will be appreciated by the skilled artisan, the route and/or mode of administration will vary depending upon the desired results.

Dosage regimens can be adjusted to provide the optimum desired response (e.g., a therapeutic response). For example, a single bolus can be administered, several divided doses can be administered over time or the dose can be proportionally reduced or increased as indicated by the exigencies of the therapeutic situation. Parenteral compositions can be formulated in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier An exemplary, non-limiting range for a therapeutically effective amount of an antibody of the invention from 1 to 40 mg/kg. In certain embodiments, the dose is 8-20 mg/kg. In other embodiments, the dose is 10-12 mg/kg. In certain embodiments, a dose range for intrarticular injection would be a 15-30 mg/dose. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

EXAMPLES

1. Synthetic Experimental Section

General Methods.

NMR spectra were recorded on a 400 or 500 MHz instrument with the chemical shifts reported in ppm ($\delta$) in reference to tetramethylsilane (TMS), if not specified otherwise. Coupling constants (J) are reported in hertz (Hz). Optical rotations were obtained with an Autopol III polarimeter. High resolution electron spray ionization mass spectra (HR ESI MS) were recorded with a Waters Micromass-LCTPremier-XE instrument. MALDI-TOF MS were performed on a Bruker Ultraflex Mass Spectrometer. Thin layer chromatography (TLC) was performed on silica gel GF254 plates detected by charring with phosphomolybdic acid or 1% $H_2SO_4$ in EtOH. Molecular sieves (MS) were dried in high vacuum at 170-180° C. for 6-10 hours before use. Commercial anhydrous solvents and other reagents were used without further purification.

Synthesis of Compound 4.

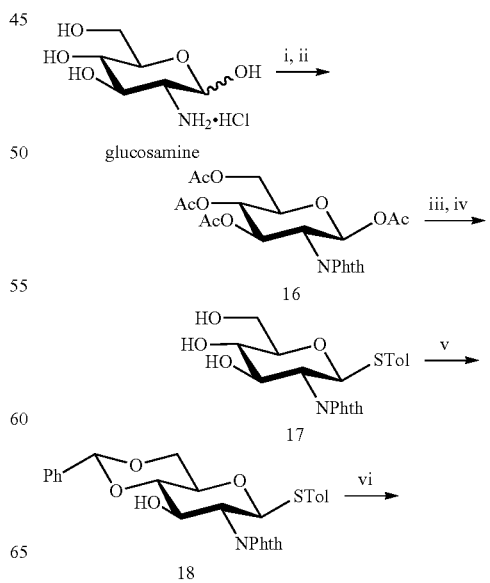

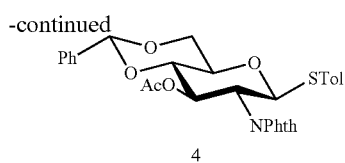

4

Reagents and Conditions: i) Phthalic anhydride, NaOH, H₂O—MeOH; ii) Ac₂O, AcONa; iii) TolSH, BF₃•Et₂O, CH₂Cl₂; iv) MeONa, MeOH—CH₂Cl₂; v) PhCH(OMe)₂, TsOH, DMF; vi) Ac₂O, TEA, CH₂Cl₂

Compound 16.

After the mixture of D-glucosamine hydrochloride (80.0 g, 0.37 mol), NaOH (15.6 g, 0.39 mol), H₂O (350 mL), and MeOH (150 mL) was stirred at room temperature for 1 hour, phthalic anhydride (63.2 g, 0.43 mol) was added, and the reaction was stirred at room temperature overnight. The solid materials were filtered, washed with a small amount of H₂O, and then dried to produce a solid intermediate (77.0 g). The mixture of this intermediate (20.0 g, 0.061 mol) and AcONa (13.5 g, 0.164 mol) in Ac₂O (270 mL) was refluxed for 10 hours. After removing most of Ac₂O in vacuum, the residue was poured into ice-water, and the mixture was extracted with DCM (dichloromethane, 300 mL). The organic layer was washed with saturated NaHCO₃ solution and brine, dried over anhydrous Na₂SO₄ and evaporated in vacuum. The residue was recrystallized from EtOAc and hexane to give 16 as a light yellow solid (14.9 g, 52%).

Compound 17.

To the stirred solution of 16 (26.7 g, 0.056 mol) and p-toluenethiol (9.0 g, 0.073 mol) in anhydrous DCM (90 mL) at 0° C., BF₃.Et₂O (10.6 mL, 0.084 mol) was added dropwise. When TLC showed the reaction was completed, the reaction mixture was washed with saturated NaHCO₃ solution and brine, dried over anhydrous Na₂SO₄, and concentrated. The residue was then dissolved in DCM (50 mL) and treated with CH₃ONa/CH₃OH solution (20 mL, 0.4 M) at room temperature for 1.5 hours. After most of the solvent was removed, the mixture was put in the refrigerator for 2 hours, and the mixture was filtered to give 17 as a white solid (10.8 g, 66.7% for two steps). (Hansen et al., *Eur. J. Org. Chem.,* (2007), 3392).

Compound 18.

The solution of 17 (10.8 g, 26.0 mmol), benzaldehyde dimethyl acetal (5.9 mL, 39.0 mmol) and TsOH.H₂O (0.29 g, 1.3 mmol) in anhydrous DMF (50 mL) was stirred at 50° C. with occasional vacuum application until TLC showed the reaction was complete. The reaction was quenched with triethylamine, and the mixture was diluted with DCM, washed with brine, dried over anhydrous Na₂SO₄ and concentrated in vacuum. The residue was purified by flash column chromatography to give 18 as a white solid (11.4 g, 87.0%). (Niu et al., *Synlett,* (2007), 2116).

Compound 4.

The mixture of 18 (13.0 g, 26.0 mmol), Ac₂O (3.7 mL, 39.0 mmol), triethylamine (7.9 mL, 78.0 mmol) and DMAP (12 mg, catalytic amount) in DCM (30 mL) was stirred at room temperature for 5 hours. The reaction mixture was washed with brine, dried over anhydrous Na₂SO₄ and concentrated. The residue was recrystallized from EtOAc and hexane to give 4 as a white solid (11.0 g, 78.0%). $^1$H NMR (CDCl₃, 400 MHz): δ 7.86 (m, 2H, aromatic H of Phth), 7.75 (m, 2H, aromatic H of Phth), 7.43 (m, 2H, aromatic H), 7.35 (m, 3H, aromatic H), 7.27 (d, J=8.0 Hz, 2H, aromatic H), 7.07 (d, J=8.0 Hz, 2H, aromatic H), 5.88 (t, J=9.6 Hz, 1H, H-3), 5.76 (d, J=10.8 Hz, 1H, H-1), 5.52 (s, 1H, PhCH), 4.42 (dd, J=10.4 and 4.8 Hz, 1H, H-6), 4.33 (t, J=10.8 Hz, 1H, H-2), 3.85-3.71 (m, 3H, H-4, H-5, H-6'), 2.32 (s, 3H, CH₃), 1.87 (s, 3H, OAc). $^{13}$C NMR (CDCl₃, 100 MHz): δ 136.9, 134.4, 133.7, 129.7, 128.2, 127.2, 123.7, 101.7, 84.0, 79.0, 70.7, 68.8, 54.4, 21.2, 20.5.

Synthesis of Compound 5.

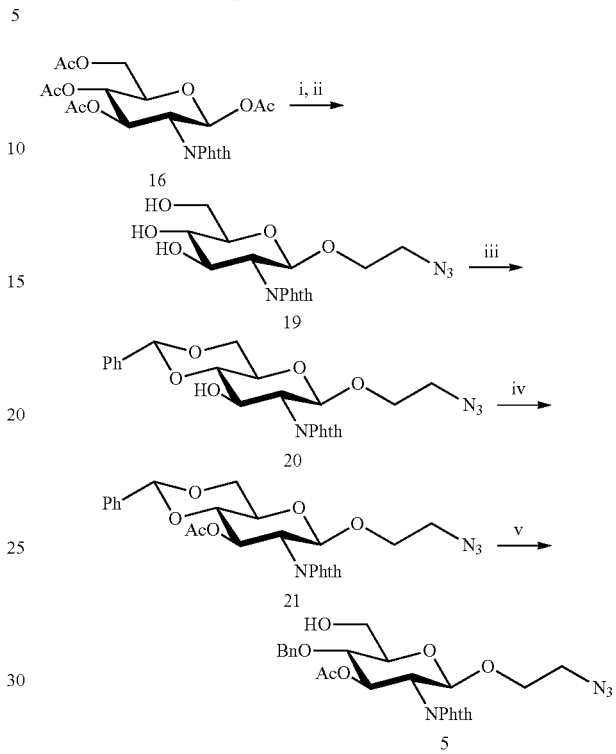

Reagents and Conditions: i) 2-azidoethanol, BF₃•Et₂O, CH₂Cl₂; ii) MeONa, MeOH; iii) PhCH(OMe)₂, TsOH, DMF; iv) Ac₂O, TEA, DMAP, CH₂Cl₂; v) BH₃/THF, TMSOTf Compound 19.

To the stirred mixture of 16 (13.5 g, 0.028 mol), 2-azidoethanol (10.0 g, 0.113 mol) and molecular sieve (4 Å, 3.5 g) in anhydrous DCM (40 mL) under argon, BF₃.Et₂O (5.4 mL, 0.042 mol) was added dropwise. After the mixture was stirred at room temperature for 2 days, the reaction was quenched with saturated NaHCO₃ solution. The mixture was diluted with DCM and filtered through a Celite pad. The filtrate and washings were combined and washed with brine, dried over Na₂SO₄, and concentrated. The residue was then dissolved in MeOH, to which was added CH₃ONa/CH₃OH solution (0.4 M) until pH=9. After at room temperature for 20 min, the reaction mixture was neutralized with Amberlite IR-120 (H⁺) resin, concentrated in vacuum, and finally purified by flash column chromatography to give 19 as syrup (9.0 g, 83.9% for two steps). $^1$H NMR (CD₃OD, 500 MHz): δ 7.85 (m, 2H, aromatic H), 7.80 (m, 2H, aromatic H), 5.25 (d, J=8.5 Hz, 1H, H-1), 4.23 (dd, J=11.0 and 8.5 Hz, 1H, H-2), 4.04-3.98 (m, 2H, H-3, H-6), 3.94 (dd, J=10.0 and 4.0 Hz, 1H, H-6'), 3.74 (m, 1H, OCH₂CH₂N₃), 3.65-3.60 (m, 1H, H-5), 3.47-3.38 (m, 2H, H-4, OCH₂CH₂N₃), 3.21-3.17 (m, 1H, CH₂N₃). $^{13}$C NMR (CD₃OD, 125 MHz): δ 134.2, 132.1, 98.6, 77.3, 71.5, 71.4, 68.4, 61.5, 57.3, 50.5, 8.5.

Compound 20.

It was prepared from 19 (85.5%) following the same procedure described for 18. $^1$H NMR (CDCl₃, 400 MHz): δ 7.85 (m, 2H, aromatic H of Phth), 7.73 (m, 2H, aromatic H of Phth), 7.46 (m, 2H, aromatic H), 7.37 (m, 3H, aromatic H), 5.55 (s, 1H, PhCH), 5.32 (d, J=8.5 Hz, 1H, H-1), 4.61-4.56 (m, 1H, H-3), 4.36 (dd, J=10.4 and 4.0 Hz, 1H, H-6), 4.24 (dd, J=10.4 and 8.8 Hz, 1H, H-6'), 3.98-3.93 (m, 1H, O CH$_2$CH$_2$N$_3$), 3.83-3.79 (m, 1H, H-2), 3.65-3.57 (m, 3H, H-4, H-5, OCH$_2$CH$_2$N$_3$), 3.37-3.30 (m, 1H, CH$_2$N$_3$), 3.23 (d, 1H, OH), 3.19-3.13 (m, 1H, CH$_2$N$_3$). $^{13}$C NMR (CDCl$_3$, 100 MHz): δ 162.9, 137.3, 134.3, 132.0, 129.5, 128.6, 128.4, 126.6, 123.6, 102.1, 99.2, 82.3, 68.8, 68.7, 66.5, 56.8, 50.7, 36.7, 31.6. (J. Xue et al *Org. Lett.*, (2005), 7, 3753).

Compound 21.

It was prepared from 20 (77.4%) following the same procedure described for 4. $^1$H NMR (CDCl$_3$, 400 MHz): δ 7.85 (m, 2H, aromatic H of Phth), 7.73 (m, 2H, aromatic H of Phth), 7.46 (m, 2H, aromatic H), 7.37 (m, 3H, aromatic H), 5.85 (t, J=9.2 Hz, 1H, H-3), 5.55 (s, 1H, PhCH), 5.53 (d, J=8.4 Hz, 1H, H-1), 4.41 (dd, J=10.4 and 4.8 Hz, 1H, H-6), 4.32 (dd, J=10.4 and 8.0 Hz, 1H, H-6'), 4.02-3.98 (m, 1H, OCH$_2$CH$_2$N$_3$), 3.88-3.74 (m, 3H, H-2, H-4, OCH$_2$CH$_2$N$_3$), 3.68-3.63 (m, 1H, H-5), 3.41-3.34 (m, 1H, CH$_2$N$_3$), 3.19-3.13 (m, 1H, CH$_2$N$_3$), 1.89 (s, 3H, OAc). $^{13}$C NMR (CDCl$_3$, 100 MHz): δ 134.5, 129.4, 128.5, 126.5, 123.8, 101.9, 99.0, 79.5, 69.9, 69.1, 68.9, 66.6, 55.5, 50.6, 20.8.

Compound 5.

To a stirred solution of 21 (3.0 g, 6.0 mmol) in BH$_3$.THF at 0° C., TMSOTf (1.5 mL) was added dropwise. After the mixture was stirred at 0° C. for another hour, the reaction was quenched by the addition of trietylamine and MeOH. The solution was then concentrated and purified by flash column chromatography to give 5 as a white solid (2.0 g, 66.0%). $^1$H NMR (CDCl$_3$, 500 MHz): δ 7.82 (m, 2H, aromatic H of Phth), 7.70 (m, 2H, aromatic H of Phth), 7.32 (m, 2H, aromatic H), 7.26 (m, 3H, aromatic H), 5.77 (dd, J=10.5 and 9.0 Hz, 1H, H-3), 5.50 (d, J=9.6 Hz, 1H, H-1), 4.66 (d, J=11.0 Hz, 2H, PhCH$_2$), 4.20 (dd, J=10.5 and 8.5 Hz, 1H, H-2), 3.99-3.89 (m, 2H, H-6, OCH$_2$CH$_2$N$_3$), 3.82 (m, 2H, H-5, H-6'), 3.67-3.62 (m, 2H, H-4, OCH$_2$CH$_2$N$_3$), 3.35-3.30 (m, 1H, CH$_2$N$_3$), 3.18-3.14 (m, 1H, CH$_2$N$_3$), 1.76 (s, 3H, OAc). $^{13}$C NMR (CDCl$_3$, 125 MHz): δ 171.5, 134.4, 134.3, 128.8, 128.7, 128.2, 128.0, 123.7, 98.4, 79.2, 76.4, 75.7, 75.6, 75.0, 73.3, 72.0, 69.0, 61.9, 56.9, 56.9, 55.3, 50.6, 20.8.

Compound 6.

After a mixture of 4 (1.6 g, 2.94 mmol), 5 (1.0 g, 1.96 mmol) and 4 Å molecular sieves (4 g) was stirred at room temperature in anhydrous dichloromethane (DCM) for 2 hours under an Argon atmosphere, it was cooled to −50° C., and then NIS (1.34 g, 5.88 mmol) and AgOTf (0.05 g, 0.2 mmol) were added. The mixture was stirred at room temperature for 2 days and then quenched by the addition of triethylamine. The molecular sieves were filtered off with a Celite pad and washed with DCM. The filtrate and washings were combined and washed with saturated Na$_2$S$_2$O$_3$ solution and brine, dried over anhydrous Na$_2$SO$_4$ and evaporated in vacuo. The residue was purified by flash column chromatography (toluene and AcOEt 10:1) to give 6 as a white solid (0.98 g, 54%). R$_f$=0.40 (toluene and AcOEt 4:1). $^1$H NMR (CDCl$_3$, 400 MHz): δ 7.82-7.78 (m, 4H), 7.70-7.66 (m, 4H), 7.46 (m, 2H), 7.37-7.35 (m, 3H), 7.26-7.23 (m, 3H), 7.06-7.03 (m, 2H), 5.88 (t, J=8.8 Hz, 1H, H-3'), 5.65 (dd, J=10.4, 8.8 Hz, 1H, H-3), 5.58 (d, J=8.8 Hz, 1H, H-1'), 5.56 (s, 1H, PhCH), 5.35 (d, J=8.8 Hz, 1H, H-1), 4.46-4.36 (m, 4H, H-6', H-2', PhCH$_2$), 4.14-4.08 (m, 2H, H-6, H-2), 3.88 (d, J=10.4 Hz, 1H, H-4'), 3.84-3.73 (m, 4H, H-6, H-6', H-5', OCH$_2$CH$_2$N$_3$), 3.67-3.62 (m, 1H, H-5), 3.58-3.51 (m, 2H, H-4, OCH$_2$CH$_2$N$_3$), 3.31-3.24 (m, 1H, CH$_2$N$_3$), 3.08-3.03 (m, 1H, CH$_2$N$_3$), 1.90 (s, 3H, OAc), 1.71 (s, 3H, OAc). $^{13}$C NMR (CDCl$_3$, 100 MHz): δ 170.5, 170.2, 137.6, 137.1, 134.5, 134.3, 129.4, 128.6, 128.5, 128.1, 127.7, 126.5, 123.8, 123.6, 101.9, 98.7, 98.1, 79.4, 77.6, 74.6, 73.2, 70.0, 68.9, 68.8, 68.2, 66.6, 55.5, 55.1, 50.1, 20.8, 20.7. HR ESI MS (m/z) calcd. for C$_{48}$H$_{45}$N$_5$O$_{15}$Na (M+Na)$^+$ 954.2810, found 954.2813.

Compound 7.

After a mixture of 6 (0.58 g, 0.63 mmol) and hydrazine monohydrate (5.5 mL) in ethanol (30 mL) was refluxed for 2 hours, it was concentrated in vacuo, and the residue was purified by flash column chromatography (CH$_2$Cl$_2$ and MeOH 15:1 to 10:1) to afford 7 as a white solid (0.27 g, 73%). R$_f$=0.65 (CH$_2$Cl$_2$ and MeOH 7:1). $^1$H NMR (CD$_3$OD, 400 MHz): δ 7.50-7.47 (m, 2H), 7.40-7.28 (m, 8H), 5.57 (s, 1H, PhCH), 4.95 (d, J=11.2 Hz, 1H, PhCH$_2$), 4.64 (d, J=10.4 Hz, 1H, PhCH$_2$), 4.37 (d, J=8.4 Hz, 1H, H-1'), 4.27 (d, J=8.0 Hz, 1H, H-1), 4.24 (dd, J=10.4, 4.8 Hz, 1H, H-6'), 4.09 (dd, J=11.2 and 2.4 Hz, 1H, H-6), 4.06-4.01 (m, 1H, OCH$_2$CH$_2$N$_3$), 3.79-3.68 (m, 3H, H-6, H-6', OCH$_2$CH$_2$N$_3$), 3.55-3.34 (m, 8H, H-3, H-3', H-4, H-4', H-5, H-5', CH$_2$N$_3$), 2.73 (t, J=8.8 Hz, 1H, H-2'), 2.65 (dd, J=10.4, 8.0 Hz, 1H, H-2). $^{13}$C NMR (CD$_3$OD, 100 MHz): δ 138.0, 128.7, 128.2, 127.9, 127.8, 127.6, 126.3, 104.4, 103.4, 101.9, 81.6, 78.7, 76.6, 74.8, 74.6, 72.9, 68.9, 68.7, 68.5, 66.9, 57.9, 57.4, 50.8. HR ESI MS (m/z): calcd for C$_{28}$H$_{38}$N$_5$O$_9$ (M+H)$^+$, 588.2670; found, 588.2647.

Compound 9.

After the solution of EDC.HCl (391 mg, 2.0 mmol) and 8 (260 mg, 0.6 mmol) in anhydrous DCM (8 mL) and DMF (0.5 mL) was stirred at room temperature for 0.5 hours, it was cooled to 0° C., and then a solution of 7 (120 mg, 0.2 mmol) in DMF (1.5 mL) was added. The mixture was stirred at room temperature overnight and then diluted with DCM, washed with brine, dried over anhydrous Na$_2$SO$_4$ and evaporated in vacuo. The residue was purified by flash column chromatography (CH$_2$Cl$_2$ and MeOH 40:1) to give 9 as a white solid (230 mg, 80%). R$_f$=0.40 (CH$_2$Cl$_2$ and MeOH 20:1). $^1$H NMR (CDCl$_3$, 400 MHz): δ 7.50-7.47 (m, 2H), 7.37-7.29 (m, 8H), 6.19 (d, J=4.8 Hz, 1H, NH'), 5.99 (d, J=6.8 Hz, 1H, NH), 5.53 (s, 1H, PhCH), 5.19-5.13 (m, 1H, lipid), 5.11-5.05 (m, 1H, lipid), 4.98 (d, J=11.2 Hz, 1H, PhCH$_2$), 4.81 (d, J=8.8 Hz, 1H, H-1), 4.64 (d, J=11.2 Hz, 1H, PhCH$_2$), 4.62 (d, J=3.2 Hz, 1H, 3-OH), 4.58 (d, J=8.0 Hz, 1H, H-1'), 4.30 (dd, J=10.8 and 4.0 Hz, 1H, H-6), 4.17 (dt, =J 9.2 and 3.2 Hz, 1H, H-3'), 4.09 (dd, J=11.2 and 2.4 Hz, 1H, H-6'), 4.06-4.01 (m, 1H, OCH$_2$CH$_2$N$_3$), 3.99 (d, J=3.2 Hz, 1H, 3'-OH), 3.93 (dt, J=9.6 and 3.2 Hz, 1H, H-3), 3.77-3.70 (m, 3H, H-6, H-6', OCH$_2$CH$_2$N$_3$), 3.56-3.31 (m, 8H, H-2, H-2', H-4, H-4', H-5, H-5', OCH$_2$CH$_2$N$_3$), 2.48 (d, J=6.4 Hz, 2H, lipid), 2.37-2.26 (m, 6H, lipid), 1.66-1.50 (m, 8H, lipid), 1.25 (br, 68H, 34×CH$_2$, lipid), 0.87 (t, J 6.4 Hz, 12H, 4×CH$_3$, lipid). $^{13}$C NMR (CDCl$_3$, 100 MHz): δ 174.6, 174.5, 172.1, 171.5, 138.5, 137.3, 129.3, 128.7, 128.5, 128.3, 128.1, 126.6, 102.1, 100.8, 100.3, 81.7, 78.5, 76.2, 74.9, 74.7, 71.7, 71.5, 71.1, 68.8, 68.2, 66.5, 59.1, 58.3, 50.9, 42.6, 36.7, 34.8, 32.1, 31.7, 29.9, 29.7, 29.6, 29.4, 25.5, 25.2, 22.9, 14.3. HR ESI MS (m/z): calcd. for C$_{80}$H$_{133}$N$_5$NaO$_{15}$ (M+Na)$^+$, 1426.9696; found, 1426.9696.

Compound 10.

After the solution of EDC.HCl (205 mg, 1.07 mmol) and lauric acid (142 mg, 0.712 mmol) in anhydrous DCM (5 mL) was stirred at room temperature for 20 min, a solution of 9 (100 mg, 0.07 mmol) and N,N-dimethylaminopyridine (DMAP, 8.7 mg, 0.07 mmol) in DCM (5 mL) was added. The mixture was stirred at 45° C. overnight, and it was then diluted with DCM, washed with brine, dried over anhydrous Na$_2$SO$_4$ and evaporated in vacuo. The residue was purified by flash column chromatography (CH$_2$Cl$_2$ and acetone 30:1 to 20:1) to give 10 as a white solid (110 mg, 87.3%). R$_f$=0.40 (CH$_2$Cl$_2$ and acetone 20:1). $^1$H NMR (CDCl$_3$, 400 MHz): δ 7.43-7.40 (m, 2H), 7.35-7.21 (m, 8H), 5.97 (d, J=7.2 Hz, 2H, NH, NH'), 5.48 (s, 1H, PhCH), 5.24 (t, J=10.0 Hz, 1H, H-3'), 5.17-5.00 (m, 3H, H-3, 2H lipid), 4.70 (d, J=8.4 Hz, 1H, H-1), 4.61-4.52

(m, 3H, H-1', PhC$\underline{H}_2$), 4.32 (dd, J=10.4, 4.8 Hz, 1H, H-6'), 4.06-3.90 (m, 4H, H-2, H-2', H-6, OC$\underline{H}_2$CH$_2$N$_3$), 3.79-3.64 (m, 4H, H-4', H-6, H-6', OC$\underline{H}_2$CH$_2$N$_3$), 3.61-3.42 (m, 4H, H-4, H-5, H-5', C$\underline{H}_2$N$_3$), 3.37-3.31 (m, 1H, C$\underline{H}_2$N$_3$), 2.47-2.40 (m, 2H, lipid), 2.34-2.15 (m, 6H, lipid), 1.64-1.48 (m, 12H, lipid), 1.24 (br, 104H, 52×CH$_2$, lipid), 0.87 (t, J=6.4 Hz, 18H, 6×CH$_3$, lipid). $^{13}$C NMR (CDCl$_3$, 100 MHz): δ 174.0, 173.9, 173.8, 169.9, 169.7, 137.8, 137.1, 129.3, 128.7, 128.4, 128.2, 127.9, 126.3, 102.2, 101.5, 100.7, 79.0, 76.4, 75.3, 74.6, 71.5, 71.3, 71.2, 68.8, 68.1, 67.1, 66.7, 54.7, 53.6, 51.0, 42.1, 41.8, 34.8, 34.7, 34.5, 34.3, 32.1, 29.9, 29.8, 29.7, 29.6, 29.5, 29.4, 29.3, 25.5, 25.3, 25.0, 22.9, 14.3. HR ESI MS (m/z): calcd. for C$_{104}$H$_{177}$N$_5$NaO$_{17}$ (M+Na)$^+$, 1791.3037; found, 1791.3024.

Compound 11.

After the mixture of 10 (85 mg, 48 μmol), NaBH$_3$CN (45 mg, 0.72 mmol) and 4 Å molecular sieves (1 g) in dry THF (10 mL) was stirred at room temperature for 2 hours, it was cooled to 0° C., and then HCl (1 M in dry ether) was added dropwise until the pH=2. After the reaction mixture was stirred at 0° C. for 1 hour and at room temperature for 3 hours, triethylamine (0.5 mL) was added to terminate the reaction. The molecular sieves were filtered off through a Celite pat and washed with DCM. The filtrate and washings were combined and washed with saturated NaHCO$_3$ solution and brine, dried over anhydrous Na$_2$SO$_4$ and finally evaporated in vacuo. The residue was purified by flash column chromatography (CH$_2$Cl$_2$ and acetone 15:1) to give 11 as a white solid (60 mg, 70.6%). R$_f$=0.25 (CH$_2$Cl$_2$ and acetone 15:1). [α]$^{24}_D$ −15.0 (c 1.0, CHCl$_3$). $^1$H NMR (CDCl$_3$, 400 MHz): δ 7.36-7.19 (m, 10H), 5.96-5.90 (m, 2H, NH', NH), 5.15-4.98 (m, 4H, H-3', H-3, and 2H of lipid), 4.64 (d, J=8.8 Hz, 1H, H-1), 4.60-4.50 (m, 5H, H-1', 2×PhC$\underline{H}_2$), 4.04-3.85 (m, 4H, H-2', H-2, H-6', OC$\underline{H}_2$CH$_2$N$_3$), 3.79-3.63 (m, 5H, H-4, 2×H-6, H-6', OC$\underline{H}_2$CH$_2$N$_3$), 3.60-3.48 (m, 3H, H-4', H-5', H-5), 3.46-3.38 (m, 1H, C$\underline{H}_2$N$_3$), 3.33-3.26 (m, 1H, C$\underline{H}_2$N$_3$), 2.46-2.12 (m, 8H, lipid), 1.66-1.46 (m, 12H, lipid), 1.25 (br, 104H, 52×CH$_2$, lipid), 0.87 (t, J=6.4 Hz, 18H, 6×CH$_3$, lipid). $^{13}$C NMR (CDCl$_3$, 100 MHz): δ 174.8, 174.0, 173.9, 169.9, 169.8, 137.8, 128.7, 128.6, 128.1, 128.0, 127.9, 101.4, 100.8, 76.5, 75.2, 74.7, 74.2, 74.0, 71.3, 71.2, 70.7, 67.9, 67.3, 54.0, 53.7, 50.9, 42.0, 41.8, 34.7, 34.4, 34.3, 32.2, 29.9, 29.8, 29.7, 29.6, 29.5, 29.4, 25.5, 25.3, 25.2, 25.0, 22.9, 14.3. MALDI-TOF MS (m/z): calcd for C$_{104}$H$_{179}$N$_5$O$_{17}$, 1770.3; found, 1793.3 (M+Na)$^+$.

Compound 3.

To the stirred solution of 11 (38 mg, 21 μmol) in dry DCM (3 mL), dibenzyl diisopropylphosphoramidite 12 (21 μL, 64 μmol) and 1H-tetrazole (~0.45 M in CH$_3$CN, 0.24 mL, 0.107 mmol) were added. After the mixture was stirred at room temperature for 2 hours and then cooled to −20° C., t-BuOOH (~5.5 M in CH$_3$CN, 39 μL, 0.214 mmol) was added, and the mixture was stirred at room temperature for another 2 hours. The solvent was removed in vacuo, and the residue was purified by flash column chromatography (CH$_2$Cl$_2$ and MeOH 60:1) to give 3 as syrup (36.5 mg, 84%). R$_f$=0.45 (CH$_2$Cl$_2$ and MeOH 40:1). [α]$^{24}_D$ −9.0 (c 0.5, CHCl$_3$). $^1$H NMR (CDCl$_3$, 400 MHz): δ 7.33-7.19 (m, 20H), 5.87 (d, J=8.8 Hz, 1H, NH'), 5.80 (d, J=8.8 Hz, 1H, NH), 5.31 (dd, J=10.4 and 8.8 Hz, 1H, H-3'), 5.13-5.04 (m, 2H, H-3 and 1H of lipid), 5.02-4.95 (m, 1H, lipid), 4.91-4.85 (m, 4H, (PhC$\underline{H}_2$O)$_2$P), 4.77 (d, J=8.4 Hz, 1H, H-1'), 4.54 (s, 2H, PhC$\underline{H}_2$), 4.51 (d, J=8.0 Hz, 1H, H-1), 4.48-4.41 (m, 3H, H-4', PhC$\underline{H}_2$), 4.05-3.88 (m, 3H, H-2, H-6, OC$\underline{H}_2$CH$_2$N$_3$), 3.84-3.68 (m, 3H, H-2', H-6', H-6), 3.67-3.47 (m, 5H, OC$\underline{H}_2$CH$_2$N$_3$, H-6', H-5', H-5, H-4), 3.46-3.39 (m, 1H, C$\underline{H}_2$N$_3$), 3.32-3.25 (m, 1H, C$\underline{H}_2$N$_3$), 2.45-2.35 (m, 2H, lipid), 2.32-2.12 (m, 8H, lipid), 1.64-1.36 (m, 10H, lipid), 1.34-1.08 (br, 104H, 52×CH$_2$, lipid), 0.87 (t, J=6.4 Hz, 18H, 6×CH$_3$, lipid). $^{13}$C NMR (CDCl$_3$, 100 MHz): δ 128.8, 128.7, 128.6, 128.1, 128.0, 127.8, 101.0, 100.8, 76.5, 75.2, 74.7, 74.6, 74.5, 74.3, 73.6, 72.6, 71.3, 71.1, 70.7, 69.8, 69.7, 68.9, 68.3, 67.3, 54.8, 53.7, 50.9, 42.0, 41.9, 34.7, 34.4, 34.1, 32.1, 29.9, 29.8, 29.7, 29.6, 29.4, 25.6, 25.2, 25.0, 24.8, 22.9, 14.4. $^{31}$P NMR (CDCl$_3$, 161 MHz): δ −1.11. HR ESI MS (m/z): calcd. for C$_{118}$H$_{192}$N$_5$NaO$_{20}$P (M+Na)$^+$, 2053.3796; found, 2053.3835.

Compound 13.

A suspension of 3 (25 mg, 12 μmol), active zinc dust (25.0 mg, 0.38 mmol), and acetic acid (7 μL, 0.12 mmol) in DCM (2 mL) was stirred at room temperature for 24 h, and then solid materials were removed by filtration and washed with DCM. The combined filtrates were neutralized with DIPEA, washed with brine, dried over anhydrous Na$_2$SO$_4$, and then concentrated in vacuo. The product [HR ESI MS (m/z): calcd for C$_{118}$H$_{195}$N$_3$O$_{20}$P (M+H)$^+$, 2005.4072, found, 2005.4142] was used for the next step of reaction without further purification. The solution of the obtained crude amine, succinic anhydride (5 mg, 49 μmol), DIPEA (20 μL, 0.12 mmol) and a catalytic amount of DMAP in DCM (2 mL) and DMF (0.5 mL) was stirred at room temperature overnight. The mixture was concentrated in vacuo and co-evaporated with toluene a couple of times, and the residue was purified by flash column chromatography (CH$_2$Cl$_2$ and MeOH 30:1) to give 13 as a white solid (18 mg, 70%). R$_f$=0.3 (CH$_2$Cl$_2$ and MeOH 20:1). [α]$^{24}_D$ −12.0 (c 0.25, CHCl$_3$). $^1$H NMR (CDCl$_3$, 400 MHz): δ 7.34-7.16 (m, 20H), 6.61 (m, 1H, OCH$_2$CH$_2$N$\underline{H}$), 6.34 (d, J=8.8 Hz, 1H, NH), 5.94 (d, J=8.8 Hz, 1H, NH), 5.43 (t, J=9.6 Hz, 1H, H-3'), 5.10-4.97 (m, 3H, H-3 and 2H of lipid), 4.93-4.83 (m, 4H, (PhC$\underline{H}_2$O)$_2$P), 4.78 (d, J=8.0 Hz, 1H, H-1'), 4.57-4.43 (m, 5H, H-4', 2×PhC$\underline{H}_2$), 4.34 (d, J=8.0 Hz, 1H, H-1), 4.06-3.95 (m, 2H, H-2, H-6), 3.84-3.76 (m, 2H, H-2', H-6'), 3.74-3.61 (m, 5H, OC$\underline{H}_2$CH$_2$NH, H-5', H-6, H-6'), 3.60-3.45 (m, 3H, OC$\underline{H}_2$CH$_2$NH, H-5, H-4), 3.28-3.20 (m, 1H, OCH$_2$C$\underline{H}_2$NH), 2.82-2.72 (m, 1H, C$\underline{H}_2$CH$_2$COOH), 2.64-2.46 (m, 3H, C$\underline{H}_2$CH$_2$COOH), 2.46-2.38 (m, 2H, lipid), 2.34-2.10 (m, 8H, lipid), 1.64-1.35 (m, 10H, lipid), 1.34-1.02 (br, 104H, 52×CH$_2$, lipid), 0.87 (t, J=5.4 Hz, 18H, 6×CH$_3$, lipid). $^{13}$C NMR (CDCl$_3$, 125 MHz): δ 174.3, 174.2, 173.9, 170.3, 170.3, 138.3, 137.8, 135.7, 128.8, 128.7, 128.6, 128.2, 128.1, 128.0, 127.9, 127.8, 101.4, 100.9, 75.0, 74.8, 74.7, 74.3, 73.6, 72.7, 71.5, 69.9, 69.8, 68.9, 68.3, 54.8, 54.0, 42.0, 41.6, 40.2, 34.8, 34.5, 34.3, 34.2, 32.2, 29.9, 29.8, 29.7, 29.6, 29.5, 29.4, 25.6, 25.5, 25.3, 25.0, 24.8, 22.9, 14.4. $^{31}$P NMR (CDCl$_3$, 161 MHz): δ −1.36. HR ESI MS (m/z): calcd. for C$_{122}$H$_{198}$N$_3$NaO$_{23}$P (M+Na)$^+$, 2127.4051; found, 2127.4089.

Compound 14.

To a stirred solution of 13 (18 mg, 8 μmol) and p-nitrophenol (5.9 mg, 42 μmol) in DCM (5 mL) was added EDC.HCl (8.2 mg, 42 μmol) in an ice bath. After the mixture was stirred at room temperature for 5 h, it was diluted with DCM, washed with brine, dried over anhydrous Na$_2$SO$_4$, and condensed in vacuo. The residue was purified on a TLC plate (CH$_2$Cl$_2$ and MeOH 20:1) to give 14 as a white solid (16 mg, 83.5%). R$_f$=0.55 (CH$_2$Cl$_2$ and MeOH 20:1). [α]$^{24}_D$ −10.0 (c 0.65, CHCl$_3$). $^1$H NMR (CDCl$_3$, 400 MHz): δ 8.24-8.19 (m, 2H), 7.34-7.16 (m, 22H), 6.73 (m, 1H, OCH$_2$CH$_2$N$\underline{H}$), 6.09 (d, J 8.8 Hz, 1H, NH), 5.78 (d, J=9.2 Hz, 1H, NH), 5.32 (t, J=8.8 Hz, 1H, H-3'), 5.08-5.03 (m, 1H, lipid), 5.00-4.94 (m, 2H, H-3 and 1H of lipid), 4.92-4.83 (m, 4H, (PhC$\underline{H}_2$O)$_2$P), 4.71 (d, J=8.0 Hz, 1H, H-1'), 4.57-4.49 (m, 2H, PhC$\underline{H}_2$), 4.48-4.40 (m, 3H, H-4', PhC$\underline{H}_2$), 4.31 (d, J=8.0 Hz, 1H, H-1), 4.06-3.98 (m, 2H, H-6, H-2), 3.83-3.71 (m, 3H, H-2', H-6', OC$\underline{H}_2$CH$_2$NH), 3.69-3.58 (m, 4H, OC$\underline{H}_2$CH$_2$NH, H-5', H-6, H-6'), 3.55-3.34 (m, 4H, H-5, H-4, OCH$_2$CH$_2$NH), 2.92 (t, J=7.6 Hz, 2H, CH$_2$COOPhNO$_2$), 2.62 (t, J=7.6 Hz, 2H, CH$_2$CH$_2$COOPhNO$_2$), 2.44-2.35 (m, 2H, lipid), 2.30-2.12 (m, 8H, lipid), 1.70-1.36 (m, 10H, lipid), 1.34-1.02 (br, 104H, 52×CH$_2$, lipid), 0.87 (t, J=6.4 Hz, 18H, 6×CH$_3$, lipid). $^{13}$C NMR (CDCl$_3$, 125 MHz): δ 174.2, 174.1, 173.9, 173.8, 171.7, 171.4, 170.4, 170.2, 155.7, 145.5, 138.2, 137.7, 135.6, 135.5, 128.9, 128.8, 128.7, 128.6, 128.3, 128.2, 128.1, 128.0, 127.9, 127.8, 125.4, 122.7, 101.5, 101.0, 76.4, 74.8, 74.5, 74.4, 73.6, 72.5, 71.3, 71.2, 70.0, 69.9, 69.8, 68.9, 68.5, 68.0, 54.8, 54.3, 42.2, 41.9, 40.2, 34.8, 34.5, 34.4, 34.2, 32.2, 30.5, 29.9, 29.8, 29.7, 29.6, 29.5, 29.4, 25.6, 25.3, 25.0, 24.8, 22.9, 14.4. $^{31}$P NMR (CDCl$_3$, 161 MHz): δ −1.04. HR ESI MS (m/z): calcd. for C$_{128}$H$_{201}$N$_4$NaO$_{25}$P (M+Na)$^+$, 2248.4215; found, 2248.4226.

Compound 2.

To a stirred solution of 14 (12 mg, 5 μmol) and 15 (6 mg, 8 μmol) in DMF (1.5 mL), N-methylmorpholine (NMM, 6 μL, 54 μmol) was added at 0° C. The reaction mixture was stirred at room temperature overnight, and then DMF was removed in vacuo. The residue was purified on a TLC plate (CH$_2$Cl$_2$ and MeOH 3:1) to give 2 as a white solid (10 mg, 65%). R$_f$=0.2 (CH$_2$Cl$_2$ and MeOH 3:1). [α]$^{24}{}_D$ −4.5 (c 0.38, CHCl$_3$ and MeOH 4:1). $^1$H NMR (CDCl$_3$ and CD$_3$OD 6:1, 500 MHz): δ 7.24-7.09 (m, 25H), 5.30 (t, J=10.0 Hz, 1H, H-3'), 5.02-4.91 (m, 3H, H-3, and 2H of lipid), 4.81-4.73 (m, 4H, (PhCH$_2$O)$_2$P), 4.68 (d, J=8.0 Hz, 1H, H-1'), 4.47-4.40 (m, 2H, PhCH$_2$), 4.39-4.33 (m, 3H, H-4', PhCH$_2$), 4.32 (d, J=8.0 Hz, 1H, H-1"), 4.28 (d, J=9.0 Hz, 1H, H-1), 4.17 (d, J=7.5 Hz, 1H, H-1'''), 3.99-3.94 (m, 2H, H-6), 3.94-3.40 (m, 31H), 3.38-3.16 (m, 5H), 2.40-2.32 (m, 4H), 2.29 (dd, J=15.0 and 6.0 Hz, 1H, H-3"e of GM$_3$), 2.25-2.00 (m, 11H, lipid and H-3"a of GM$_3$), 1.67-1.34 (m, 10H, lipid), 1.30-0.98 (br, 104H, 52×CH$_2$, lipid), 0.84-0.70 (m, 18H, 6×CH$_3$, lipid). $^{13}$C NMR (CDCl$_3$ and CD$_3$OD 6:1, 125 MHz): δ 129.0, 128.8, 128.6, 128.5, 128.4, 128.0, 127.8, 127.7, 127.6, 127.1, 103.9, 102.9, 101.2, 100.5, 80.0, 77.5, 76.5, 76.1, 75.4, 74.9, 74.6, 74.2, 73.9, 73.7, 73.4, 73.3, 72.4, 72.3, 71.5, 71.2, 70.9, 69.9, 69.8, 69.2, 68.8, 68.5, 68.1, 67.5, 63.4, 61.7, 60.9, 54.4, 53.7, 52.7, 49.4, 49.2, 49.1, 48.9, 42.8, 41.1, 40.9, 39.6, 39.4, 34.5, 34.2, 34.0, 31.9, 31.0, 30.9, 29.7, 29.5, 29.4, 29.3, 25.4, 25.1, 24.8, 24.6, 22.7, 14.0. $^{31}$P NMR (CDCl$_3$ and CD$_3$OD 6:1, 161 MHz): δ −1.52. HR ESI MS (m/z): calcd. for C$_{153}$H$_{244}$N$_5$Na$_2$O$_{41}$P (M+2Na)$^{2+}$, 1442.3342; found, 1442.3287.

Compound 1.

A mixture of 2 (7.5 mg, 2.64 μmol) and 10% Pd—C (5.0 mg) in DCM-MeOH (1:1, 4 mL) was stirred under an atmosphere of H$_2$ at room temperature for 1 day. Thereafter, the catalyst was removed by filtration through a Celite pad, and the Celite pad was subsequently washed with DCM-MeOH (1:1) and MeOH. The combined filtrates were concentrated in vacuum, and the residue was purified by a short silica gel column (eluent: DCM/MeOH 1:3) to give 1 as a white solid (4.0 mg, 61.5%). R$_f$=0.25 (CH$_2$Cl$_2$/MeOH 1:3). $^1$H NMR (CDCl$_3$—CD$_3$OD, 500 MHz): δ $^{31}$P NMR (CDCl$_3$—CD$_3$OD, 161 MHz): δ 2.875.

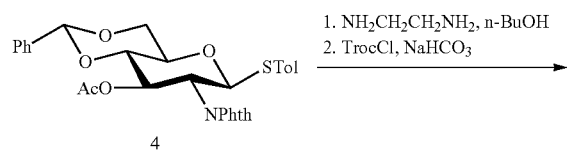

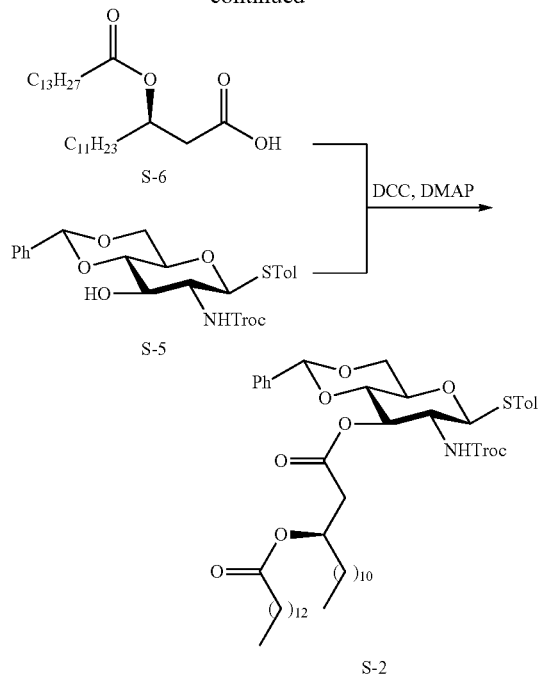

Compound S-2.

To a stirred solution of S-6 (200 mg, 0.44 mmol) in dichloromethane (DCM) were added DCC (184 mg, 0.90 mmol) and DMAP (28 mg, 0.23 mmol) at room temperature, and after the mixture was stirred at room temperature for 10 minutes, a solution of S-5 (200 mg, 0.36 mmol) in DCM (1.5 mL) was added. The reaction mixture was stirred for another 16 hours at room temperature, and the solid materials were removed by filtration, and the residue was washed with DCM (10 mL). The combined filtrate was concentrated in vacuum, and the residue was purified by silica gel column chromatography to afford S-2 as a white solid (330 mg, 90%). [α]$_D$ +14.1 (c 1.0, CHCl$_3$). $^1$H NMR (CDCl$_3$, 400 MHz): δ 7.42-7.26 (m, 7H), 7.12 (d, J=7.2 Hz, 2H), 5.51 (d, J=9.6 Hz, 1H, NH), 5.48 (s, 1H, PhCH), 5.38 (t, J=9.6 Hz, 1H, H-3), 5.20-5.14 (m, 1H, lipid), 4.90 (d, J=10.4 Hz, 1H, H-1), 4.76 (d, J=4 Hz, 2H, CH$_2$CCl$_3$), 4.34 (dd, J=4.8, 10.4 Hz, 1H, H-6a), 3.78 (t, J=10.0 Hz, 1H, H-6b), 3.68-3.60 (m, 2H, H-4, H-2), 3.56-3.50 (m, 1H, H-5), 2.62-2.48 (m, 2H), 2.35 (s, 3H), 2.17 (t, J=7.2 Hz, 2H), 1.55-1.52 (m, 4H), 1.32-1.20 (m, 40H), 0.88 (t, J=7.6 Hz, 6H). $^{13}$C NMR (CDCl$_3$, 100 MHz): δ 173.7, 170.2, 154.3, 138.8, 137.0, 133.7, 130.1, 129.4, 128.5, 126.4, 101.7, 88.1, 78.8, 74.8, 72.5, 70.7, 70.2, 68.7, 56.0, 39.5, 34.6, 34.1, 32.1, 29.9, 29.8, 29.6, 29.6, 29.4, 25.3, 25.2, 22.9, 21.4, 14.4. HR ESI MS (m/z): calcd for C$_{51}$H$_{76}$Cl$_3$NO$_9$SNa (M+Na)$^+$, 1006.4204; found, 1006.4201.

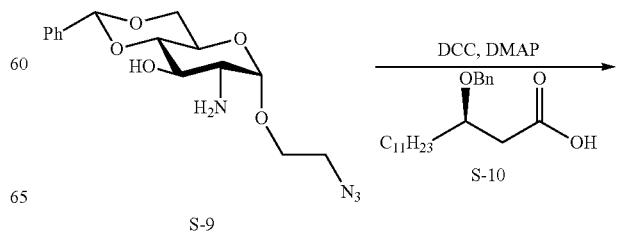

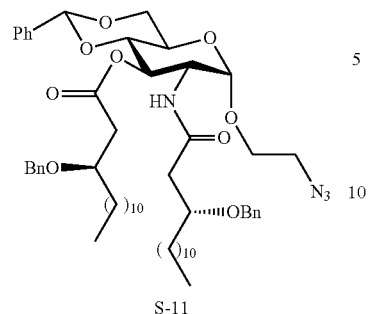

Compound S-11.

To a stirred solution of 5-10 (0.70 g, 2.1 mmol) in DCM (10 mL) were added DCC (N, N'-dicyclohexylcarbodiimide) (0.64 g, 3.2 mmol) and DMAP (dimethylaminopyridine) (0.10 g, 0.08 mmol) at room temperature. After the mixture was stirred for 10 minutes, a solution of S-9 (0.27 g, 0.81 mmol) in DCM (1.5 mL) was added, and the reaction mixture was stirred for another 16 hours at room temperature. The solid materials were then removed by filtration, and the residue was washed with DCM (10 mL). The combined filtrate was concentrated in vacuum, and the residue was purified by silica gel column chromatography to afford S-11 as a white solid (0.56 g, 71%). $[\alpha]_D$ +26.8 (c 1.0, CHCl$_3$). $^1$H NMR (CDCl$_3$, 400 MHz): δ 7.40-7.21 (m, 15H), 6.20 (d, J=9.6 Hz, 1H, NH), 5.46 (s, 1H, PhC$\underline{H}$), 5.38 (t, J=9.6 Hz, 1H, H-3), 4.73 (d, J=3.2 Hz, 1H, H-1), 4.56-4.35 (m, 5H, 2PhC$\underline{H}_2$, H-2), 4.25 (dd, J=9.6, 4.4 Hz, 1H, H-5), 3.92-3.68 (m, 6H, H-6a, H-6b, H-4, 2 BnOC$\underline{H}$, OC$\underline{H}_2$CH$_2$N$_3$), 3.25 (dd, J=7.6, 16.4 Hz, 2H, OC$\underline{H}_2$CH$_2$N$_3$), 3.15-3.09 (m, 1H, C$\underline{H}_2$N$_3$), 2.66 (dd, J=6.8, 10.8 Hz, 1H), 2.44-2.36 (m, 1H), 2.33-2.26 (m, 2H), 1.47-1.43 (m, 4H), 1.30-1.19 (m, 36H), 0.89-0.86 (t, 6H). $^{13}$C NMR (CDCl$_3$, 100 MHz): δ 172.0 171.6, 138.9, 138.8, 137.1, 129.3, 128.6, 128.5, 128.4, 128.0, 127.9, 127.8, 127.6, 126.3, 101.8, 98.5, 79.4, 76.7, 75.7, 71.6, 71.3, 70.0, 69.0, 67.3, 63.4, 52.3, 50.4, 42.0, 40.0, 34.8, 34.1, 32.2, 29.9, 29.9, 29.8, 29.6, 25.5, 25.4, 22.9, 14.4. HR ESI MS (m/z): calcd for C$_{57}$H$_{84}$N$_4$O$_9$Na (M+Na)$^+$, 991.6136; found, 991.6152.

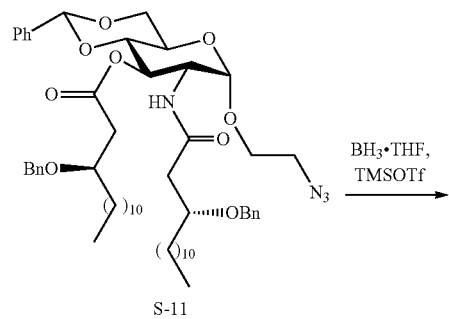

Compound S-3.

To a stirred solution of compound S-11 (365 mg, 0.38 mmol) in BH$_3$/THF (tetrahydrofuran) (2 mL, 2.0 mmol) was added dropwise TMSOTf (trimethylsilyltrifluoro methane sulfonate) (0.08 mL, 0.46 mmol) in ice-water bath. After 1 hour of stirring, TLC showed that the reaction was complete. The reaction was then quenched with triethylamine and MeOH, and the mixture was concentrated, and the residue was purified by silica gel column chromatography to afford S-3 as a white solid (213 mg, 58%). $^1$H NMR (CDCl$_3$, 400 MHz): δ 7.33-7.20 (m, 15H), 6.13 (d, J=8.8 Hz, 1H, NH), 5.39-5.34 (m, 1H, H-3), 4.71 (d, J=4.0 Hz, 1H, H-1), 4.65-4.43 (m, 6H, 3 PhC$\underline{H}_2$), 4.28-4.22 (m, 1H, H-2), 3.85-3.62 (m, 7H, H-6b, H-4, H-5, H-6a, 2BnOC$\underline{H}$, OC$\underline{H}_2$CH$_2$N$_3$), 3.47-3.38 (m, 2H, OC$\underline{H}_2$CH$_2$N$_3$), 3.25-3.19 (m, 2H), 3.12-3.07 (m, 1H, C$\underline{H}_2$N$_3$), 2.56 (dd, J=7.2, 16.0 Hz, 1H), 2.39 (dd, J=5.6, 16.0 Hz, 1H), 2.29-2.27 (m, 2H), 1.66-1.43 (m, 4H), 1.37-1.16 (m, 36H), 0.89-0.86 (t, 6H). $^{13}$C NMR (CDCl$_3$, 100 MHz): δ 172.3, 171.6, 139.0, 138.8, 137.9, 128.7, 128.6, 128.5, 128.2, 128.1, 128.0, 127.9, 127.9, 127.8, 127.7, 127.6, 97.9, 76.7, 75.7, 75.3, 74.9, 73.3, 71.7, 71.6, 71.5, 70.8, 67.2, 61.7, 52.4, 50.4, 42.1, 40.0, 34.5, 34.2, 34.1, 32.2, 30.0, 29.9, 29.9, 29.8, 29.6, 26.7, 26.6, 25.5, 25.4, 25.2, 22.9, 14.4. HR ESI MS (m/z): calcd. for C$_{57}$H$_{86}$N$_4$O$_9$Na (M+Na)$^+$, 993.6293; found, 993.6284.

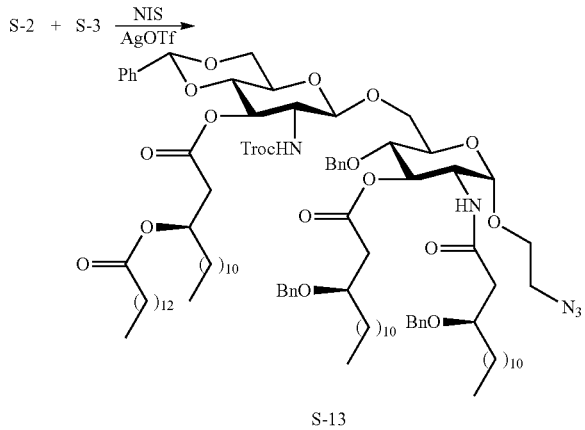

Compound S-13.

A mixture of S-2 (162 mg, 0.165 mmol), S-3 (150 mg, 0.155 mmol) and 4 Å MS (molecular sieves)(0.5 g) was stirred in anhydrous DCM (2 mL) at room temperature for 0.5 hour. The reaction mixture was then cooled to −50° C., and NIS (N-iodosuccinimide) (85 mg, 10 mmol) was added. The reaction mixture was allowed to warm to −30° C. and stirred for another 1 hour before a catalytic amount of AgOTf was added. When TLC showed the glycosyl donor S-2 was consumed completely, the reaction mixture was quenched with the addition of triethylamine. MS was removed by filtration through a Celite pad. The filtrate was washed with water, dried, and then evaporated in vacuum. The residue was purified by silica gel column chromatography to give S-13 as a white solid (212 mg, 75%). $[\alpha]_D$ +11.2 (c 1.0, CHCl$_3$); $^1$H NMR (CDCl$_3$, 400 MHz): δ 7.42-7.20 (m, 20H), 6.12 (d, J=9.6 Hz, 1H, NH), 5.49 (s, 1H), 5.36 (t, J=9.2 Hz, 1H, H-3), 5.29-5.25 (m, 1H, H-3'), 5.20-5.17 (m, 1H, lipid), 4.72 (d, J=3.2 Hz, 1H, H-1), 4.68-4.46 (m, 8H, Troc, 3PhC$\underline{H}_2$), 4.42 (d, J=8.0 Hz, 1H, H-1'), 4.33 (dd, J=4.8, 10.4 Hz, 1H, H-6a'), 4.29-4.23 (m, 1H, H-2), 4.01 (bd, J=10.4 Hz, 1H, H-6b), 3.87-3.75 (m, 4H, 2BnOC$\underline{H}$, H-5, H-6b'), 3.69-3.63 (m, 5H, H-2', H-4, H-4', H-6a, OC$\underline{H}_2$CH$_2$N$_3$), 3.47-3.40 (m, 2H, H-5', lipid), 3.25-3.19 (m, 2H, OC$\underline{H}_2$C$\underline{H}_2$N$_3$), 3.12-3.07 (m, 1H, C$\underline{H}_2$N$_3$), 2.62-2.53 (m, 3H), 2.41 (dd, J=4.8, 16.0 Hz, 1H), 2.28 (d, J=6.0 Hz, 2H), 2.19 (t, J=7.2 Hz, 2H), 1.62-1.44 (m, 8H), 1.38-1.25 (m, 86H), 0.94-0.88 (m, 12H). $^{13}$C NMR (CDCl$_3$, 100 MHz): δ 173.7, 172.2, 171.4, 170.3, 154.3, 138.9, 138.8, 138.2, 137.1, 129.4, 128.8, 128.6, 128.5, 128.2, 128.1, 128.0, 127.7, 126.4, 101.7, 97.8, 95.6, 78.9, 76.7, 75.7, 74.8, 74.5, 73.7, 71.6, 71.3, 70.8, 70.4, 70.2, 68.7, 67.2, 66.6, 57.0, 52.1, 50.4, 42.1, 40.0, 39.5, 34.6, 34.4, 34.3, 34.1, 32.2, 29.9, 29.8, 29.6, 29.4, 26.7, 25.4, 25.2, 22.9, 14.4. HR ESI MS (m/z): calcd. for C$_{101}$H$_{154}$Cl$_3$N$_5$O$_{18}$Na (M+Na)$^+$, 1853.0252; found, 1853.0221.

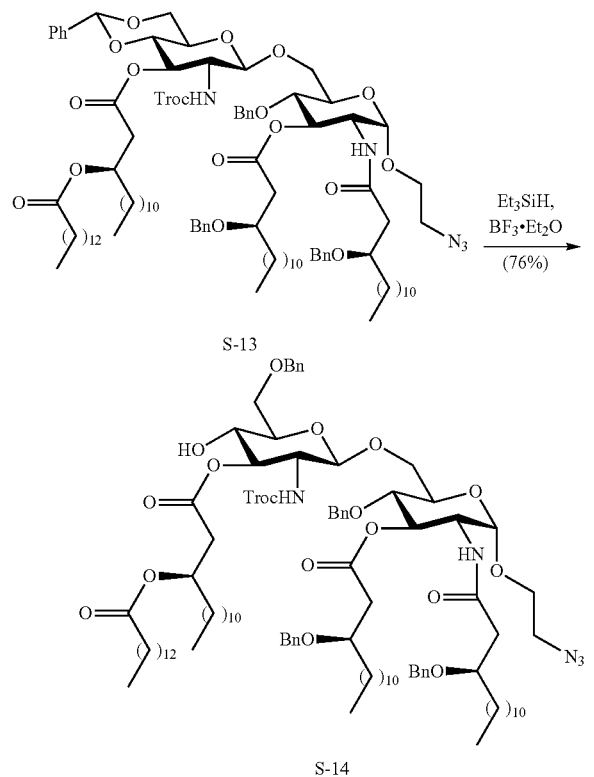

S-13

Compound S-14.

To the solution of S-13 (70 mg, 0.038 mmol) in DCM (2.0 mL) at 0° C. were added Et$_3$SiH (triethylsilane) (15 equiv., 0.10 mL) and BF$_3$·Et$_2$O (2 equiv., 10 μl). After the mixture was warmed to 25° C. over a period of 2 hours, it was diluted with DCM (30 mL), washed with NaHCO$_3$ solution (5 mL), dried and concentrated. The residue was purified by silica gel column chromatography to provide S-14 (53 mg, 76%). $[\alpha]_D$ +17.4 (c 1.0, CHCl$_3$). $^1$H NMR (CDCl$_3$, 400 MHz): δ 7.36-7.17 (m, 20H), 6.10 (d, J=9.6 Hz, 1H, NH), 5.31 (dd, J=8.8, 10.4 Hz, 1H, H-3), 5.12-5.10 (m, 1H, lipid), 5.09 (d, J=8.4 Hz, 1H, NH'), 4.91 (t, J=9.6 Hz, 1H, H-3'), 4.70 (d, J=4.0 Hz, 1H, H-1), 4.63-4.42 (m, 10H, Troc, 4PhC$\underline{H}_2$), 4.28-4.20 (m, 2H, H-2, H-1'), 4.06-4.02 (m, 1H, H-6b), 3.84-3.72 (m, 5H, 2BnOC$\underline{H}$, H-5, H-6a'), 3.67-3.60 (m, 5H, H-2', H-4, H-4', H-6a, H-6b'), 3.48-3.38 (m, 2H, H-5', OC$\underline{H}_2$CH$_2$N$_3$), 3.24-3.17 (m, 2H, OC$\underline{H}_2$CH$_2$N$_3$), 3.11-3.05 (m, 1H, C$\underline{H}_2$N$_3$), 2.60-2.51 (m, 3H), 2.41 (dd, J=4.8, 15.2 Hz, 1H), 2.30-2.26 (m, 4H), 2.19 (1.62-1.44 (m, 8H), 1.38-1.25 (m, 86H), 0.94-0.88 (t, 12H). $^{13}$C NMR (CDCl$_3$, 100 MHz): δ 174.6, 172.3, 171.7, 171.5, 154.3, 138.9, 138.7, 138.3, 138.0, 128.7, 128.5, 128.2, 128.0, 127.9, 127.5, 101.3, 97.7, 95.7, 76.7, 75.7, 75.5, 75.4, 74.7, 73.9, 71.6, 71.2, 70.8, 70.5, 70.2, 67.7, 67.2, 55.8, 52.1, 50.4, 42.1, 40.3, 40.1, 36.9, 34.9, 34.7, 34.4, 34.3, 32.4, 32.2, 30.1, 29.9, 29.7, 29.6, 26.7, 25.4, 25.2, 24.9, 23.6, 22.9, 14.4. HR RSI MS (m/z): calcd. for C$_{101}$H$_{159}$Cl$_3$N$_5$O$_{18}$Na (M+Na)$^+$, 1855.0409; found, 1855.0339.

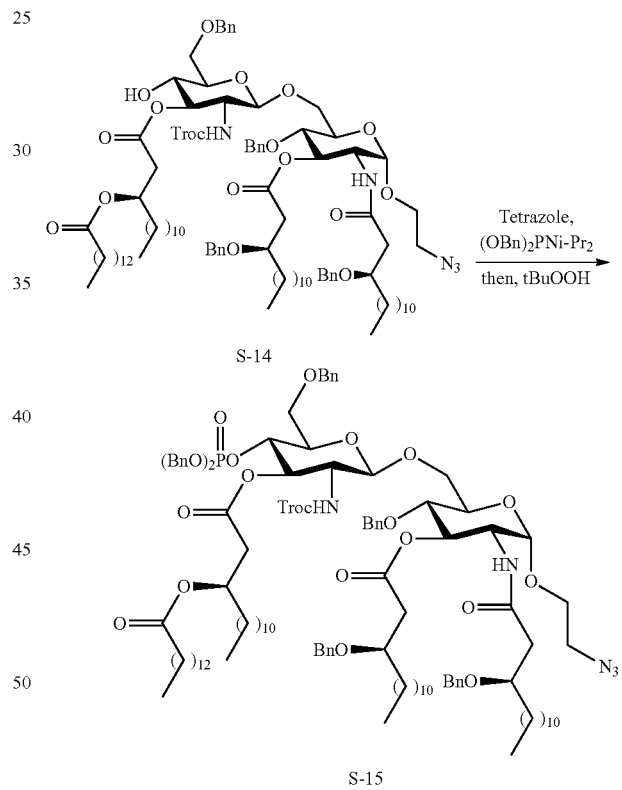

S-15

Compound S-15.

To a stirred solution of S-14 (50 mg, 0.027 mmol) in dry DCM (5 mL) were added 1H-tetrazole (0.45M, 0.5 mL) and dibenzyl diisopropylphosphoramidite (0.05 mL, 0.15 mmol). After the mixture was stirred for 2 hours at room temperature, it was cooled to −30° C. and then t-BuOOH (0.4 mmol) was added. The mixture was stirred for another 0.5 hour at 0° C. The solution was washed with saturated aqueous NaHCO$_3$ and brine. The organic phase was dried and concentrated. The residue was purified by flash chromatography to give S-15 as syrup (43 mg, 75%). $[\alpha]_D$ +5.2 (c 0.5, CHCl$_3$). $^1$H NMR (CDCl$_3$, 400 MHz): δ 7.36-7.22 (m, 30H), 6.10 (d, J=9.6 Hz, 1H, NH), 5.45 (d, J=8.4 Hz, 1H, NH'), 5.38-5.32 (m, 2H, H-3, H-3'), 5.18 (m, 1H, lipid), 4.90-4.80 (m, 4H, 2 PhC$\underline{H}_2$), 4.71 (d, J=3.2 Hz, 1H, H-1), 4.65-4.58 (m, 3H, H-1', PhC$\underline{H}_2$), 4.54-4.38 (m, 8H, H-4', Troc, PhC$\underline{H}_2$), 4.29-4.24 (m, 1H, H-2), 4.06-4.03 (m, 1H, H-6b), 3.85-3.77 (m, 4H, 2 BnOC$\underline{H}$, H-5, H-6a'), 3.69-3.56 (m, 5H, H-4, H-5', H-6a), 3.54-3.45 (m, 1H, H-2'), 3.44-3.38 (m, 1H, OC$\underline{H}_2$CH$_2$N$_3$), 3.26-3.17 (m, 2H, OC$\underline{H}_2$CH$_2$N$_3$), 3.10-3.04 (m, 1H, C$\underline{H}_2$N$_3$), 2.55 (dd, J=7.2, 16.0 Hz, 1H), 2.47-2.33 (m, 1H), 2.29-2.21 (m, 5H), 1.94-1.87 (m, 1H), 1.62-1.44 (m, 8H), 1.38-1.25 (m, 86H), 0.94-0.88 (t, 12H). $^{13}$C NMR (CDCl$_3$, 100 MHz): δ 173.9, 172.2, 171.4, 170.5, 154.2, 138.9, 138.8, 138.3, 138.2, 135.7, 129.7, 128.8, 128.6, 128.3, 128.1, 127.8, 127.6, 100.6, 97.8, 95.5, 76.6, 75.7, 74.7, 74.6, 74.4, 73.6, 72.5, 71.6, 70.8, 70.5, 70.3, 69.8, 68.8, 68.1, 67.6, 67.1, 56.7, 52.1, 50.4, 42.1, 40.0, 39.8, 36.9, 34.7, 34.4, 34.3, 32.2, 29.9, 29.6, 29.4, 26.7, 25.4, 24.9, 23.7, 23.2, 22.9, 14.3. $^{31}$P NMR (CDCl$_3$): δ −0.92. HR ESI MS (m/z): calcd. for C$_{115}$H$_{169}$Cl$_3$N$_5$O$_{21}$PNa (M+Na)$^+$, 2115.1011; found, 2115.0942.

which was then dissolved in DCM (1.5 mL). To this solution was added EDC (1-ethyl-3-(3-dimethylaminopropyl) carbodiimide) (9 mg, 0.048 mmol) and S-17 (7 mg, 0.072 mmol) in DCM (3 mL). The reaction mixture was stirred for 2 hours at room temperature. The mixture was diluted with DCM and washed with brine. The organic phase was dried, concentrated and the residue was purified by silica gel column chromatography to afford S-18 (30 mg, 58%). [α]$_D$ +9.2 (c 0.65, CHCl$_3$). $^1$H NMR (CDCl$_3$, 400 MHz): δ 7.32-7.20 (m, 30H), 6.28 (d, J=9.6 Hz, 1H, NH), 5.94 (s, 1H, NH), 5.68 (d, J=7.6 Hz, 1H, NH'), 5.42 (dd, J=9.6 Hz, 8.4 Hz, 1H, H-3'), 5.28 (dd, J=11.2, 8.4 Hz, 1H, H-3), 5.17 (m, 1H, lipid), 4.91-4.88 (m, 4H, PhC$\underline{H}_2$), 4.67-4.39 (m, 13H, H-1, H-1', H-4', Troc, PhC$\underline{H}_2$), 4.27-4.21 (m, 1H, H-2), 4.06-4.04 (m, 1H, H-6b), 3.91-3.76 (m, 4H, 2 BnOC$\underline{H}$, H-5, H-6a'), 3.63-3.53 (m, 5H, H-4, H-5', H-6a, OC$\underline{H}_2$CH$_2$NHCO), 3.45-3.41 (m, 1H, H-2'), 3.14-3.08 (m, 2H, OC$\underline{H}_2$CH$_2$NHCO), 3.00 (m, 1H, OCH$_2$C$\underline{H}_2$NHCO), 2.58-2.20 (m, 12H), 1.65-1.38 (m, 10H), 1.38-

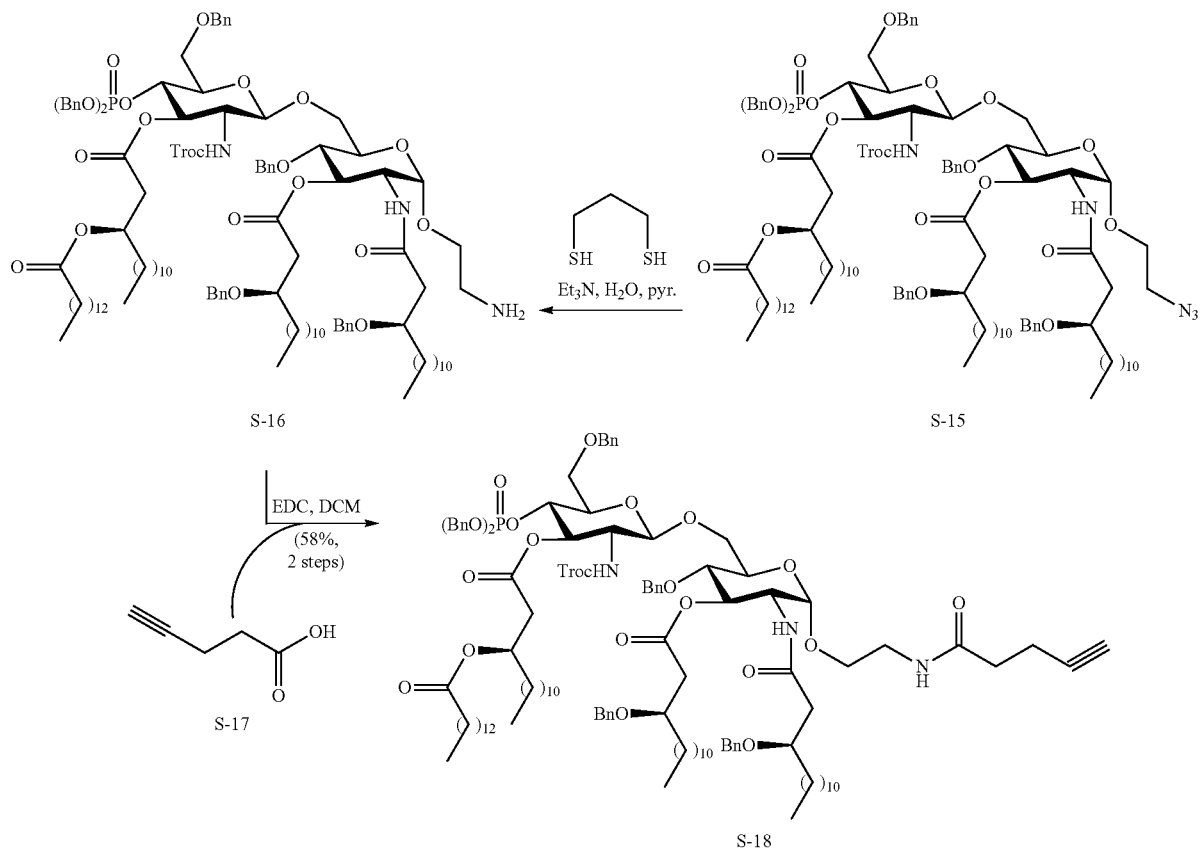

Compound S-18.

After triethylamine (0.2 mL) was added to a stirred solution of S-15 (50 mg, 0.024 mmol) and 1,3-propanedithiol (0.15 mL) in pyridine (4 mL) and H$_2$O (0.2 mL), the mixture was stirred at 0° C. until the starting material disappeared as monitored by TLC. The solvent was then evaporated in vacuum, and the residue was coevaporated with toluene (2 times, 10 mL) and ethanol (2 times, 10 mL). The residue was purified by silica gel column chromatography to give S-16, 1.25 (m, 90H), 0.87 (t, 12H); $^{13}$C NMR (CDCl$_3$, 100 MHz): δ 173.8, 172.3, 171.5, 170.4, 154.3, 138.8, 138.4, 138.3, 137.9, 135.7, 128.8, 128.6, 128.3, 127.9, 127.8, 127.7, 127.6, 127.0, 100.4, 97.2, 95.5, 83.5, 77.1, 73.6, 72.3, 71.4, 71.2, 70.5, 70.3, 69.8, 68.8, 68.3, 67.6, 66.8, 56.7, 52.1, 41.9, 39.9, 39.6, 39.0, 35.2, 34.7, 34.4, 34.1, 32.2, 29.9, 29.8, 29.6, 29.4, 25.4, 25.2, 22.9, 15.0, 14.3. $^{31}$P NMR (CDCl$_3$): δ −0.91. HR ESI MS (m/z): calcd. for C$_{120}$H$_{175}$Cl$_3$N$_5$O$_{22}$PNa (M+Na)$^+$, 2169.1368; found, 2169.1301.

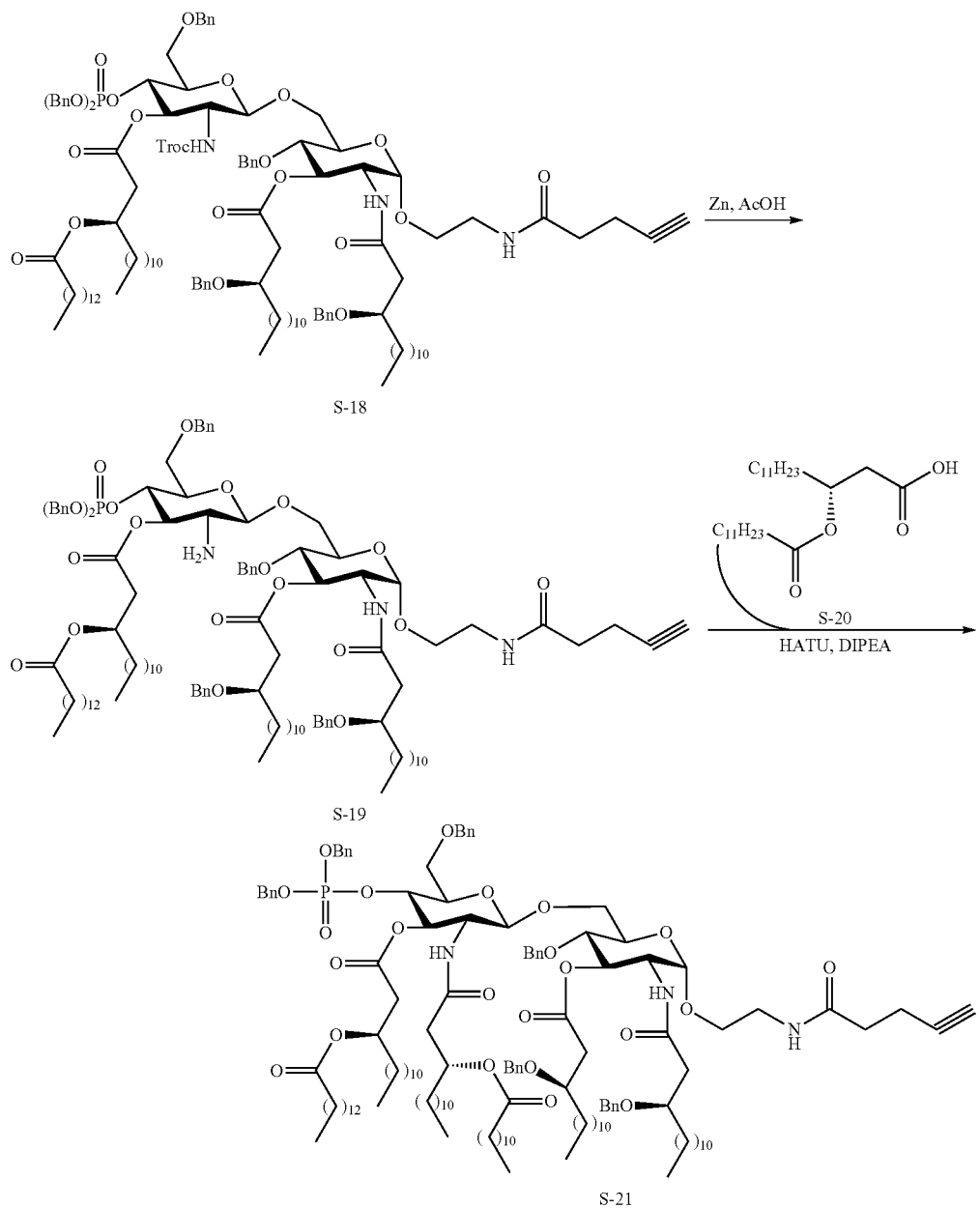

Compound S-21.

A solution of S-18 (52 mg, 0.024 mmol) in acetic acid (5 mL) was stirred with Zn powder (100 mg) at room temperature for 24 hours. The solid materials were removed by filtration over a Celite pad. The filtrate was concentrated and coevaporated with toluene 3 times. The residue was dissolved in $CH_2Cl_2$ (40 mL) and washed sequentially with saturated aq. $NaHCO_3$ solution (20 mL), $H_2O$ (10 mL), and brine (10 mL). The organic phase was dried and concentrated. The residue was purified by chromatography on silica gel to afford S-19 as a foamy solid. To the solution of S-20 (50 mg, 0.121 mmol) and DIPEA (diisopropylethylamine, 0.02 mL) in DMF (0.5 mL) was added a solution of HATU (2-(1-H-9-azabenzotriazole-1-yl)-1,1,3,3-tetramethyluronium hexafluorophosphate, 50 mg, 0.132 mmol) in DMF (0.2 mL), and the mixture was stirred under $N_2$ for 30 minutes. This solution was then added to a stirred solution of S-19 in DMF (0.5 mL), and the mixture was stirred under $N_2$ for 3.5 hours at 60° C. The mixture was diluted with DCM (50 mL) and washed sequentially with saturated aqueous. $NaHCO_3$ solution (10 mL), $H_2O$ (10 mL) and brine (3×20 mL). The organic phase was dried, concentrated, and the residue was purified by flash silica gel column chromatography to afford S-21 as a white solid (39 mg, 70%). $[\alpha]_D$ +16.4 (c 1.0, $CHCl_3$); $^1H$ NMR ($CDCl_3$, 400 MHz): δ 7.31-7.19 (m, 30H), 6.31 (d, J=9.2 Hz, 1H, NH), 6.25 (d, J=7.2 Hz, 1H, NH'), 5.41 (t, J=9.6 Hz, 1H, H-3'), 5.2 (t, J=9.6 Hz, 1H, H-3), 5.16 (m, 1H, lipid), 5.07 (m, 1H, lipid), 4.90-4.88 (m, 4H, PhC$\underline{H}_2$), 4.64 (d, J=4.0 Hz, 1H, H-1), 4.56-4.41 (m, 10H, H-1', H-4', 4PhC$\underline{H}_2$), 4.28-4.22 (m, 1H, H-2), 4.06-4.03 (m, 1H, H-6b), 3.88-3.75 (m, 4H, 2 ROC$\underline{H}$, H-5, H-6a'), 3.66-3.48 (m, 6H, H-4, H-5', H-6a, H-2', OC$\underline{H}_2$C$H_2$NHCO), 3.22-3.10 (m, 3H, OC$H_2$C$\underline{H}_2$NHCO), 2.56-2.19 (m, 15H), 2.13 (d, J=2.0 Hz, 1H), 1.55-1.42 (m, 12H), 1.24-1.03 (m, 116H), 0.98-0.88 (t, 18H); $^{13}C$ NMR ($CDCl_3$, 100 MHz): δ 173.8, 172.1, 171.5, 171.3, 170.5, 138.8, 138.5, 138.3, 137.7, 135.8, 128.8, 128.7, 128.5, 128.3, 128.2, 128.0, 127.9, 127.8, 127.7, 100.5, 97.3, 95.5, 83.7, 76.9, 76.1, 75.6, 74.7, 74.4, 73.8, 73.5, 72.7, 71.4, 71.2, 70.7, 70.4, 70.0, 69.8, 68.8, 62.0, 57.9, 52.2, 50.7, 41.9, 39.9, 35.2, 34.7, 34.5, 34.2, 32.2, 29.9, 29.6, 29.5, 29.5, 25.5, 25.4, 25.3, 22.9, 15.1, 14.4. $^{31}$P NMR (CDCl$_3$): δ −0.91. HR ESI MS (m/z): calcd. for C$_{143}$H$_{222}$N$_3$O$_{23}$PNa (M+Na)$^+$, 2403.5930; found, 2403.5903.

CHCl$_3$). $^1$H NMR (CDCl$_3$, 500 MHz): δ 7.45 (s, 1H), 7.19-6.90 (m, 35H), 5.24-5.21 (m, 1H, H-3'), 5.15-5.08 (m, 1H, H-3), 4.98 (m, 1H, lipid), 4.88 (m, 1H, lipid), 4.72-4.65 (m, 4H, PhC$\underline{H}_2$), 4.43 (d, J=3.5 Hz, 1H, H-1), 4.39-4.42 (m, 12H, H-1', H-4', PhC$\underline{H}_2$), 4.09 (d, J=7.0 Hz, 1H), 4.28-4.22 (m, 1H, H-2), 3.96 (m, 1H, H-6b), 3.78 (m, 1H), 3.68-3.35 (m, 4H, 2 ROC$\underline{H}$, H-5, H-6a'), 2.98-2.92 (m, 2H), 2.75 (m, 2H), 2.35-1.99 (m, 12H), 1.86-1.80 (m, 3H), 1.55-1.42 (m, 12H), 1.24-1.03 (m, 116H), 0.98-0.88 (t, 18H). $^{13}$C NMR (CDCl$_3$, 125

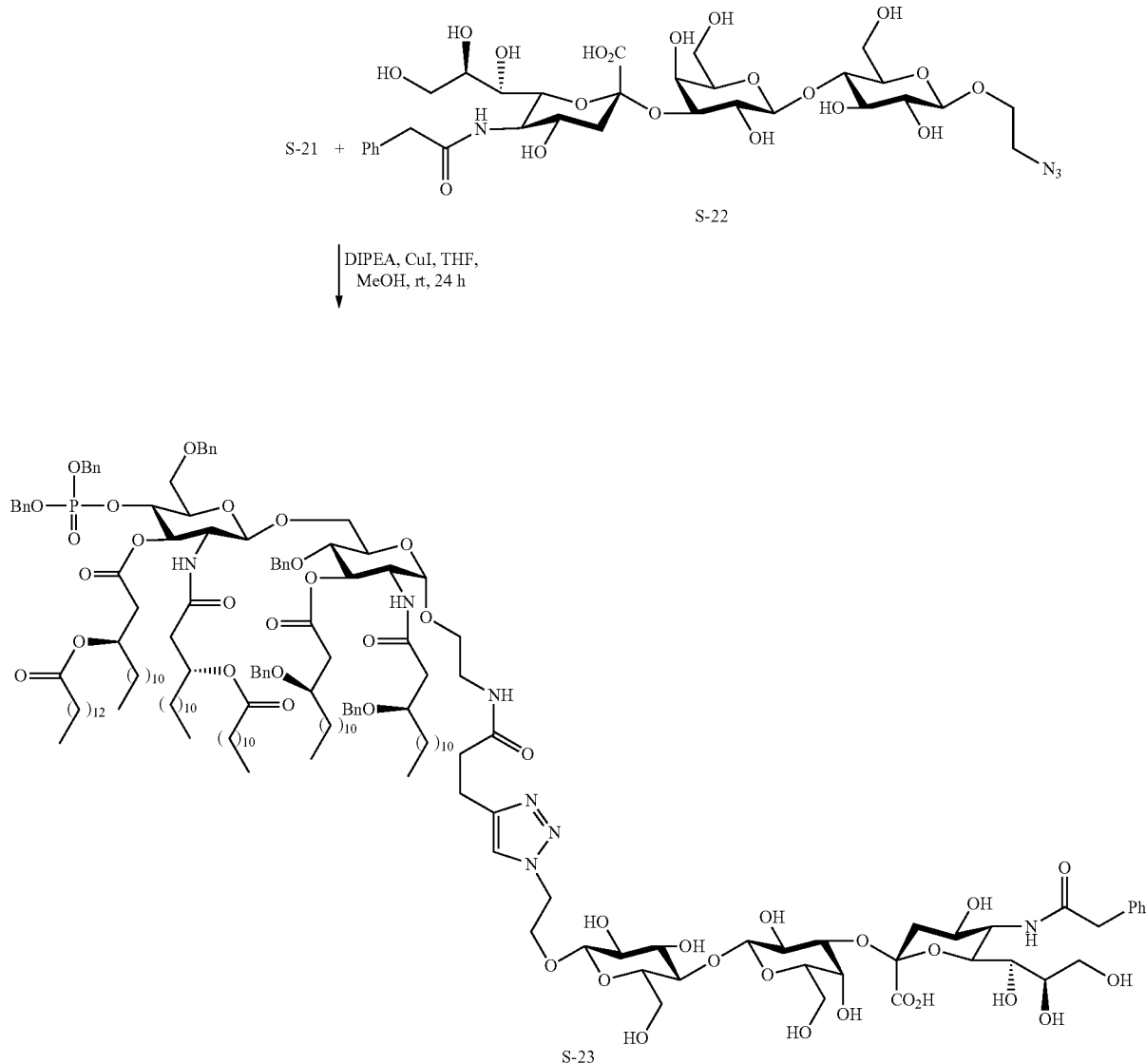

Compound S-23.

After S-21 (10 mg, 0.004 mmol), S-22 (4 mg, 0.005 mmol), and CuI (10 equivalents) were dissolved in MeOH/THF (2:1, 0.6 mL), DIPEA (10 equivalents) was added to the solution. After stirring for 24 hours at room temperature, the mixture was filtered though a Celite pad, and the solvent was evaporated in high vacuum. The crude product was then purified by flash silica gel column chromatography (eluent: from AcOEt: hexane=4:1 to AcOEt and then to MeOH:CH$_2$Cl$_2$ 5:1) to produce S-23 as a white solid (9 mg, 70%) [α]$_D$ 4.4 (c 0.45, MHz): δ 129.0, 128.7, 128.6, 128.4, 128.3, 128.2, 128.1, 128.0, 127.8, 127.7, 127.6, 127.5, 127.0, 123.2, 103.0, 100.2, 97.4, 77.6, 76.7, 75.9, 75.4, 75.0, 74.6, 74.5, 74.0, 73.4, 73.3, 73.1, 72.6, 71.5, 71.2, 70.6, 70.0, 69.8, 68.5, 68.0, 62.0, 57.9, 52.2, 51.7, 50.2, 49.3, 49.1, 49.0, 48.8, 48.6, 41.4, 39.6, 38.8, 35.1, 34.5, 34.2, 31.9, 29.6, 29.3, 29.2, 25.4, 25.1, 25.0, 22.7, 21.2, 13.9. $^{31}$P NMR: δ −1.50. MALDI-TOF MS (m/z): calcd. for C$_{174}$H$_{268}$N$_7$O$_{42}$P (M$^+$), 3158.9; found 3181.8 (M+Na)$^+$, 3203.8 (M−H+2Na)$^+$.

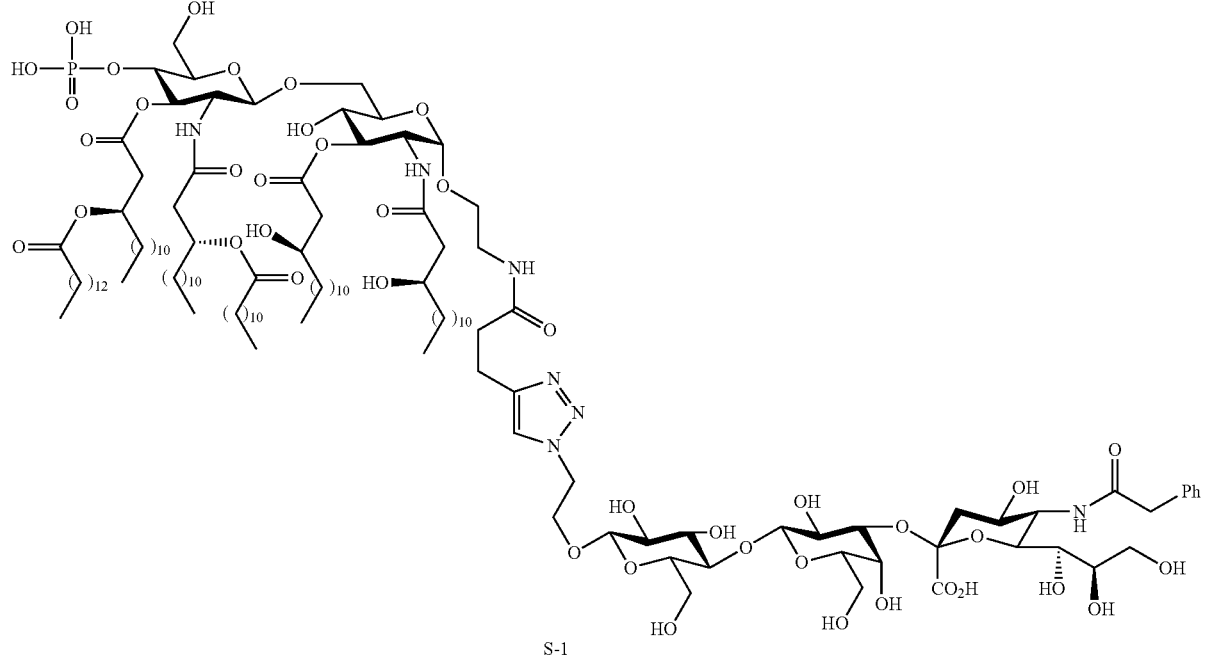

Compound S-1.

A solution of S-23 (9.0 mg, 0.0028 mmol) in 3:1 anhydrous THF/MeOH (2.8 mL) was hydrogenated in the presence of Pd—C (10%, 10 mg) at room temperature for 48 h. The catalyst was removed by filtration, and the residue was washed with THF and MeOH (5 mL). The combined filtrates were concentrated in vacuo to afford S-1 as a white solid (4.3 mg, 59%). $^1$H NMR (CDCl$_3$—CD$_3$OD, 500 MHz): δ 8.38 (s, 1H), 7.10-6.99 (m, 5H), 5.34-5.31 (m, 1H), 5.22-5.14 (m, 3H, H-3, PhC$\underline{H}_2$), 5.12-4.85 (m, 3H, 2lipid, H-3'), 4.40-4.22 (m, 4H), 4.09 (d, J=7.0 Hz, 1H), 3.94 (m, 1H, H-6b), 3.71 (m, 1H), 3.70-3.59 (m, 4H, 2 HOC$\underline{H}$, H-5, H-6a'), 3.54-3.33 (m, 4H), 3.05-2.98 (m, 2H), 2.36-2.31 (m, 2H) 2.25-2.14 (m, 2H), 2.07-1.99 (m, 8H), 1.83-1.75 (m, 3H), 1.63-1.58 (m, 2H), 1.51-1.39 (m, 6H) 1.23-0.92 (m, 108H), 0.69-0.66 (t, 18H).

Compound T-2.

A solution of 13 (10 mg, 4.75 μmol), HOBt (N-Hydroxybenzotriazole)(12.8 mg, 95 μmol) and DIC (diisopropylcarbodiimide)(12 mg, 95 μmol) in DCM/DMF (dichorlomethane/dimethylformamide) (5:2 v/v, 1.4 mL) was stirred under argon at room temperature for 15 minutes. Propargylamine (5.3 mg, 95 μmol) and DIPEA (diisopropylethylamine)(16 μL, 95 μmol) was added and the mixture was kept in dark at room temperature for overnight. The mixture was diluted with toluene and concentrated to dryness under reduced pressure. The residue was purified by flash column chromatography to give the compound T-2 as a white solid (7.8 mg, 77%). $^1$H NMR (400 MHz, CDCl$_3$): δ 7.30-7.22 (m, 20H), 6.74 (m, 1H, OCH$_2$CH$_2$N$\underline{H}$"), 6.70 (s, 1H, N$\underline{H}$CH$_2$CCH), 6.60 (m, 1H, NH'), 6.09 (d, J 8.8 Hz, 1H, NH), 5.45 (t, J 9.6 Hz, 1H, H-3'), 5.06-4.03 (m, 3H, H-3 and 2H from lipid), 4.90-4.85 (m, 4H, (PhC$\underline{H}_2$O)$_2$P=O), 4.80 (d, J 8.0 Hz, 1H, H-1'), 4.57-4.41 (m, 5H, H-4', 2×PhC$\underline{H}_2$), 4.39 (d, J 8.0 Hz, 1H, H-1), 4.07-3.93 (m, 2H, H-2, H-6), 3.80-3.74 (m, 2H, H-2', H-6'), 3.70-3.62 (m, 5H, OC$\underline{H}_2$CH$_2$NH", H-5', H-6, H-6'), 3.48-3.42 (m, 3H, OCH$_2$C$\underline{H}_2$NH", H-5, H-4), 3.42-3.33 (m, 2H, OC$\underline{H}_2$CH$_2$NH"), 2.52-2.42 (m, 10H, C(=O)C$\underline{H}_2$CH$_2$CONH, lipid, NHC$\underline{H}_2$CCH), 2.30-2.03 (m, 8H, lipid), 1.64-1.35 (m, 10H, lipid), 1.40-1.03 (br, 104H, 52×CH$_2$, lipid), 0.87 (t, J 5.4 Hz, 18H, 6×CH$_3$, lipid); $^{13}$C NMR (125 MHz, CDCl$_3$): δ 173.9, 173.8, 173.7, 172.5, 170.1, 170.0, 138.3, 137.7, 135.8, 128.8, 128.7, 128.6, 128.2, 128.1, 128.0, 127.9, 127.8, 101.6, 100.9, 80.0, 76.7, 75.0, 74.8, 74.7, 74.6, 74.2, 73.6, 72.4, 71.8, 71.5, 71.2, 69.9, 69.8, 69.7, 68.9, 68.7, 68.3, 55.0, 54.0, 42.0, 41.5, 40.3, 34.8, 34.4, 34.2, 32.2, 29.9, 29.8, 29.7, 29.6, 29.5, 29.4, 25.6, 25.4, 25.3, 25.0, 24.8, 22.9, 14.3; $^{31}$P NMR: δ −1.08; HR ESI MS (m/z): [M+Na]$^+$ calcd. for C$_{125}$H$_{201}$N$_4$NaO$_{22}$P, 2164.4368; found 2164.4375.

Compound T-3.

To the stirred solution of compound T-2 (7.8 mg, 3.6 μmol), S-22 (4.2 mg, 5.5 μmol) and CuI (13.8 mg, 73 μmol) in MeOH/THF (2:1, 0.6 mL), DIPEA (12 μL, 73 μmol) was added. After the mixture was stirred at room temperature for 24 hours, it was filtered over CELITE® (diatomaceous earth) and the filtrate was evaporated under reduced pressure. The residue was purified by flash column chromatography (AcOEt/hexane 4:1, then CH$_2$Cl$_2$/MeOH 5:1) to afford compound T-3 (6.8 mg, 64%). $^1$H NMR (500 MHz, CDCl$_3$/CD$_3$OD): δ 7.76 (s, 1H), 7.18-7.09 (m, 25H), 5.27 (t, J=10.0 Hz, 1H, H-3'), 5.03-4.91 (m, 3H, H-3, and 2H from lipid), 4.81-4.74 (m, 4H, (PhC$\underline{H}_2$O)$_2$P=O), 4.66 (d, J 8.0 Hz, 1H, H-1'), 4.48-4.40 (m, 2H, PhC$\underline{H}_2$), 4.36-4.33 (m, 3H, H-4', Ph C$\underline{H}_2$), 4.32 (d, J 8.0 Hz, 1H, H-1"), 4.28 (d, J 9.0 Hz, 1H, H-1), 4.17 (d, J 7.5 Hz, 1H, H-1"'), 3.97-3.94 (m, 2H, H-6), 3.88-3.43 (m, 31H), 3.28-3.18 (m, 5H), 2.40-2.34 (m, 6H), 2.26 (dd, J 15.0, 6.0 Hz, 1H, H-3"e of GM$_3$), 2.19-1.89 (m, 11H, lipid and H-3"a of GM$_3$), 1.43-1.36 (m, 10H, lipid), 1.30-1.11

(br, 104H, 52×CH$_2$, lipid), 0.86-0.74 (m, 18H, 6×CH$_3$, lipid); $^{13}$C-DEPT NMR (125 MHz, CDCl$_3$-CD$_3$OD): δ 174.0, 137.6, 129.1, 128.8, 128.6, 128.5, 128.4, 128.0, 127.8, 127.7, 127.6, 127.1, 103.9, 102.9, 101.2, 77.6, 77.0, 76.5, 76.1, 75.4, 74.6, 74.6, 74.2, 73.9, 73.7, 73.4, 73.4, 72.4, 72.3, 71.2, 70.9, 69.9, 69.6, 69.2, 68.8, 68.5, 68.1, 67.5, 61.7, 60.9, 54.4, 53.7, 52.7, 49.6, 49.1, 48.9, 42.8, 41.1, 40.9, 39.6, 39.4, 34.6, 34.2, 34.0, 32.0, 31.0, 30.9, 29.7, 29.6, 29.4, 29.3, 25.4, 25.1, 24.8, 24.6, 22.7, 14.1; $^{31}$P NMR: δ −1.62; MALDI TOF MS (m/z): [M+Na]$^+$ calcd. for C$_{156}$H$_{246}$N$_8$NaO$_{41}$P, 2918.7108; found 2919.286.

Compound T-1.

The same procedure as that for the synthesis of compound 1 and S-1. T-1 was used directly for mice immunization.

2. *N. meningitidis* Monophosphoryl Lipid A-GM3NPhAc Conjugates as Cancer Vaccines Materials.

Compounds 1, 2, and T-1, cholesterol, 1,2-distearoyl-sn-glycero-3-phosphocholine (DSPC), GM3NPhAc-HSA (Pan, Y., Chefalo, P., Nagy, N., Harding, C. and Guo, Z. *J Med Chem* 48, 875-83 (2005)), TiterMax® Gold adjuvant (sigma-aldrich), alkaline phosphatase linked goat anti-mouse kappa, IgM, IgG1, IgG2a and IgG3 antibodies (southern biotechnology), female C57BL/6 mice (6-8 weeks old, jackson laboratory).

Methods.

1) Form liposome: As conjugates 1, 2, and T-1 are highly hydrophobic, they were incorporated into phospholipid-based liposomes before immunization. Compounds 1, 2, or T-1, 1,2-distearoyl-sn-glycero-3-phosphocholine and cholesterol (molar ratios, 10:65:50) were dissolved in a mixture of CH$_2$Cl$_2$ and MeOH (1:1, v/v, 2 ml). The solvents were removed in vacuo to give a thin lipid film, which was hydrated by shaking in HEPES buffer (20 mM, pH 7.5, containing NaCl (150 mM)) under argon atmosphere at 40° C. for 1 hour. The suspension was then sonicated for 1 minute to obtain liposomes.

2) Immunization of mice: Groups of five mice were immunized subcutaneously four times on day 0, 14, 21 and 28 with 0.1 mL of liposomes of individual MPLA-GM3 conjugates, or with total 0.1 mL of the emulsion of individual MPLA-GM3 conjugates solution and TiterMax® Gold adjuvant containing 15, 6, or 3 μg of GM3 derivatives. The mice were bled prior to the initial immunization on day −1 and after immunization on day 27 and day 38. Blood samples of each mouse collected on each date were clotted to obtain serum and stored at −80° C. before use.

3) Enzyme-linked immunosorbent assay (ELISA): ELISA plates were first treated with 100 μL of a GM3NPhAc-HSA solution (2 μg/mL) in the coating buffer (0.1 M bicarbonate, pH 9.6) at 37° C. for 1 hour, followed by blocking with blocking buffer and then washing 3 times with PBS containing 0.05% Tween-20 (PBST). Then, pooled or individual mice sera from each immunized group were diluted 1:300 to 1:656, 100 in serial half-log dilutions in PBS and incubated at 37° C. for 2 hours in the coated ELISA plates (100 μL/well). The plates were washed with PBST and incubated at room temperature for 1 hour with 1:1000 dilution of alkaline phosphatase linked goat anti-mouse kappa, IgM or IgG2a antibody or with 1:2000 dilution of alkaline phosphatase linked goat anti-mouse IgG1 or IgG3 antibody (100 μL/well). Finally, plates were washed and developed with 100 μL of PNPP (p-Nitrophenyl phosphate) solution (1.67 mg/mL in PNPP buffer) for 30 minutes at room temperature for colorimetric readout using a BioRad 550 plate reader at 405 nm wavelength.

For titer analysis, optical density (OD) values were plotted against dilution values, and a best-fit line was obtained. The equation of this line was employed to calculate the dilution value at which an OD of 0.2 was achieved, and the antibody titer was calculated at the inverse of this dilution value.

Results.

As shown in FIG. 1a, mice immunized with liposome of 1 alone (1N) containing 15 μg of GM3NPhAc induced kinetically very strong anti-GM3NPhAc immune response. The immune response was also dose-dependent and application of 6 μg, or even 3 μg of GM3NPhAc still results in high antibody titers (FIG. 1b). Immunization of mice with 1 plus external adjuvant (FIG. 1c, group 1A) also induced GM3NPhAc-specific immune response, but to a much lower extent, which may be due to the interference of some adjuvant contents with the immunological process induced by 1. Mice were also immunized with conjugate 2, the benzyl protected form of 1. The analysis of mice sera showed that 2 is not immunogenic at all no matter inoculated alone (FIG. 1c, group 2N) or together with an external adjuvant (FIG. 1c, group 2A), which indicated that the free form of phosphate in MPLA moiety is necessary for the immunological activities of the conjugate vaccines.

The immune response induced by liposome of T-1 containing 15 μg of GM3NPhAc was comparable to that induced by 1 with same dose of GM3NPhAc (FIG. 1c, group T-1N). Because the only difference between 1 and T-1 is the linker, the comparable immune response induced by liposome of 1 and T-1 indicated that both linkers used to couple *N. meningitidis* MPLA to GM3NPhAc are immunologically inert and can be safely used for the development of glycoconjugate vaccines. It was also concluded that the high immunogenicity of GM3NPhAc in 1 and T-1 are mainly attributed to the immunostimulatory properties of MPLA, but not the linker.

Figure 2:
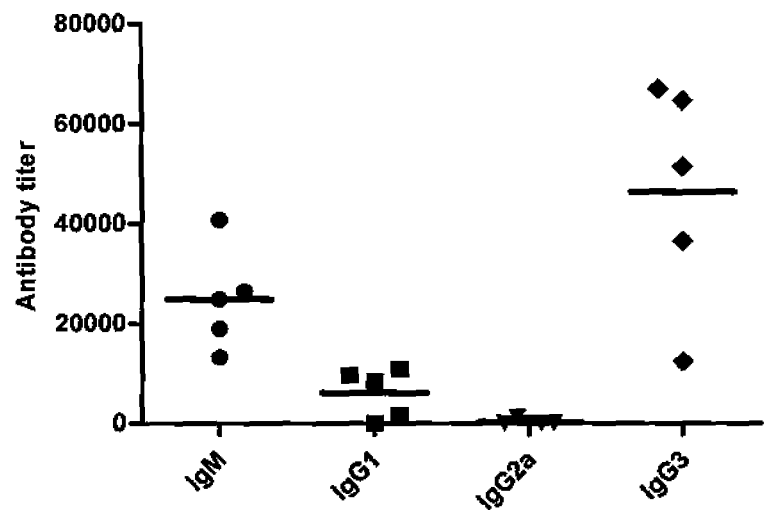
FIG. 2 relates to the titer analysis of different isotypes of GM3NPhAc-specific antibodies induced by 1N (left) and T-1N (right). Goat anti-mouse IgM, IgG1, IgG2a and IgG3 antibodies were used to detect antibodies bond to the capture antigen, GM3NPhAc-HSA. Titers are determined by linear regression analysis and defined as the highest dilution yielding an optical density of 0.2. Each dot represents the GM3NPhAc-specific immune response of individual mouse and the black lines represent the average antibody level of a group of five mice.
Figure 2:
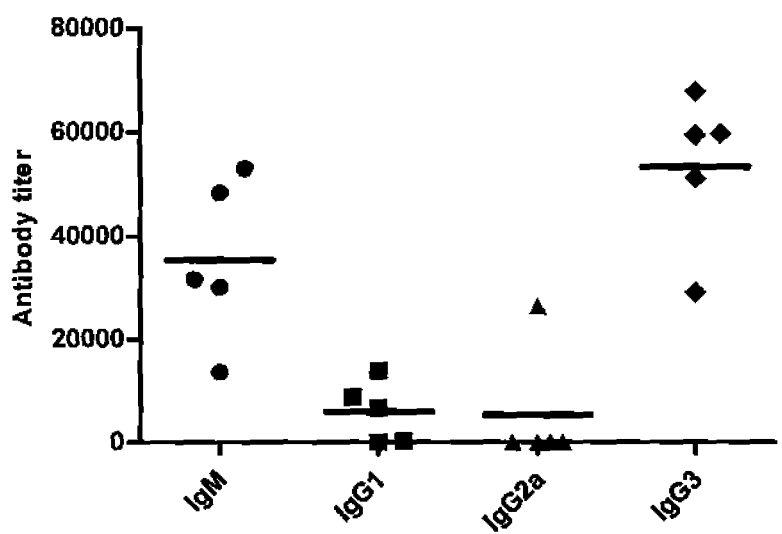

The antibody isotypes in day 38 mice sera of conjugates 1 and T-1 were examined following the same ELISA protocol but using alkaline phosphatase linked goat anti-mouse IgM, IgG1, IgG2a, and IgG3 as second antibodies. It was found that mice immunized with 1 and T-1 produce not only GM3NPhAc-specific IgM and IgG1 antibodies, but also much higher titers of IgG3 antibody, which is typical of an anti-carbohydrate response (Perlmutter, R. M., Hansburg, D., Briles, D. E., Nicolotti, R. A. & Davie, J. M. *J Immunol* 121, 566-72 (1978); Greenspan, N. S. & Cooper, L. J. *Immunol Today* 13, 164-8 (1992)) (FIG. 2). The existence of IgG1 and IgG3 antibodies in mice sera also demonstrated the efficiency of MPLA-GM3NPhAc conjugates in the generation of Th cell-mediated immunity.

The immunological studies of MPLA-GM3NPhAc conjugates 1 and T-1 revealed that MPLA is a powerful built-in immunostimulant and adjuvant in activation of Th cell-mediated immune response against GM3NPhAc. The promising vaccine candidates, MPLA-GM3NPhAcs, are potentially useful in an immunotherapeutic strategy in which glycoconjugate vaccines made of unnatural TACA analogs are combined with glycoengineering of TACAs on cancer cells.

3. In Vitro Glycoengineered Expression of GM3NPhAc on Cell Surface

Materials.

ManNPhAc, NeuNPhAc, murine melanoma cell B16F0, human melanoma cell SKMEL-28, murine normal fibroblast cell 3T3 A31, anti-GM3NPhAc mAb (2H3) ((Wang et al.

(2007) *Bioorg Med Chem.* 15(24): 7561-7567) and FITC-conjugated goat anti-mouse kappa antibody.

Methods.

B16F0, 3T3 A31 and SKMEL-28 cells were incubated with 0.01, 0.02 and 0.04 mM of ManNPhAc or NeuNPhAc, harvested at different time, washed with FACS buffer (phosphate-buffered saline (PBS) containing 1% bovine serum albumin), and incubated on ice for 15 minutes with 100 μL of normal mouse serum (NMS) diluted 1:100 in FACS buffer. Cells were washed 3 times with FACS buffer, and incubated for 30 minutes on ice with 100 μL of anti-GM3NPhAc mAb 2H3 (cell culture supernatant) diluted 1:10 in FACS buffer. Cells were washed again (3 times) and incubated for 30 minutes on ice with 1 μg of FITC-conjugated goat anti-mouse kappa antibody diluted in FACS buffer (100 μL). After washing 3 times with FACS buffer, the expression of GM3NPhAc on cell surfaces was evaluated on a Becton Dickenson FACScan flow cytometer. Data are presented as raw histograms derived from 20000 events.

Results.

Figure 3:
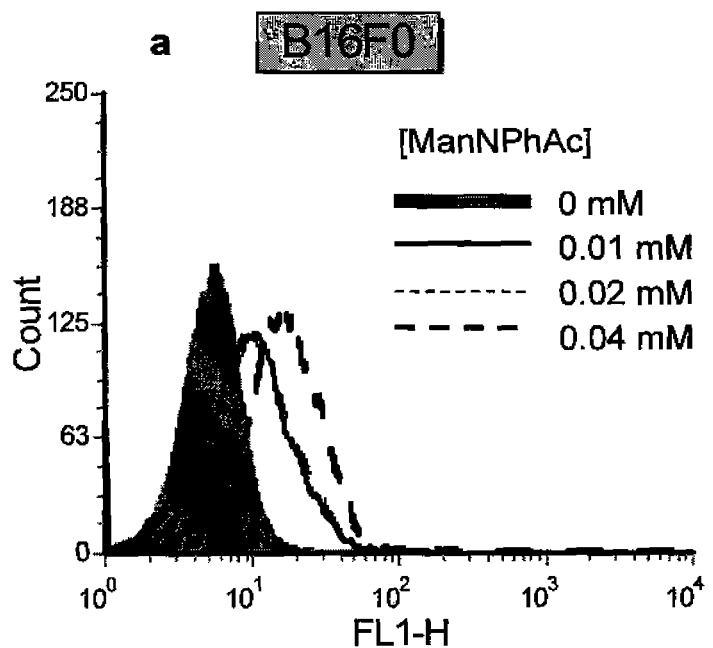
FIG. 3 depicts histograms of the glycoengineering of B16F0 cells (a), 3T3 A31 cells (b) and SKMEL-28 cells (c) using ManNPhAc which induces expression of GM3NPhAc on the cell surface. Cells were cultured with 0, 0.01, 0.02 and 0.04 mM of ManNPhAc, stained with mAb 2H3, labeled with FITC-labeled goat anti-mouse kappa antibody, and analyzed by flow cytometry. Data are presented as raw histograms derived from 20,000 events.
Figure 3:
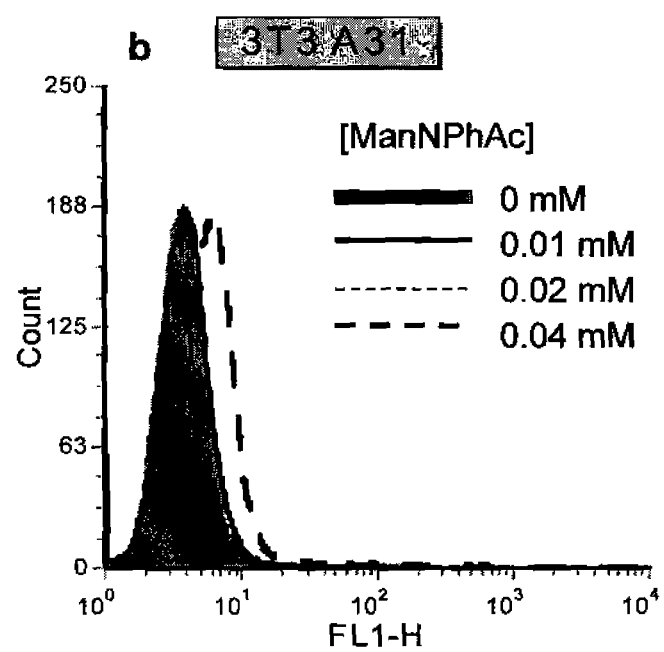
Figure 3:
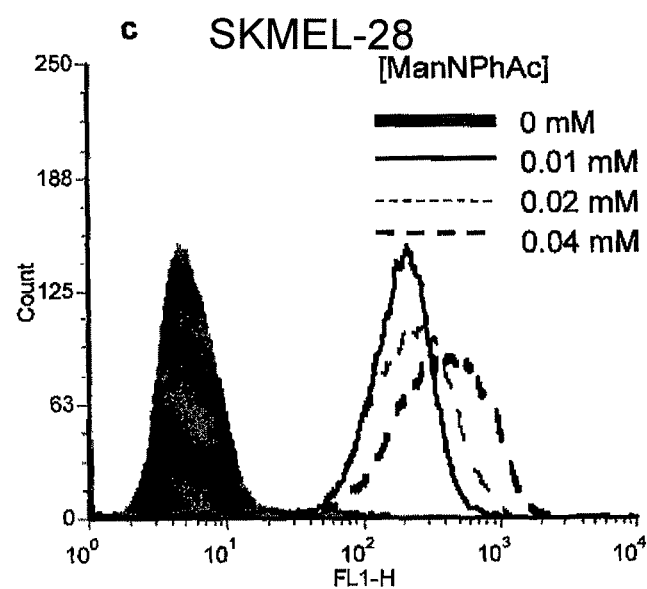

As shown in FIG. 3a, incubation of B16F0 cells with 0.01 mM of ManNPhAc for 72 hours resulted in significant expression of GM3NPhAc and the expression of GM3NPhAc was dependent on ManNPhAc concentrations. As for 3T3 A31 cell, compared to the control group, no substantial labelling for GM3NPhAc was found when cells were incubated with 0.01 and 0.02 mM of ManNPhAc. Cells started to show labelling with the concentration of ManNPhAc increased up to 0.04 mM, but it was only comparable to that on B16F0 cells incubated with 0.01 mM of ManNPhAc (FIG. 3b). The results concerning SKMEL-28 cell treated with different concentrations of ManNPhAc for 96 hours are shown in FIG. 3c. Incubation of SKMEL-28 cell with even 0.01 mM of ManNPhAc resulted in 100% of cells showing significant GM3NPhAc labelling above the control group, while under the same concentration of ManNPhAc, only partial B16F0 cell and no 3T3 A31 cell showing labelling of GM3NPhAc. The expression of GM3NPhAc on SKMEL-28 cell was further increased with 0.02 and 0.04 mM of ManNPhAc, and actually a plateau level of GM3NPhAc expression was reached when cells were incubated with 0.04 mM, or up, of ManNPhAc (data not shown).

Figure 4:
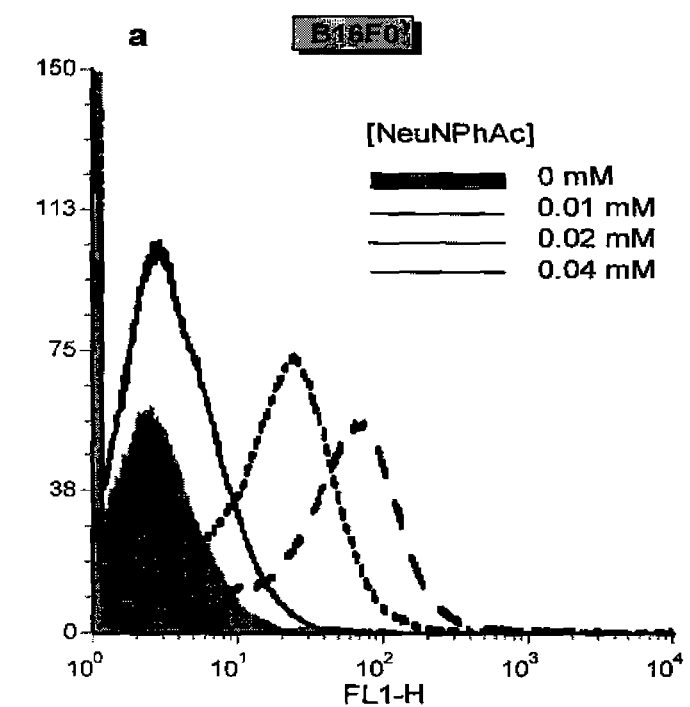
FIG. 4 depicts histograms of the glycoengineering of B16F0 (a) and 3T3 A31 (b) using NeuNPhAc induces expression of GM3NPhAc on the cell surface. Cells were cultured with 0, 0.01, 0.02 and 0.04 mM of NeuNPhAc, stained with mAb 2H3, labeled with FITC-labeled goat anti-mouse kappa antibody, and analyzed by flow cytometry. Data are presented as raw histograms derived from 10,000 events.
Figure 4:
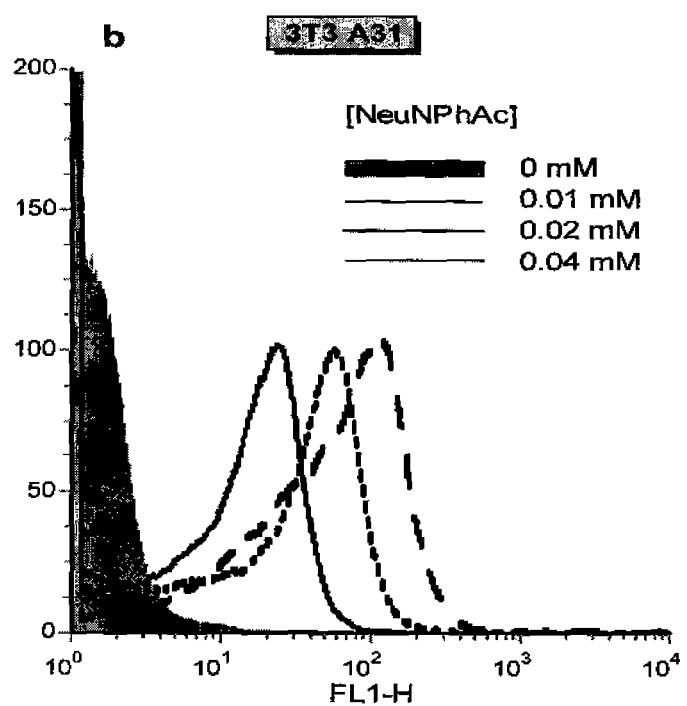

GM3NPhAc expression on B16F0 and 3T3 A31 cells incubated with NeuNPhAc was also evaluated by flow cytometry. It was found that incubation of B16F0 cells with NeuNPhAc for 72 hours resulted in more significant expression of GM3NPhAc than that incubated with ManNPhAc at the same concentrations (FIG. 4a). However, normal cell 3T3 A31 can also utilize NeuNPhAc much more efficiently to express GM3NPhAc, even better than B16F0 cancer cells (FIG. 4b).

4. In Vivo Glycoengineering of GM3NPhAc for Suppressing Melanoma Cells Metastasis Materials.

ManNPhAc, GM3NPhAc-KLH/HSA, murine melanoma cell B16F0, female C57BL/6 mice (6-8 weeks old), Titermax Gold adjuvant.

Methods.

C57BL/6 mice were divided into 3 groups. Two groups were immunized into 3 intramuscular sites with total 0.1 mL of the emulsion of GM3NPhAc-KLH and Titermax Gold adjuvant containing 3 μg of GM3NPhAc on day 0, 14, 21 and 28. The remaining one group was injected with 0.1 mL of the emulsion of PBS and adjuvant using as control. 3 or 4 days after final booster, all mice were inoculated into tail vein with $1 \times 10^5$ or $2 \times 10^5$ of B16F0 tumor cells, in 0.2 mL of DMEM. Simultaneously, ManNPhAc (2 mg/mouse in 0.5 mL PBS) was intraperitoneally given to one of GM3NPhAc-KLH immunized group (Vaccine-ManNPhAc) and PBS (0.5 mL) was given to the other two groups (Vaccine-PBS and control) for consecutive two weeks. The mice lungs were then removed, rinsed with PBS, and fixed in 10% buffered formalin phosphate solution. The number of B16F0 nodules on both sides of lungs was determined under a dissecting microscope. Statistical differences between groups were examined by unpaired Student's t tests. A value of p<0.05 was considered statistically significant.

Results.

Figure 5:
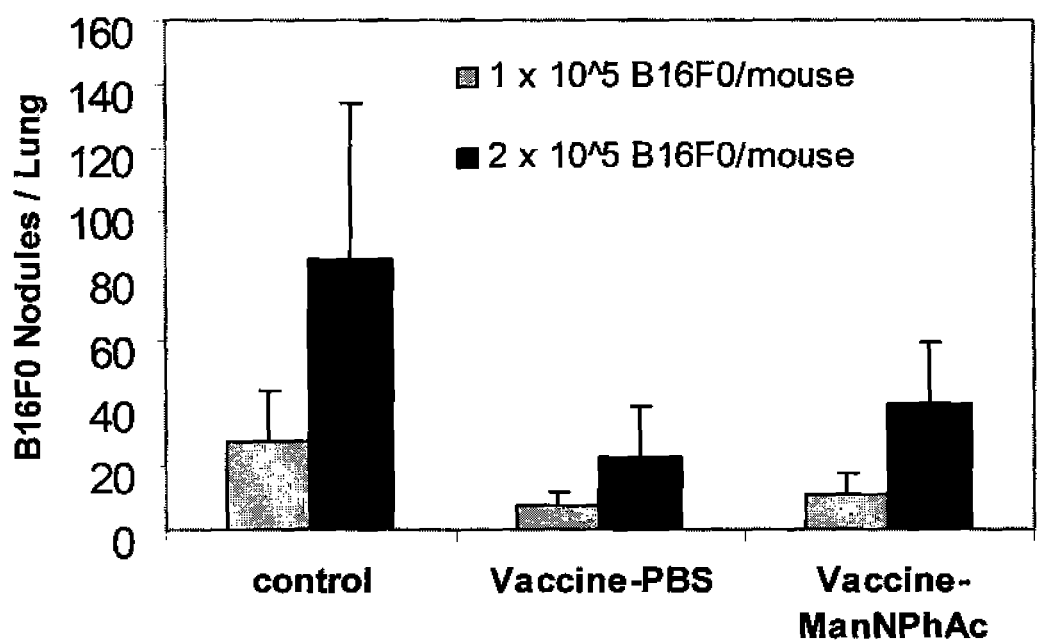
FIG. 5 relates to the inhibition of B16F0 lung metastasis by a GM3NPhAc-KLH vaccine. Mice were first immunized with GM3NPhAc-KLH or PBS, then inoculated i.v. with $1 \times 10^5$ or $2 \times 10^5$ B16F0 tumor cells. ManNPhAc (2 mg/mouse) or PBS was simultaneously intraperitoneally given for consecutive two weeks. Each column represents the mean+STDEV (n=5-10). *, p<0.05 vs control.

As shown in FIG. 5, when given $2 \times 10^5$ cells/mouse, the average number of B16F0 nodules on lungs is 85±49 for control group, 23±16 for vaccine-PBS group and 40±19 for vaccine-ManNPhAc group. Statistical differences between groups were examined by unpaired Student's t tests. It was found that application of GM3NPhAc-KLH vaccine alone results in halting metastasis of B16F0 cells in mice (p is 0.026 vs control). Concurrent application of GM3PhAc-KLH vaccine and ManNPhAc, although has effectiveness, to some extent, in halting metastasis of B16F0 cells in mice, no statistical significance was observed when compared with the control group (p is 0.09 vs control). The results also showed that ManNPhAc seems, to some extent, can help to facilitate the tumor metastasis although no difference between vaccine-PBS and vaccine-ManNPhAc groups (p is 0.174). Inoculation of less B16F0 cells ($1 \times 10^5$ cells/mouse) results in less tumor nodules on lungs, 40±40 for control group, 10±9 for vaccine-PBS group and 18±15 for vaccine-ManNPhAc group. The statistical results were same as those of inoculation of $2 \times 10^5$ cell/mouse, that is, no difference between vaccine-ManNPhAc and control group (p is 0.086), while difference was found for vaccine-PBS and control group (p is 0.016).

The results could be explained by Varki and co-workers' findings that the combination of tumor-associated Neu5Gc and circulating anti-Neu5Gc antibodies promotes tumor growth by the resulting chronic inflammation; and that high levels of antibody administration could instead inhibit tumor growth (Hedlund et al. *Proc. Natl. Acad. Sci., U.S.A.*, (2008), 18936-18941). In the present case, since GM3NPhAc-KLH vaccine already induced mice producing strong specific immune responses to GM3NPhAc, the low level expression of GM3NPhAc on B16F0 cell in vivo by administration of ManNPhAc may contribute to the deviant antimetastatic results. By using more efficient glycoengineering precursor, NeuNPhAc, high level of GM3NPhAc on B16F0 cell in vivo may also be achieved. In certain embodiments, the concurrent application of GM3NPhAc-KLH or MPLA-GM3NPhAc vaccine and NeuNPhAc may result in halting metastasis of B16F0 cells in mice.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:
1. A compound of formula I:
(monophosphorylated lipid A)-L-X (I);
wherein L is a linker having a first end Y and a second end Z;
wherein the linker has formula
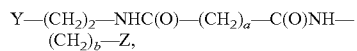
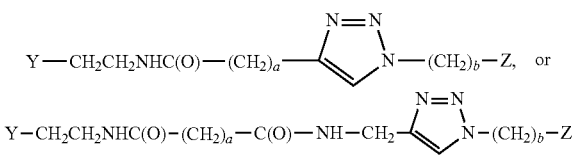
wherein a and b are integers selected from 2 to 6; and
wherein monophosphorylated lipid A is attached at the first end Y of the linker L,
and X is attached at the second end Z of the linker L; and
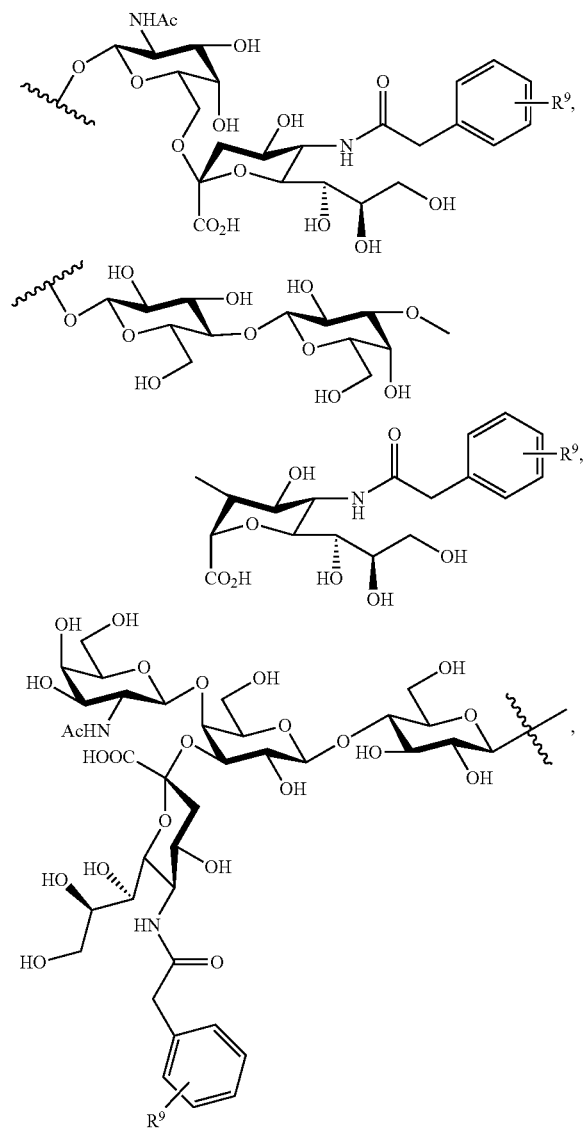
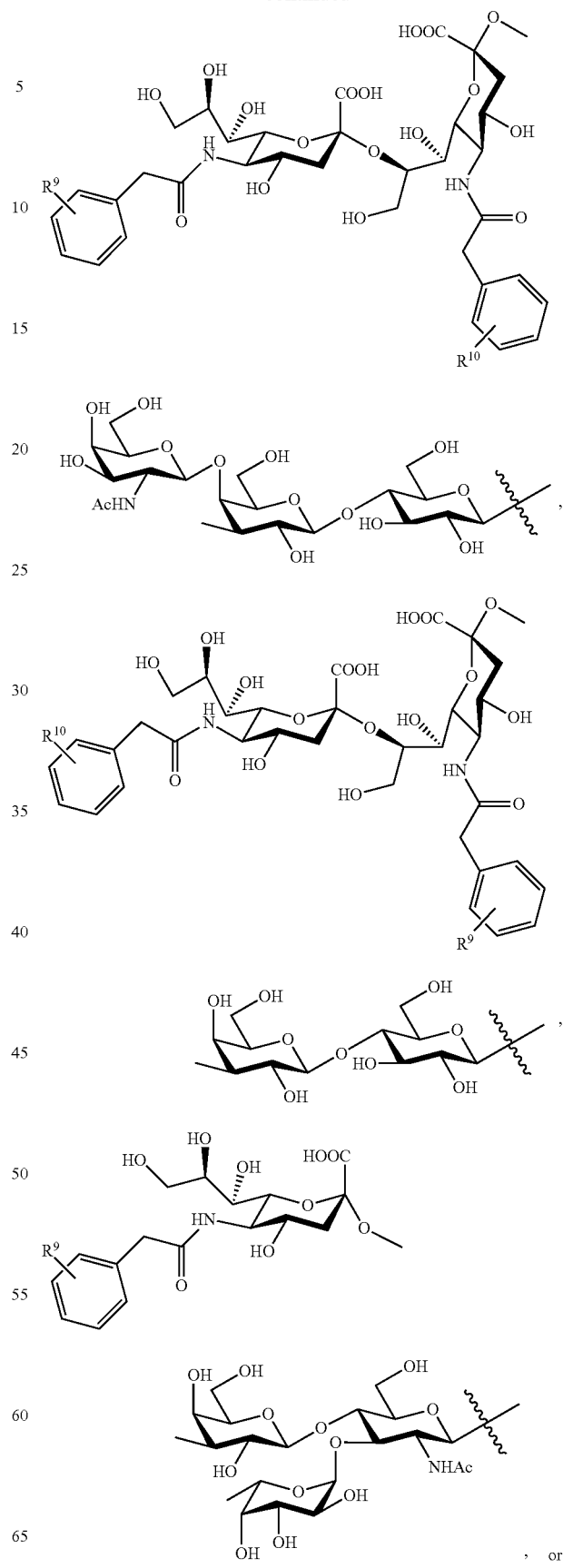

-continued

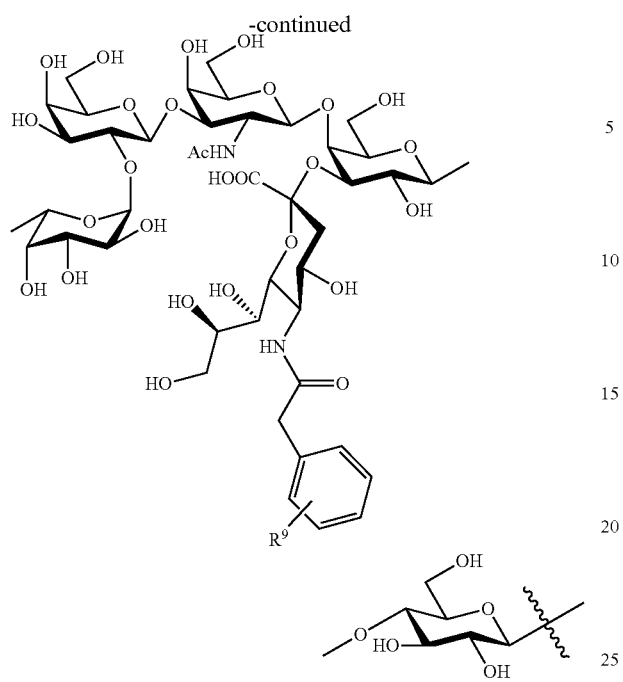

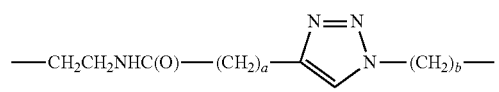

wherein $R^9$ and $R^{19}$ are independently selected from H or one to two substituents selected from the group consisting of $C_1$-$C_6$ alkyl, —O$C_1$-$C_4$ alkyl, —C(O)$C_1$-$C_4$ alkyl, and halo;

or a pharmaceutically acceptable salt thereof.

2. The compound of claim 1, wherein said compound is a compound of formula I:

(monophosphorylated lipid A)-L-X (I);

wherein L is a linker having a first end Y and a second end Z;

wherein the linker has formula Y —(CH$_2$)$_2$—NHC(O)—(CH$_2$)$_a$—C(O)NH—(CH$_2$)$_b$—Z or —CH$_2$CH$_2$NHC(O)—(CH$_2$)$_a$—[triazole]—N—(CH$_2$)$_b$— wherein a and b are integers selected from 2 to 6; and wherein monophosphorylated lipid A is attached at the first end Y of the linker L, and X is attached at the second end Z of the linker L;

and

X is

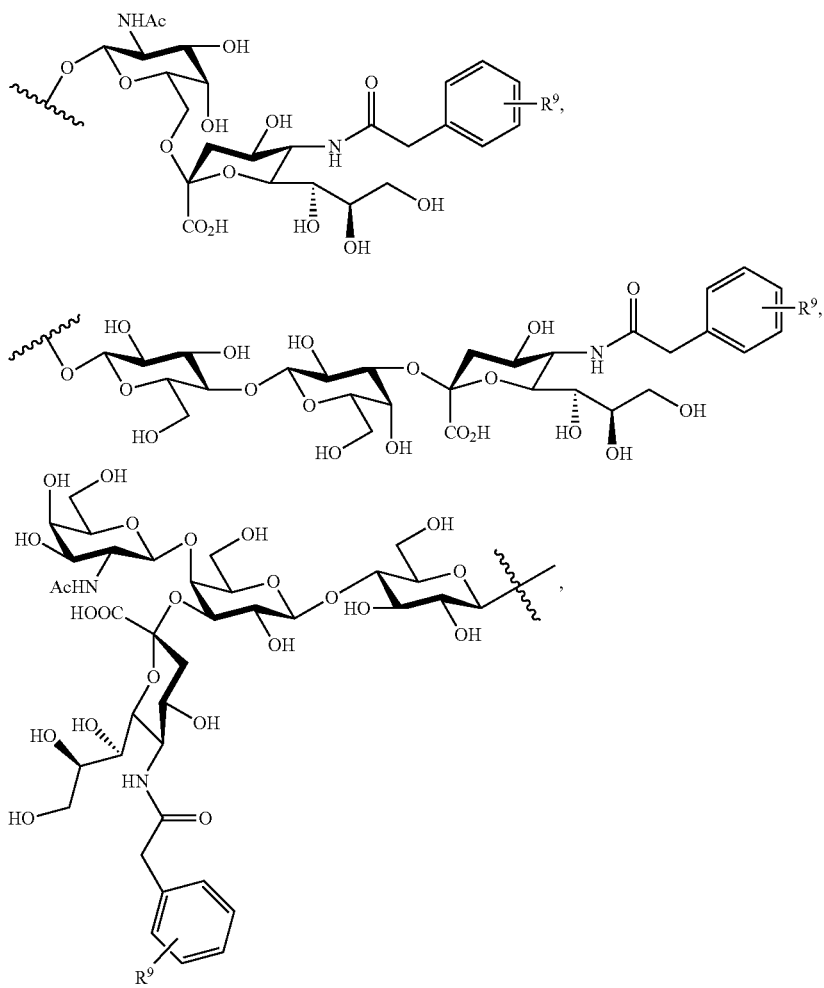

-continued
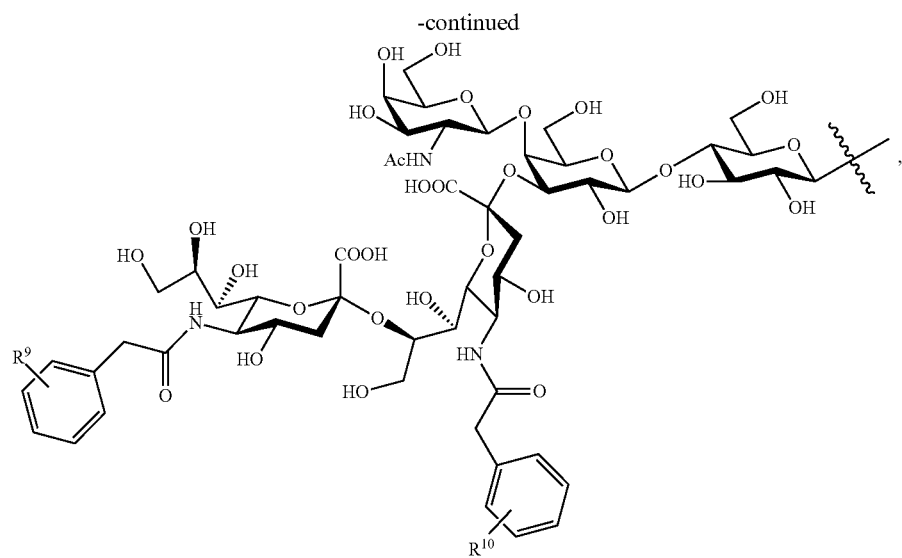
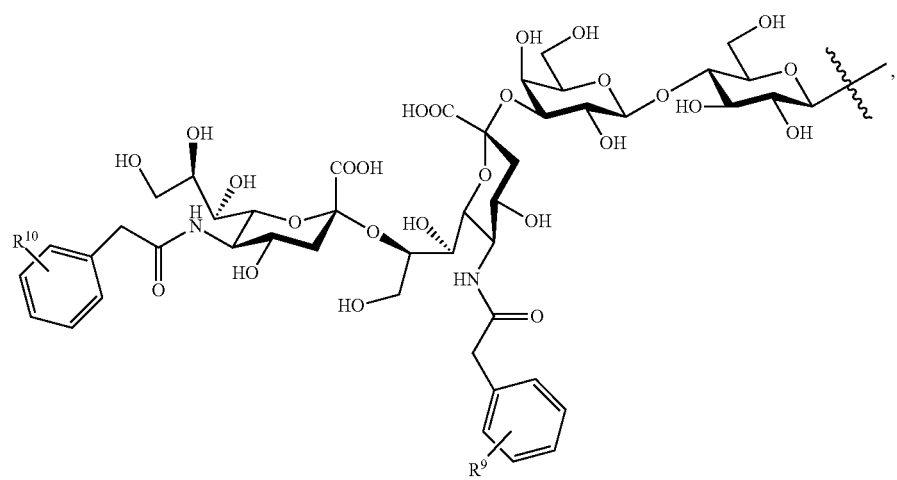
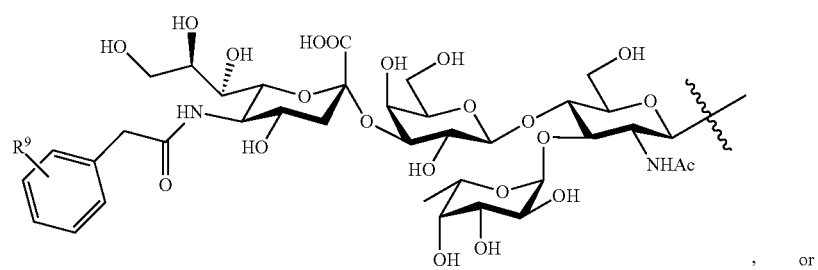
or

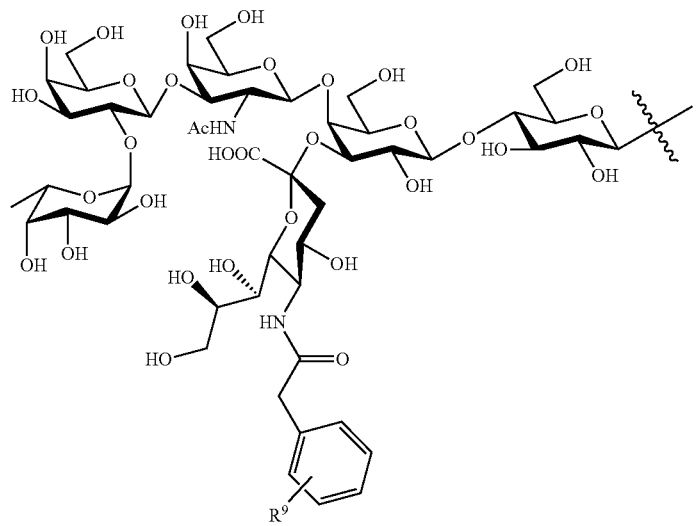

wherein $R^9$ and $R^{10}$ are independently selected from H or one to two substituents selected from the group consisting of $C_1$-$C_6$ alkyl, —$OC_1$-$C_4$ alkyl, —$C(O)C_1$-$C_4$ alkyl, and halo;
or a pharmaceutically acceptable salt thereof.

3. The compound of claim 1, wherein the monophosphorylated lipid A is represented by the following formula:

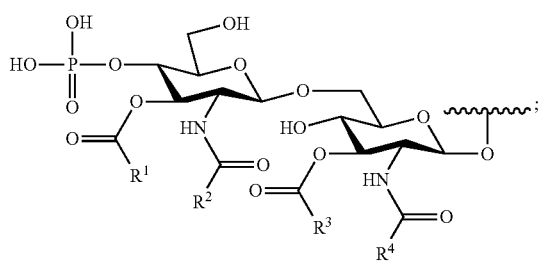

$R^1$ is —$CH_2$—$CH(OR^5)(CH_2)_m CH_3$, $R^5$ is H or —$C(O)$—$(CH_2)_n CH_3$, m is an integer selected from 10 to 12, and n is 12;

$R^2$ is —$CH_2$—$CH(OR^6)(CH_2)_p CH_3$, $R^6$ is —$C(O)$—$(CH_2)_q CH_3$, wherein p is 10, and q is an integer selected from 10 to 12;

$R^3$ is —$CH_2$—$CH(OR^7)(CH_2)_r CH_3$, $R^7$ is H, and r is an integer selected from 8 to 10;

$R^4$ is —$CH_2$—$CH(OR^8)(CH_2)_s CH_3$, $R^8$ is H or —$C(O)$—$(CH_2)_t CH_3$, s is 10 or 11, and t is an integer selected from 11 to 13;

or a pharmaceutically acceptable salt thereof.

4. The compound of claim 1, wherein the monophosphorylated lipid A is represented by the following formula:

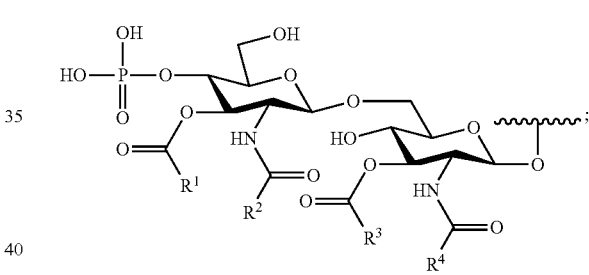

$R^1$ is —$(CH_2)_m CH_3$, wherein m is an integer selected from 10 to 12;

$R^2$ is —$CH_2$—$CH(OR^6)(CH_2)_p CH_3$, $R^6$ is —$C(O)$—$(CH_2)_q CH_3$, wherein p is 10, and q is an integer selected from 10 to 12;

$R^3$ is —$CH_2$—$CH(OR^7)(CH_2)_r CH_3$, $R^7$ is H, and r is an integer selected from 8 to 10;

$R^4$ is —$CH_2$—$CH(OR^8)(CH_2)_s CH_3$, $R^8$ is H or —$C(O)$—$(CH_2)_t CH_3$, s is 10 or 11, and t is an integer selected from 11 to 13;

or a pharmaceutically acceptable salt thereof.

5. The compound of claim 1, wherein $R^9$ and $R^{10}$ are H;
or a pharmaceutically acceptable salt thereof.

6. The compound of claim 1, wherein a and b are each 2;
or a pharmaceutically acceptable salt thereof.

7. The compound of claim 1, wherein said compound is selected from the group consisting of:

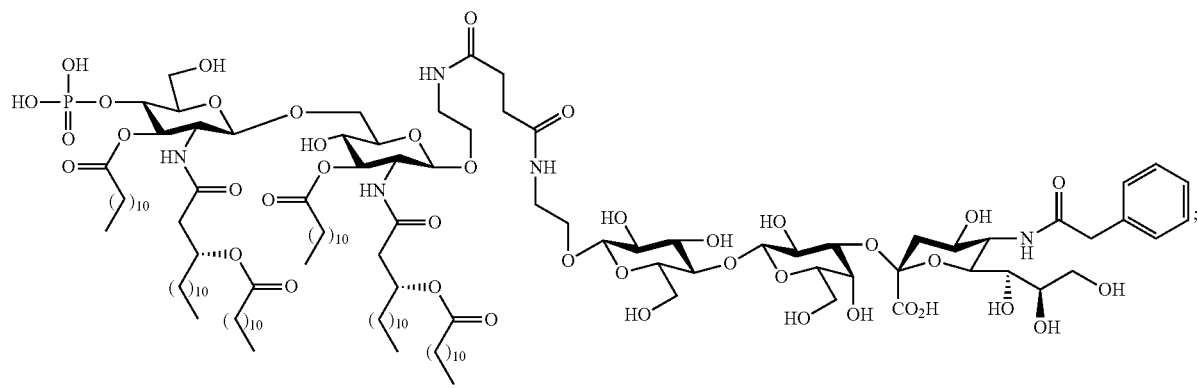
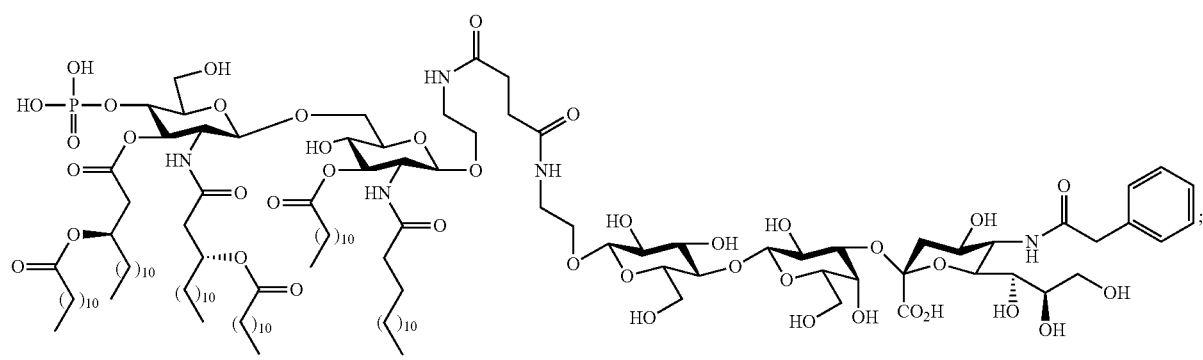
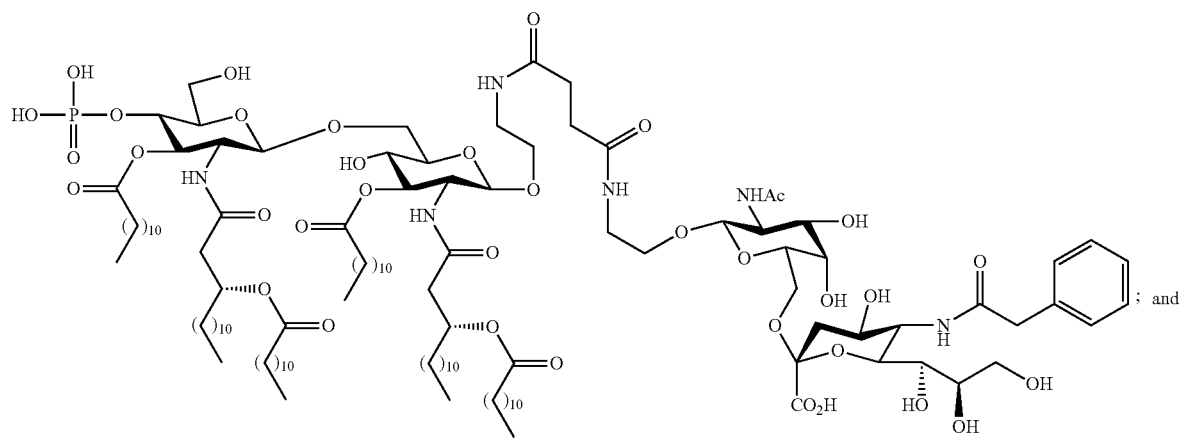
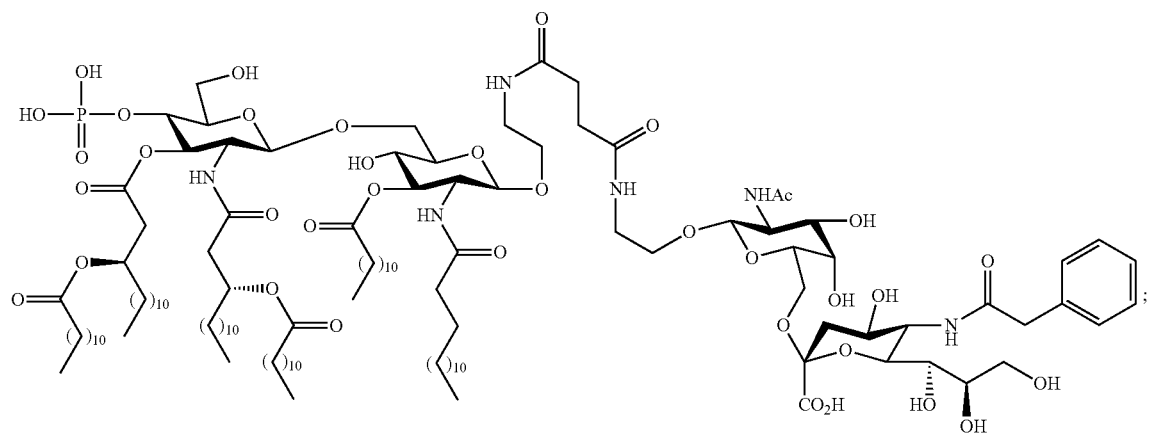
or a pharmaceutically acceptable salt thereof.

8. The compound of claim 1, wherein said compound is selected from the group consisting of:
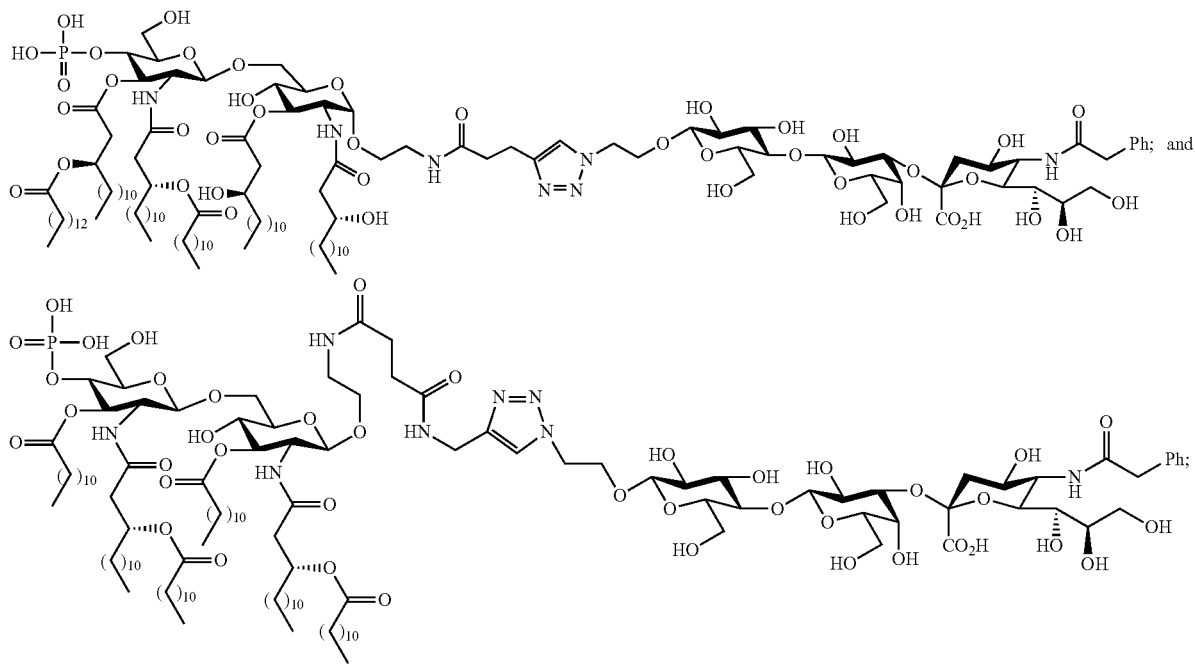
or a pharmaceutically acceptable salt thereof.
9. A compound of Formula IV:
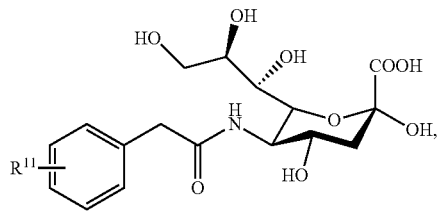
(IV)
wherein $R^{11}$ is one or two substituents independently selected from the group consisting of: $C_1$-$C_6$ alkyl, —$OC_1$-$C_4$ alkyl, —$C(O)C_1$-$C_4$ alkyl, or halo; or a pharmaceutically acceptable salt thereof.
* * * * *

UNITED STATES PATENT AND TRADEMARK OFFICE
CERTIFICATE OF CORRECTION

PATENT NO. : 8,809,285 B2
APPLICATION NO. : 13/387934
DATED : August 19, 2014
INVENTOR(S) : Zhongwu Guo et al.

It is certified that error appears in the above-identified patent and that said Letters Patent is hereby corrected as shown below:

In the Claims

In column 77, after line 21, replace the first formula with the following formula:

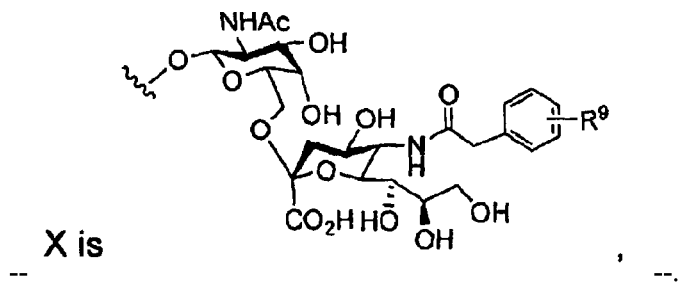

X is

In column 80, line 1, replace "$R^{19}$" with --$R^{10}$--.

Signed and Sealed this
Thirty-first Day of March, 2015

Michelle K. Lee
*Director of the United States Patent and Trademark Office*